US010287279B2

(12) United States Patent
Van Leyen et al.

(10) Patent No.: US 10,287,279 B2
(45) Date of Patent: May 14, 2019

(54) INHIBITORS OF HUMAN 12/15-LIPOXYGENASE

(71) Applicants: THE GENERAL HOSPITAL CORPORATION, Boston, MA (US); THE REGENTS OF THE UNIVERSITY OF CALIFORNIA, Oakland, CA (US); THE UNITED STATES OF AMERICA, as represented by the Secretary, Department of Health and Human Services, Washington, DC (US)

(72) Inventors: Klaus Joachin Van Leyen, Medford, MA (US); Theodore R. Holman, Santa Cruz, CA (US); David J. Maloney, Point of Rocks, MD (US); Ajit Jadhav, Chantilly, VA (US); Anton Simeonov, Santa Cruz, CA (US); Ganesha Rai, Arlington, VA (US)

(73) Assignees: THE CHILDREN'S HOSPITAL CORPORATION, Boston, MA (US); THE REGENTS OF THE UNIVERSITY OF CALIFORNIA, Oakland, CA (US); THE UNITED STATES OF AMERICA, as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 15/048,330

(22) Filed: Feb. 19, 2016

(65) Prior Publication Data

US 2016/0168137 A1 Jun. 16, 2016

Related U.S. Application Data

(63) Continuation-in-part of application No. PCT/US2014/052269, filed on Aug. 22, 2014.

(60) Provisional application No. 61/868,611, filed on Aug. 22, 2013.

(51) Int. Cl.
| | |
|---|---|
| *C07D 413/04* | (2006.01) |
| *C07D 277/56* | (2006.01) |
| *C07D 263/48* | (2006.01) |
| *A61K 31/421* | (2006.01) |
| *A61K 31/422* | (2006.01) |
| *A61K 31/426* | (2006.01) |
| *A61K 31/4709* | (2006.01) |
| *A61K 31/4725* | (2006.01) |
| *A61K 31/4245* | (2006.01) |
| *C07D 277/42* | (2006.01) |
| *C07D 213/85* | (2006.01) |
| *C07D 239/42* | (2006.01) |

(52) U.S. Cl.
CPC .......... *C07D 413/04* (2013.01); *A61K 31/421* (2013.01); *A61K 31/422* (2013.01); *A61K 31/426* (2013.01); *A61K 31/4245* (2013.01); *A61K 31/4709* (2013.01); *A61K 31/4725* (2013.01); *C07D 213/85* (2013.01); *C07D 239/42* (2013.01); *C07D 263/48* (2013.01); *C07D 277/42* (2013.01); *C07D 277/56* (2013.01)

(58) Field of Classification Search
CPC .. C07D 413/04; C07D 213/85; C07D 239/42; C07D 263/48; C07D 277/42; C07D 277/56; A61K 31/421; A61K 31/422; A61K 31/4245; A61K 31/426; A61K 31/4709; A61K 31/4725
USPC ........................................................ 548/240
See application file for complete search history.

(56) References Cited

FOREIGN PATENT DOCUMENTS

| WO | 2009/134938 A1 | 11/2009 |
|---|---|---|
| WO | 2010/111711 A2 | 9/2010 |
| WO | 2010/118347 A2 | 10/2010 |
| WO | 2011/028651 A1 | 3/2011 |
| WO | 2012/075393 A2 | 6/2012 |
| WO | 2012/161879 A1 | 11/2012 |

OTHER PUBLICATIONS

Morwick et al., Evolution of the Thienopyridine Class of Inhibitors of IkappaB Kinase-beta: Part I: Hit-to-Lead Strategies, 2006, J. Med. Chem., 49, 2898-2908.*
Ganesha et al., "Potent and selective inhibitors of human reticulocyte 12/15-lipoxygenase as anti-stroke therapies", J Med Chem. 57(10):4035-4048 (2014).
Markt et al., "Discovery of novel cathepsin S inhibitors by pharmacophore-based virtual high-throughput screening", J Chem Inf Model. 48(8):1693-1705 (2008).
Amagata et al., "Exploring Sponge-Derived Terpenoids for Their Potency and Selectivity against 12-Human, 15-Human, and 15-Soybean Lipoxygenases", Journal of Natural Products 66:230-235 (2003).

(Continued)

*Primary Examiner* — Kristin Vajda
(74) *Attorney, Agent, or Firm* — Nixon Peabody LLP; David S. Resnick

(57) ABSTRACT

A systematic screening has revealed a family of compounds that exhibit inhibitory effects on 12/15-lipoxygenase. Accordingly, the present invention relates to the use of these compounds for the inhibition of 12/15-lipoxygenase and for the treatment of a condition involving 12/15-lipoxygenase. Exemplary conditions include, but are not limited to, stroke, periventricular leukomalacia, cardiac arrest with resuscitation, atherosclerosis, Parkinson's disease, Alzheimer's disease, and breast cancer.

19 Claims, 12 Drawing Sheets

(56) References Cited

OTHER PUBLICATIONS

Bleich et al., "The role of 12-lipoxygenase in pancreatic β-cells (Review)", International Journal of Molecular Medicine 1:265-272 (1998).

Canals et al., "Nitric Oxide Triggers the Toxicity due to Glutathione Depletion in Midbrain Cultures through 12-Lipoxygenase", The Journal of Biological Chemistry 278(24):21542-21549 (2003).

Carroll et al., "Probing Sponge-Derived Terpenoids for Human 15-Lipoxygenase Inhibitors", The Journal of Organic Chemistry 66(21):6847-6851 (2001).

Chen et al., "Purification and characterization of recombinant histidine-tagged human platelet 12-lipoxygenase expressed in a baculovirus/insect cell system", European Journal of Biochemistry 214:845-852 (1993).

Cichewicz et al., "Redox Inactivation of Human 15-Lipoxygenase by Marine-Derived Meroditerpenes and Synthetic Chromanes: Archetypes for a Unique Class of Selective and Recyclable Inhibitors", Journal of the American Chemical Society 126:14910-14920 (2004).

Connolly et al., "Enhanced angiogenesis and growth of 12-lipoxygenase gene-transfected MCF-7 human breast cancer cells in athymic nude mice", Cancer Letters 132:107-112 (1998).

Deschamps et al., "Baicalein is a Potent In Vitro Inhibitor against both Reticulocyte 15-Human and Platelet 12-Human Lipoxygenase", Bioorganic & Medicinal Chemistry 14(12):4295-4301 (2006).

Ding et al., "Lipoxygenase Inhibitors Abolish Proliferation of Human Pancreatic Cancer Cells", Biochemical and Biophysical Research Communications 261:218-223 (1999).

Dobrian et al., "Differential Expression and Localization of 12/15 Lipoxygenases in Adipose Tissue in Human Obese Subjects", Biochemical and Biophysical Research Communications 403(3-4):485-490 (2010).

Haeggstrom et al., "Lipoxygenase and Leukotriene Pathways: Biochemistry, Biology, and Roles in Disease", Chemical Reviews 111:5866-5898 (2011).

Haynes et al., "12/15-Lipoxygenase Expression Is Increased in Oligodendrocytes and Microglia of Periventricular Leukomalacia", Developmental Neuroscience 35:140-154 (2013).

Hedrick et al., "12-Lipdxygenase Products Increase Monocyte: Endothelial Interactions", Eicosanoids and Other Bioactive Lipids in Cancer, Inflammation, and Radiation Injury 4:455-460 (1999).

Hoobler et al., "Pseudoperoxidase investigations of hydroperoxides and inhibitors with human lipoxygenases", Bioorganic & Medicinal Chemistry 21:3894-3899 (2013).

Hussain et al., "Epidermis contains platelet-type 12-lipoxygenase that is overexpressed in germinal layer keratinocytes in psoriasis", American Journal of Physiology-Cell Physiology 266:C243-C253 (1994).

Jin et al., "Protecting Against Cerebrovascular Injury", Stroke 39:2538-2543 (2008).

Kenyon et al., "Novel Human Lipoxygenase Inhibitors Discovered Using Virtual Screening with Homology Models", Journal of Medicinal Chemistry 49:1356-1363 (2006).

Kenyon et al., "Discovery of Potent and Selective Inhibitors of Human Platelet type 12-Lipoxygenase", Journal of Medicinal Chemistry 54(15):5485-5497 (2011).

Khanna et al., "Molecular Basis of Vitamin E Action. Tocotrienol Modulates 12-Lipoxygenase, a Key Mediator of Glutamate-Induced Neurodegeneration", Journal of Biological Chemistry 278(44):43508-43515 (2003).

Kuhn et al., "Mammalian arachidonate 15-lipoxygenases: Structure, function, and biological implications", Prostaglandins & other Lipid Mediators 68-69:263-290 (2002).

Li et al., "A Role for 12-lipoxygenase in nerve Cell Death Caused by Glutathione Depletion", Neuron 19:453-463 (1997).

Lovat et al., "GADD153 and 12-Lipoxygenase Mediate Fenretinide-induced Apoptosis of Neuroblastoma", Cancer Researchesearch 62:5158-5167 (2002).

Malterud et al., "Inhibitors of 15-Lipoxygenase from Orange Peel", Journal of Agricultural and Food Chemistry 48 :(11):5576-5580 (2000).

Viogul et al., "Oleyl Sulfate Reveals Allosteric Inhibition of Soybean Lipoxygenase-1 and Human 15-Lipoxygenase", Biochemistry 39(16):4801-4807 (2000).

Ngu et al., "Pyrazole-based sulfonamide and sulfamides as potent inhibitors of mammalian 15-lipoxygenase", Bioorganic & Medicinal Chemistry Letters 21:4141-4145 (2011).

Nunemaker et al., "12-Lipoxygenase-knockout mice are resistant to inflammatory effects of obesity induced by western diet", American Journal of Physiology-Endocrinology and Metabolism 295:E1065-E1075 (2008).

Obrosova et al., "Different Roles of 12/15-Lipoxygenase in Diabetic Large and Small Fiber Peripheral and Autonomic Neuropathies", The American Journal of Pathology 177(3):1436-1447 (2010).

Ohri et al., "A Re(V)-Catalyzed C—N Bond-Forming Route to Human Lipoxygenase Inhibitors", Organic Letters 7 (12):2501-2504 (2005).

Pallast et al., "12/15-Lipoxygenase targets neuronal mitochondria under oxidative stress", Journal of Neurochemistry 111:882-889 (2009).

Pallast et al., "Increased nuclear apoptosis-inducing factor after transient focal ischemia: a 12/15-lipoxygenase-dependent organelle damage pathway", Journal of Cerebral Blood Flow & Metabolism 30(6):1157-1167 (2010).

Pratico et al., "12/15-Lipoxygenase Is Increased in Alzheimer's Disease: Possible Involvement in Brain Oxidative Stress", American Journal of Pathology 164(5):1655-1662 (2004).

Rai et al., "Discovery of Potent and Selective Inhibitors of Human Reticulocyte 15-Lipoxygenase-1", Journal of Medicinal Chemistry 53(20):7392-7404 (2010).

Robinson et al., "Using Enzyme Assays to Evaluate the Structure and Bioactivity of Sponge-Derived Meroterpenes", Journal of Natural Products 72(10):1857-1863 (2009).

Schnurr et al., "The Selenoenzyme Phospholipid Hydroperoxide Glutathione Peroxidase Controls the Activity of the 15-Lipoxygenase with Complex Substrates and Preserves the Specificity of the Oxygenation Products", The Journal of Biological Chemistry 271(9):4653-4658 (1996).

Seiler et al., "Glutathione Peroxidase 4 Senses and Translates Oxidative Stress into 12/15-Lipoxygenase Dependent-and AIF-Mediated Cell Death", Cell Metabolism 8:237-248 (2008).

Sendobry et al., "Attenuation of diet-induced atherosclerosis in rabbits with a highly selective 15-lipoxygenase Inhibitor lacking significant antioxidant properties", British Journal of Pharmacology 120:1199-1206 (1997).

Stavniichuk et al., "Role of 12/15-Lipdxygenase in Nitrosative Stress and Peripheral Prediabetic and Diabetic Neuropathies", Free Radical Biology and Medicine 49(6):1036-1045 (2010).

Succol et al., "A role for 12/15 lipoxygenase in the amyloid β precursor protein metabolism", Journal of Neurochemistry 103:380-387 (2007).

Tong et al., "Leukotriene B4 Receptor Antagonist LY293111 Inhibits Proliferation and Induces Apoptosis in Human Pancreatic Cancer Cells", Clinical Cancer Research 8:3232-3242 (2002).

Van Leyen et al., "12/15-lipoxygenase and the proteasome as mediators of neuronal oxidative stress and stroke", Program No. 135.6,Neuroscienc.e Meeting Planner: Society for Neuroscience (2004).

Van Leyen et al., "Baicalein and 12/15-Lipoxygenase in the Ischemic Brain", Stroke 37:3014-3018 (2006).

Vasquez-Martinez et al., "Structure Activity Relationship Studies of Flavonoids as Potent Inhibitors of Human Platelet 12-hLO, Reticulocyte 15-hLO-1, and Prostate Epithelial 15-hLO-2", Bioorganic & Medicinal Chemistry 15 (23):7408-7425 (2007).

Weaver et al., "Integration of pro-inflammatory cytokines, 12-lipoxygenase and NOX-1 in pancreatic islet beta cell dysfunction", Molecular and Cellular Endocrinology 358:88-95 (2012).

Wecksler et al., "Substrate Specificity Changes for Human Reticulocyte and Epithelial 15-Lipoxygenases Reveal Allosteric Product Regulation", Biochemistry 47(28):7364-7375 (2008).

(56) References Cited

OTHER PUBLICATIONS

Weinstein et al., "Tryptamine and homotryptamine-based sulfonamides as potent and selective inhibitors of 15-lipoxygenase", Bioorganic & Medicinal Chemistry Letters 15:1435-1440 (2005).
Weinstein et al., "Discovery of selective imidazole-based inhibitors of mammalian 15-lipoxygenase: Highly potent against human enzyme within a cellular environment", Bioorganic & Medicinal Chemistry Letters 17:5115-5120 (2007).
Whitman et al., "Structure-Activity Relationship Studies of Nordihydroguaiaretic Acid Inhibitors Toward Soybean, 12-Human, and 15-Human Lipoxygenase", Journal of Medicinal Chemistry 45(12):2659-2661 (2002).
Xia et al., "Metal-mediated Variants of the Passerini Reaction: A New Synthesis of 4-Cyanooxazoles", Synthesis 14:1969-1972 (2002).
Yao et al., "Elevation of 12/15 Lipoxygenase Products in AD and Mild Cognitive Impairment", Annals of Neurology 58(4):623-626 (2005).
Yigitkanli et al., "Inhibition of 12/15-lipoxygenase as therapeutic strategy to treat stroke", Annals of Neurology 73 (1):129-135 (2013).
Pubchem, "Aid 2155—Cuyette-Based Assay fo Inhibitors of 15-hL0-1 (15-human lipoxygenase 1): Series 1—Round 1", Version 1.2 (Feb. 14, 2011).

\* cited by examiner

R =

2i = 2-naphthyl
3i = isoquinolin-5-yl
4i = quinolin-5-yl
5i = isoquinolin-6-yl
6i = quinoxalin-5-yl
7i = 2,3-dichlorophenyl
8i = 3,4-dichlorophenyl
9i = 2,3-dihydrobenzo[b][1,4]dioxin-6-yl 10i = 1,3-benzodioxol-5-yl
11i = 4-biphenyl
12i = 2-biphenyl
13i = indol-6-yl
14i = indol-3-yl
15i = 4-chlorophenyl
16i = 3-chlorophenyl
17i = 4-fluorophenyl
18i = cyclopentyl
19 = 1-naphthyl

INHIBITORS OF HUMAN 12/15-LIPOXYGENASE

CROSS-REFERENCE TO RELATED APPLICATION

This Continuation-in-Part application claims benefit under 35 U.S.C. 111(a) of co-pending International Application No. PCT/US2014/052269 filed Aug. 22, 2014, which claims benefit under 35 U.S.C. §119(e) of U.S. Provisional Application No. 61/868,611 filed Aug. 22, 2013, the contents of each of which are incorporated herein by reference in their entireties.

GOVERNMENT SUPPORT

This invention was made with government support under grant No. R01 NS049430, R01 NS069939, R01 GM56062, R03 MH081283, and U54MH084681 awarded by the National Institutes of Health (NIH). The government has certain rights in the invention.

TECHNICAL FIELD

The present invention relates generally to inhibition of 12/15-lipoxygenase, treatment of a condition involving 12/15-lipoxygenase including, but not limited to, strokes, periventricular leukomalacia, cardiac arrest with resuscitation, atherosclerosis, Parkinson's disease, Alzheimer's disease, and breast cancer.

BACKGROUND

Classical drug discovery to a large extent relies on animal models of disease, mostly in rodents. The reasons for this are manifold, but in part they center on practical aspects such as availability and cost, compounded by ethical considerations. Mice and rats are most frequently used, and many diseases have been modeled in these species. One question that has of late received more attention is that of species variability. Even if the disease is modeled well in the animal, variability in the drug target between humans and rodents may still lead to failed human trials, a venture that is both costly and time-consuming. One example of this is 12/15-lipoxygenase (12/15-LOX), an enzyme, which contributes to ischemic brain injury in both humans and mice.

The lipoxygenases form a large family of enzymes capable of oxidizing arachidonic acid (AA) and related polyunsaturated fatty acids (Brash A R, J. Biol. Chem. 1999, 274, 23679-23682). In humans, in addition to 12/15-LOX, other members include 5-LOX, P-12-LOX, 12(R)-LOX, epidermal LOX-3, and 15-LOX-2. Their nomenclature is based in part upon the tissue where they were first detected, and in part upon the carbon atom in AA that is oxidized. Correspondingly, 12/15-LOX can oxidize both C12 and C15, forming 12- or 15-hydroperoxyarachidonic acid (12- or 15-HPETE), respectively. Human lipoxygenases and their metabolites have been implicated in numerous diseases. 5-LOX has been implicated in cancer, asthma, COPD, allergic rhinitis, osteoarthritis, and atherosclerosis, while platelet-type 12-LOX has been implicated in diabetes, blood coagulation, psoriasis, and cancer. Human reticulocyte 15-lipoxygenase-1 (12/15-LOX, aka 15-LOX-1) is also an attractive therapeutic target, particularly for its role in atherogenesis, diabetes, Alzheimer's, newborn periventricular leukomalacia, breast cancer and stroke (Tong, W. G., et al., Clin. Can. Res. 2002, 8, 3232-3242; Pratico, D.; Zhukareva, V., et al., Am. J. Pathol. 2004, 164, 1655-1662).

The 12/15-LOX has historically been called 15-LOX, 15-LOX-1, or 15-LO-1 in humans, L-12-LOX, leukocyte-type 12-LO, or L-12-LO in mice. The number prefix reflects the preference for 15-HETE in humans, vs. mostly 12-HETE for the mouse 12/15-LOX. The gene in both organisms is termed ALOX15, reflecting the close homology (around 78%) and functional equivalence in both species. Mutation of a key residue in the active site of the rabbit 12/15-LOX which normally generates mostly 15-HETE, switches the product ratio towards the 12 product (Borngraber et al., J. Biol. Chem. 1999, 274, 37345-37350). The variability in the product spectrum thus reflects differences in the active site binding pocket, which is otherwise similar in most lipoxygenases, although the orientation of arachidonic acid presumably varies (Schwarz et al., Biochemistry 1998, 37, 15327-15335).

The difficulty in developing inhibitors that target LOX homologues in both species is that they have different substrate specificities and presumably different inhibitor specificities. Thus, existing inhibitors of 12/15-LOX are typically not very selective with regard to other LOX isoforms, and many additionally are strong antioxidants. While this latter fact may not in itself be damaging, the inherent lack of selectivity suggests a much greater potential for off-target effects.

Introducing humanized versions of the drug target into the animal model is one way to meet the challenge of species-to-species variability, but this approach is in most cases not available. It is therefore of great importance to identify bioactive compounds that target a specific pathway both in rodents, and in humans.

SUMMARY

Provided herein are compositions and methods for treating a condition involving 12/15-lipoxygenase. Through a systematic succession of screening steps, the inventors have identified novel inhibitors of human 12/15-lipoxygenase (12/15-LOX), which can also target the mouse 12/15-LOX homologue.

In one aspect, provided herein is a method of treating a condition involving 12/15-lipoxygenase in a subject, the method comprising administering to the subject an effective amount of a compound of Formula I:

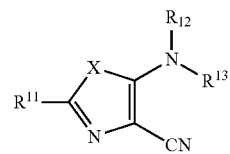

Formula I or a pharmaceutically acceptable salt thereof, in which:
X is O or S;
$R^{11}$ is an aryl, heteroaryl, cyclyl, or heterocyclyl, each of which can be optionally substituted; and
$R^{12}$ and $R^{13}$ are independently hydrogen, halogen, alkyl, alkenyl, alkynyl, aralkyl, acyl, aryl, heteroaryl, cyclyl or heterocyclyl, each of which can be optionally substituted.

In some embodiments, $R^{11}$ is an aryl or heteroaryl, each of which can be optionally substituted.

In some embodiments, $R^{11}$ is 1-naphthyl, 2-naphthyl, 6-isoquinolinyl, 2,3-dichlorophenyl, or 3,4-dichlorophenyl.

In some embodiments, $R^{12}$ is hydrogen, alkyl, aralkyl, acyl, aryl, or heterocyclyl, each of which can be optionally substituted.

In some embodiments, $R^{12}$ is hydrogen, methyl, ethyl, propyl, butyl, pentyl, or phenyl.

In some embodiments, $R^{13}$ is hydrogen, alkyl, aralkyl, acyl, aryl, or heterocyclyl, each of which can be optionally substituted.

In some embodiments, $R^{13}$ is hydrogen, methyl, ethyl, propyl, butyl, pentyl, or phenyl.

In some embodiments, $R^{12}$ is hydrogen and $R^{13}$ is hydrogen, methyl, ethyl, propyl, butyl, pentyl, or phenyl.

In some embodiments, X is O.

In some embodiments, X is S.

In some embodiments, the compound of Formula I is of:
(i) Formula II:

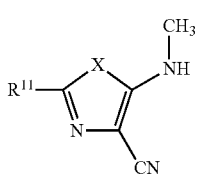

Formula II or a pharmaceutically acceptable salt thereof, in which:
X is O or S; and
$R^{11}$ is an aryl, heteroaryl, cyclyl, or heterocyclyl, each of which can be optionally substituted; or
(ii) Formula III:

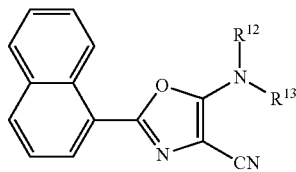

Formula III or a pharmaceutically acceptable salt thereof, in which:
$R^{12}$ and $R^{13}$ are independently hydrogen, halogen, alkyl, alkenyl, alkynyl, aralkyl, acyl, aryl, heteroaryl, cyclyl or heterocyclyl, each of which can be optionally substituted.

In some embodiments, the compound is selected from the group consisting of 5-(methylamino)-2-naphthalen-1-yl-1,3-oxazole-4-carbonitrile (ML351), 2-(2,3-dichlorophenyl)-5-(methylamino)-1,3-oxazole-4-carbonitrile, 2-(3,4-dichlorophenyl)-5-(methylamino)-1,3-oxazole-4-carbonitrile, 5-(methylamino)-2-naphthalen-1-yl-1,3-thiazole-4-carbonitrile.

In some embodiments, the compound is 5-(methylamino)-2-naphthalen-1-yl-1,3-oxazole-4-carbonitrile (ML351).

In some embodiments, the compound inhibits 12/15-lipoxygenase.

In some embodiments, the condition is stroke, periventricular leukomalacia, cardiac arrest with resuscitation, atherosclerosis, Parkinson's disease, Alzheimer's disease, or breast cancer.

In some embodiments, the subject is a mammal.

In some embodiments, the subject is a human.

In another aspect, provided herein is the use of a compound of Formula I:

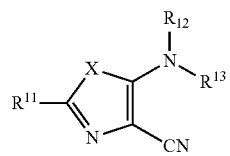

Formula I or a pharmaceutically acceptable salt thereof for the preparation of a medicament for the treatment of a condition involving 12/15-lipoxygenase, wherein:
X is O or S;
$R^{11}$ is an aryl, heteroaryl, cyclyl, or heterocyclyl, each of which can be optionally substituted; and
$R^{12}$ and $R^{13}$ are independently hydrogen, halogen, alkyl, alkenyl, alkynyl, aralkyl, acyl, aryl, heteroaryl, cyclyl or heterocyclyl, each of which can be optionally substituted.

In some embodiments, the compound of Formula I is of:
(i) Formula II:

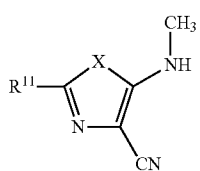

Formula II or a pharmaceutically acceptable salt thereof, wherein:
X is O or S; and
$R^{11}$ is an aryl, heteroaryl, cyclyl, or heterocyclyl, each of which can be optionally substituted; or
(ii) Formula III:

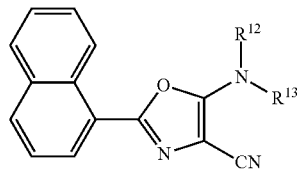

Formula III or a pharmaceutically acceptable salt thereof, wherein:
$R^{12}$ and $R^{13}$ are independently hydrogen, halogen, alkyl, alkenyl, alkynyl, aralkyl, acyl, aryl, heteroaryl, cyclyl or heterocyclyl, each of which can be optionally substituted.

In some embodiments, the compound is selected from the group consisting of 5-(methylamino)-2-naphthalen-1-yl-1,3-oxazole-4-carbonitrile (ML351), 2-(2,3-dichlorophenyl)-5-(methylamino)-1,3-oxazole-4-carbonitrile, 2-(3,4-dichlorophenyl)-5-(methylamino)-1,3-oxazole-4-carbonitrile, and 5-(methylamino)-2-naphthalen-1-yl-1,3-thiazole-4-carbonitrile.

In some embodiments, the condition is stroke, periventricular leukomalacia, cardiac arrest with resuscitation, atherosclerosis, Parkinson's disease, Alzheimer's disease, or breast cancer.

BRIEF DESCRIPTION OF THE DRAWINGS

FIG. 2A is a graph showing % of the 12-HETE secreted from glutamate-treated cells vs % cell death in glutamate-treated samples.

FIG. 2B is a graph showing positive correlation between 15-HETE and cell death.

(FIG. 7A) Plot of $K_M$/Vmax versus inhibitor concentration (μM) yielded a $K_i$ of 0.1±0.002 μM. (FIG. 7B) Plot of $1/V_{max}$ versus inhibitor concentration (μM) yielded a $K_i'$ of 1.2±0.02 μM ($V_{max}$ units are μmol/min/mg).

DETAILED DESCRIPTION

Figure 1A:
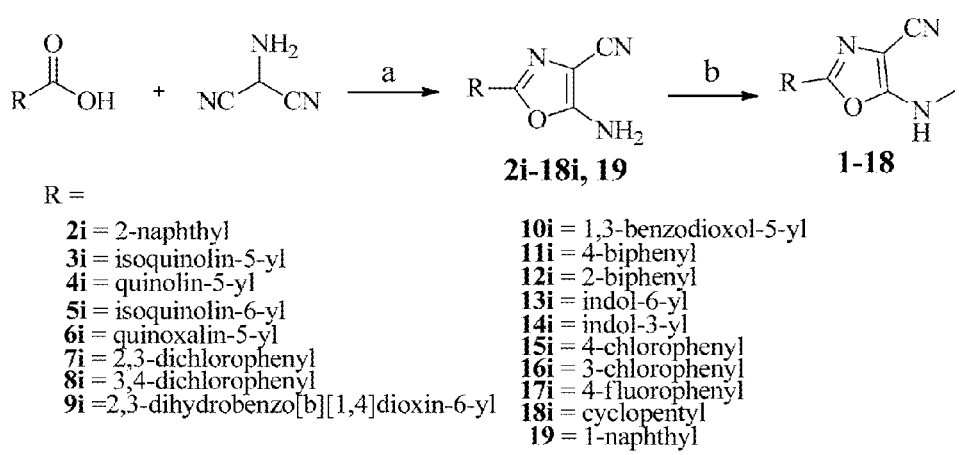
FIGS. 1A-1J are synthesis schemes of the various compounds described in the present invention.

Through a systematic succession of screening steps, the inventors have identified novel inhibitors of human 12/15-lipoxygenase (12/15-LOX), which can also target the mouse 12/15-LOX homologue. Accordingly, embodiments of the present invention provide, inter alia, 12/15-LOX inhibitors that work against both the human and the mouse version of 12/15-LOX and methods of uses thereof.

One aspect of the invention relates to small molecule compounds that are 12/15-LOX inhibitors. In some embodiments, the compound corresponds to Formula I:

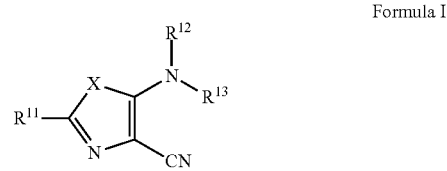

Formula I or a pharmaceutically acceptable salt thereof.

In some embodiments, the compound of Formula I is of (i) Formula II:

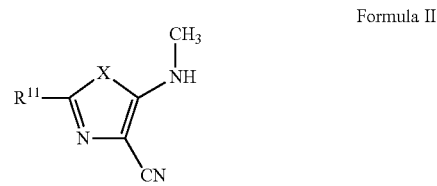

Formula II or a pharmaceutically acceptable salt thereof; or
(ii) Formula III:

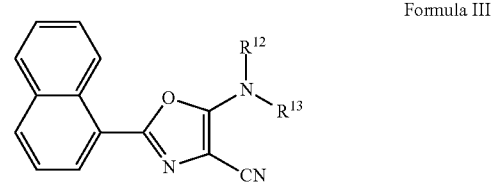

Formula III or a pharmaceutically acceptable salt thereof.

In compounds of Formula I or II, X can be O or S, and $R^{11}$ can be an aryl, heteroaryl, cyclyl, or heterocyclyl, each of which can be optionally substituted.

In compounds of Formula I or III, $R^{12}$ and $R^{13}$ are independently hydrogen, halogen, alkyl, alkenyl, alkynyl, aralkyl, acyl, aryl, heteroaryl, cyclyl or heterocyclyl, each of which can be optionally substituted.

In some embodiments, $R^{11}$ is an aryl or heteroaryl, each of which can be optionally substituted. In some embodiments, $R^{11}$ is a monocyclic aryl, bicyclic aryl, monocyclic heteroaryl, or bicyclic heteroaryl, each of which can be optionally substituted. In some embodiments, $R^{11}$ is an optionally substituted phenyl. When the phenyl group is substituted, the substituent can be present at the ortho, meta, or para position on the phenyl relative to the rest of the compound. In some embodiments, the optionally substituted aryl or heteroaryl is substituted with one or more substituents selected from amino, halogen, hydroxyl, thiol, methoxy, methylthioxy, carboxyl, nitro, cyano, and any combinations thereof. In some embodiments, the heteroaryl comprises one or more heteroatoms (e.g., 1, 2, 3, 4, 5, or more) selected from O, S, N, and a combination thereof.

In some embodiments, $R^{11}$ is 1-naphthyl, 2-naphthyl, 5-isoquinolinyl, 6-isoquinolinyl, 5-quinolinyl, 2,3-dichlorophenyl, 3,4-dichlorophenyl, 5-benzo[d][1,3]dioxolyl, 3-1H-indolyl, or 3-chlorophenyl. In some embodiments, $R^{11}$ is 1-naphthyl, 2-naphthyl, 6-isoquinolinyl, 2,3-dichlorophenyl, 3,4-dichlorophenyl, or

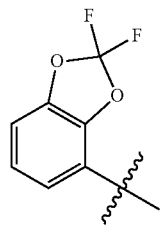

In some embodiments, $R^{12}$ and $R^{13}$ are independently hydrogen, alkyl, aralkyl, alkenyl, acyl, aryl, or heterocyclyl, each of which can be optionally substituted. In some embodiments, the alkyl is $C_1$-$C_{10}$ alkyl. In some embodiments, the alkyl is $C_1$-$C_6$ alkyl such as methyl, ethyl, propyl, isopropyl, butyl, sec-butyl, isobutyl, tert-butyl, pentyl, neopentyl, and hexyl.

In some embodiments, when $R^{12}$ is hydrogen, $R^{13}$ can be methyl, ethyl, propyl, butyl, pentyl, formyl, acetyl, benzyl, phenyl,

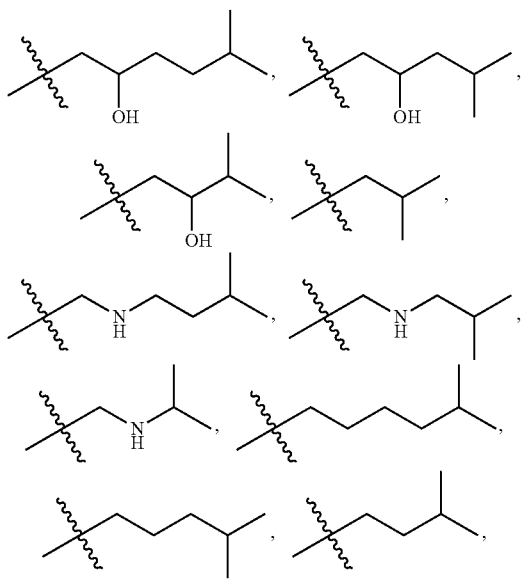

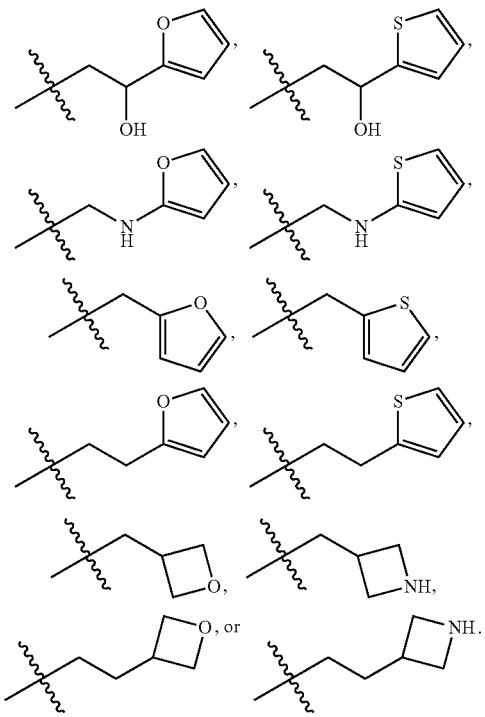

In some embodiments, $R^{12}$ and $R^{13}$ are both methyl.

In some embodiments, the compound is selected from the group consisting of 5-(methylamino)-2-naphthalen-1-yl-1,3-oxazole-4-carbonitrile (also referred herein as ML351), 2-(2,3-dichlorophenyl)-5-(methylamino)-1,3-oxazole-4-carbonitrile, 2-(3,4-dichlorophenyl)-5-(methylamino)-1,3-oxazole-4-carbonitrile, 5-(methylamino)-2-naphthalen-1-yl-1,3-thiazole-4-carbonitrile.

In some embodiments, the compound is 5-(methylamino)-2-naphthalen-1-yl-1,3-oxazole-4-carbonitrile (ML351).

In some embodiments, the compound can cross the blood-brain barrier.

In some embodiments, the compound can selectively inhibit 12/15-LOX.

Set forth below are some specific examples of the compounds which can be used to practice the methods of this invention:

Compound 1

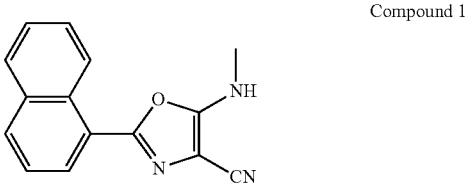

Compound 2

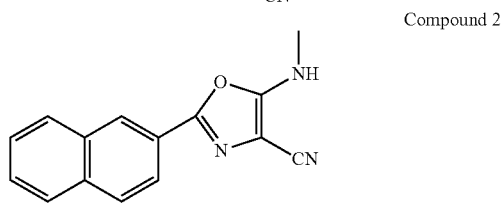

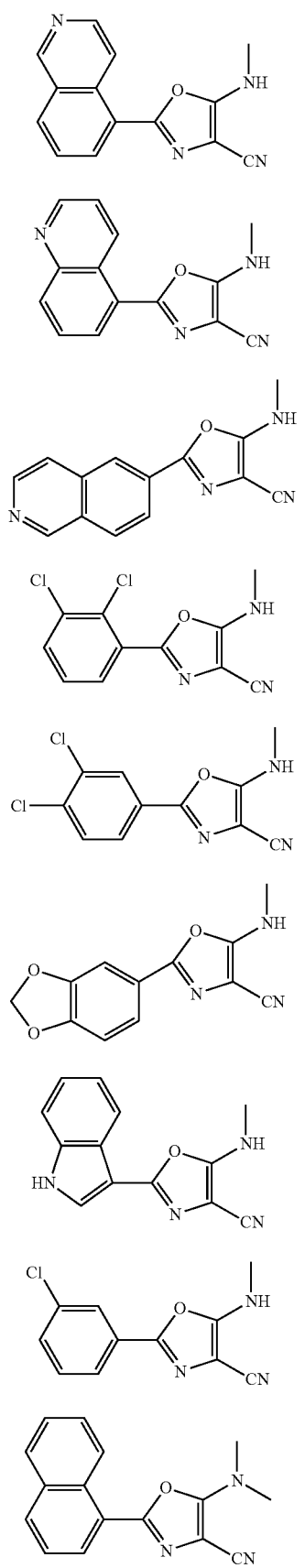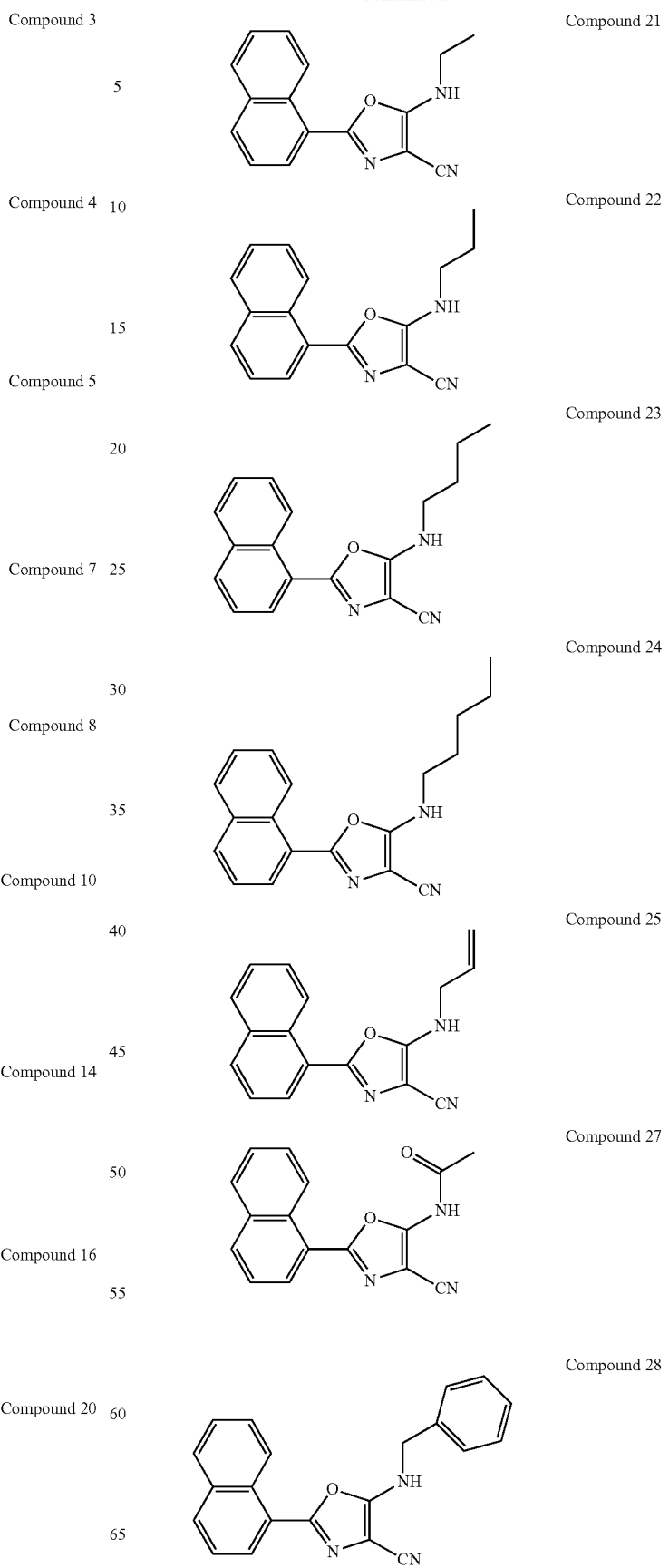

-continued

Compound 29

Compound 32

Compound 35

Compound 38

Compound 41

Compound 42

Compound 43

Compound 44

-continued

Compound 45

Compound 46

Compound 47

Compound 48

Compound 49

Compound 50

Compound 51

Compound 52

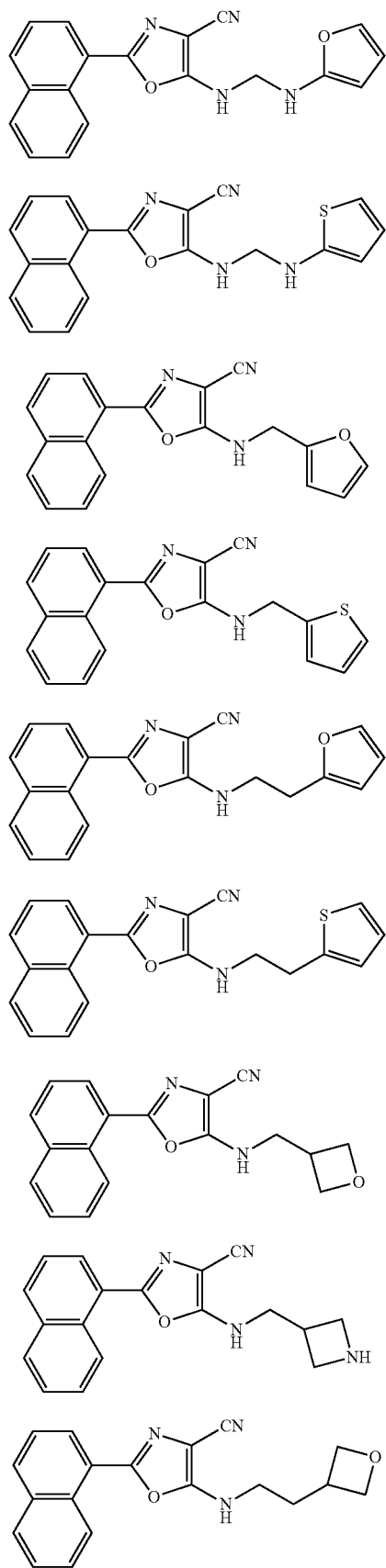

Compound 53
Compound 54
Compound 55
Compound 56
Compound 57
Compound 58
Compound 59
Compound 60
Compound 61

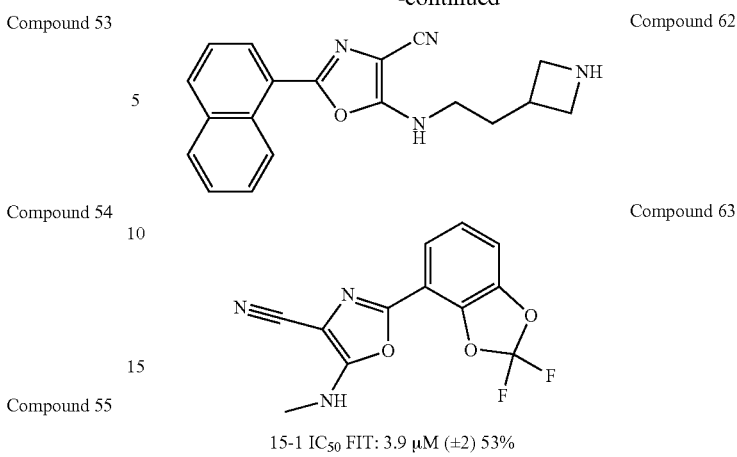

Compound 62
Compound 63

15-1 IC$_{50}$ FIT: 3.9 μM (±2) 53%

Compounds of Formula I, II, or III are either commercially available or can be synthesized by methods well known to one of skill in the chemical arts. Exemplary methods to synthesize compound 1 and other compounds can be found in the Examples section.

Methods for measuring the inhibitory effect of a compound on 12/15-LOX are also well known in the art. For example, lipoxygenase UV-Vis assays can be used. The lipoxygenase UV-Vis assay can permit the determination of percent inhibition and IC$_{50}$ values. IC$_{50}$, also called the half maximal inhibitory concentration, is a measure of the effectiveness of a substance in inhibiting a specific biological or biochemical function. IC$_{50}$ values can be obtained, for example, by determining the enzymatic rate at various inhibitor concentrations and plotted against inhibitor concentration, followed by a hyperbolic saturation curve fit.

Pharmaceutical Compositions

Another aspect of the invention relates to pharmaceutical compositions comprising the compounds (i.e., 12/15-LOX inhibitors) disclosed herein. In some embodiments, the pharmaceutical composition comprises a pharmaceutically-acceptable carrier and/or diluent. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein. The amount of a 12/15-LOX inhibitor which can be combined with a carrier material to produce a single dosage form will generally be that amount of the 12/15-LOX inhibitor which produces a desired therapeutic effect. Generally out of one hundred percent, this amount will range from about 0.01% to 99% of 12/15-LOX inhibitor, such as from about 0.1% to about 70%, and from 5% to about 30%.

Additionally, the 12/15-LOX inhibitors can be delivered using lipid- or polymer-based nanoparticles. See for example Allen, T. M., Cullis, P. R. Drug delivery systems: entering the mainstream. Science. 303(5665): 1818-22 (2004).

In some embodiments, the pharmaceutical compositions further comprise an agent (e.g., a vehicle) that facilitates crossing the blood-brain barrier by the 12/15-LOX inhibitors.

The pharmaceutical compositions of the present invention can be specially formulated for administration in solid, liquid or gel form, including those adapted for the following: (1) oral administration, for example, drenches (aqueous or non-aqueous solutions or suspensions), lozenges, dragees, capsules, pills, tablets (e.g., those targeted for buccal, sublingual, and systemic absorption), boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) transmucosally; or (9) nasally. Additionally the compounds described herein can be implanted into a patient or injected using a drug delivery system. See, for example, Urquhart, et al., Ann. Rev. Pharmacol. Toxicol. 24: 199-236 (1984); Lewis, ed. "Controlled Release of Pesticides and Pharmaceuticals" (Plenum Press, New York, 1981); U.S. Pat. No. 3,773,919; and U.S. Pat. No. 3,270,960. Examples of dosage forms include, but are not limited to: tablets; caplets; capsules, such as hard gelatin capsules and soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquids such as suspensions (e.g., aqueous or non-aqueous liquid suspensions, oil-in-water emulsions, or water-in-oil liquid emulsions), solutions, and elixirs; and sterile solids (e.g., crystalline or amorphous solids) that can be reconstituted to provide liquid dosage forms.

Aerosol Formulations.

12/15-LOX inhibitors can be administered directly to the airways in the form of an aerosol or by nebulization. For use as aerosols, 12/15-LOX inhibitors in solution or suspension may be packaged in a pressurized aerosol container together with suitable propellants, for example, hydrocarbon propellants like propane, butane, or isobutane with conventional adjuvants. The 12/15-LOX inhibitors can also be administered in a non-pressurized form such as in a nebulizer or atomizer.

The term "nebulization" is well known in the art to include reducing liquid to a fine spray. Preferably, by such nebulization small liquid droplets of uniform size are produced from a larger body of liquid in a controlled manner. Nebulization can be achieved by any suitable means therefor, including by using many nebulizers known and marketed today. For example, an AEROMIST pneumatic nebulizer is available from Inhalation Plastic, Inc. of Niles, Ill.

As is well known, any suitable gas can be used to apply pressure during the nebulization, with preferred gases to date being those which are chemically inert to the 12/15-LOX inhibitors. Exemplary gases including, but are not limited to, nitrogen, argon or helium can be used to high advantage.

12/15-LOX inhibitors can also be administered directly to the airways in the form of a dry powder. For use as a dry powder, 12/15-LOX inhibitors can be administered by use of an inhaler. Exemplary inhalers include metered dose inhalers and dry powdered inhalers. A metered dose inhaler or "MDI" is a pressure resistant canister or container filled with a product such as a pharmaceutical composition dissolved in a liquefied propellant or micronized particles suspended in a liquefied propellant. The correct dosage of the composition is delivered to the patient. A dry powder inhaler is a system operable with a source of pressurized air to produce dry powder particles of a pharmaceutical composition that is compacted into a very small volume.

Dry powder aerosols for inhalation therapy are generally produced with mean diameters primarily in the range of <5 µm. As the diameter of particles exceeds 3 µm, there is increasingly less phagocytosis by macrophages. However, increasing the particle size also has been found to minimize the probability of particles (possessing standard mass density) entering the airways and acini due to excessive deposition in the oropharyngeal or nasal regions.

Suitable powder compositions include, by way of illustration, powdered preparations of 12/15-LOX inhibitors thoroughly intermixed with lactose, or other inert powders acceptable for intrabronchial administration. The powder compositions can be administered via an aerosol dispenser or encased in a breakable capsule which may be inserted by the patient into a device that punctures the capsule and blows the powder out in a steady stream suitable for inhalation. The compositions can include propellants, surfactants, and co-solvents and may be filled into conventional aerosol containers that are closed by a suitable metering valve.

Aerosols for the delivery to the respiratory tract are known in the art. See for example, Adjei, A. and Garren, J. Pharm. Res., 1: 565-569 (1990); Zanen, P. and Lamm, J.-W. J. Int. J. Pharm., 114: 111-115 (1995); Gonda, I. "Aerosols for delivery of therapeutic and diagnostic agents to the respiratory tract," in Critical Reviews in Therapeutic Drug Carrier Systems, 6:273-313 (1990); Anderson et al., Am. Rev. Respir. Dis., 140: 1317-1324 (1989)) and have potential for the systemic delivery of peptides and proteins as well (Patton and Platz, Advanced Drug Delivery Reviews, 8:179-196 (1992)); Timsina et. al., Int. J. Pharm., 101: 1-13 (1995); and Tansey, I. P., Spray Technol. Market, 4:26-29 (1994); French, D. L., Edwards, D. A. and Niven, R. W., Aerosol Sci., 27: 769-783 (1996); Visser, J., Powder Technology 58: 1-10 (1989)); Rudt, S. and R. H. Muller, J. Controlled Release, 22: 263-272 (1992); Tabata, Y, and Y. Ikada, Biomed. Mater. Res., 22: 837-858 (1988); Wall, D. A., Drug Delivery, 2: 10 1-20 1995); Patton, J. and Platz, R., Adv. Drug Del. Rev., 8: 179-196 (1992); Bryon, P., Adv. Drug. Del. Rev., 5: 107-132 (1990); Patton, J. S., et al., Controlled Release, 28: 15 79-85 (1994); Damms, B. and Bains, W., Nature Biotechnology (1996); Niven, R. W., et al., Pharm. Res., 12(9); 1343-1349 (1995); and Kobayashi, S., et al., Pharm. Res., 13(1): 80-83 (1996), contents of all of which are herein incorporated by reference in their entirety.

Oral Formulations.

Pharmaceutical compositions comprising 12/15-LOX inhibitors of the present invention can also be formulated into oral dosage forms such as, but not limited to, tablets (including without limitation scored or coated tablets), pills, caplets, capsules, chewable tablets, powder packets, cachets, troches, wafers, aerosol sprays, or liquids, such as but not limited to, syrups, elixirs, solutions or suspensions in an aqueous liquid, a non-aqueous liquid, an oil-in-water emulsion, or a water-in-oil emulsion. Such compositions contain a predetermined amount of the pharmaceutically acceptable salt of the disclosed compounds, and may be prepared by methods of pharmacy well known to those skilled in the art. See generally, Remington's Pharmaceutical Sciences, 18th ed., Mack Publishing, Easton, Pa. (1990).

Typical oral dosage forms are prepared by combining the pharmaceutically acceptable salt of the disclosed compounds in an intimate admixture with at least one excipient according to conventional pharmaceutical compounding techniques. Excipients can take a wide variety of forms depending on the form of the composition desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, microcrystalline cellulose, kaolin, diluents, granulating agents, lubricants, binders, and disintegrating agents. Due to their ease of administration, tablets and capsules represent the most advantageous solid oral dosage unit forms, in which case solid pharmaceutical excipients are used. If desired, tablets can be coated by standard aqueous or nonaqueous techniques. These dosage forms can be prepared by any of the methods of pharmacy. In general, pharmaceutical compositions and dosage forms are prepared by uniformly and intimately admixing the active ingredient(s) with liquid carriers, finely divided solid carriers, or both, and then shaping the product into the desired presentation if necessary.

For example, a tablet can be prepared by compression or molding. Compressed tablets can be prepared by compressing in a suitable machine the active ingredient(s) in a free-flowing form, such as a powder or granules, optionally mixed with one or more excipients. Molded tablets can be made by molding in a suitable machine a mixture of the powdered compound moistened with an inert liquid diluent. Examples of excipients that can be used in oral dosage forms of the disclosure include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Suitable forms of microcrystalline cellulose include, but are not limited to, the materials sold as AVICEL-PH-101, AVICEL-PH-103 AVICEL RC-581, and AVICEL-PH-105 (available from FMC Corporation, American Viscose Division, Avicel Sales, Marcus Hook, Pa., U.S.A.), and mixtures thereof. An exemplary suitable binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions of the disclosure is typically present in from about 50 to about 99 weight percent of the pharmaceutical composition or dosage form.

Disintegrants are used in the compositions of the disclosure to provide tablets that disintegrate when exposed to an aqueous environment. Tablets that contain too much disintegrant may swell, crack, or disintegrate in storage, while those that contain too little may be insufficient for disintegration to occur and may thus alter the rate and extent of release of the active ingredient(s) from the dosage form. Thus, a sufficient amount of disintegrant that is neither too little nor too much to detrimentally alter the release of the active ingredient(s) should be used to form solid oral dosage forms of the disclosure. The amount of disintegrant used varies based upon the type of formulation and mode of administration, and is readily discernible to those of ordinary skill in the art. Typical pharmaceutical compositions comprise from about 0.5 to about 15 weight percent of disintegrant, preferably from about 1 to about 5 weight percent of disintegrant.

Disintegrants that can be used to form pharmaceutical compositions and dosage forms of the disclosure include, but are not limited to, agar, alginic acid, calcium carbonate, microcrystalline cellulose, croscarmellose sodium, crospovidone, polacrilin potassium, sodium starch glycolate, potato or tapioca starch, other starches, pre-gelatinized starch, clays, other algins, other celluloses, gums, and mixtures thereof.

Lubricants that can be used to form pharmaceutical compositions and dosage forms of the disclosure include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL® 200, manufactured by W. R. Grace Co. of Baltimore, Md.), a coagulated aerosol of synthetic silica (marketed by Degussa Co. of Piano, Tex.), CAB-O-SIL® (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

This disclosure further encompasses anhydrous pharmaceutical compositions and dosage forms comprising the disclosed compounds as active ingredients, since water can facilitate the degradation of some compounds. For example, the addition of water (e.g., 5%) is widely accepted in the pharmaceutical arts as a means of simulating long-term storage in order to determine characteristics such as shelf life or the stability of formulations over time. See, e.g., Jens T. Carstensen, Drug Stability: Principles & Practice, 379-80 (2nd ed., Marcel Dekker, NY, N.Y.: 1995). Water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms of the disclosure can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials) with or without desiccants, blister packs, and strip packs.

Controlled and Delayed Release Formulations.

12/15-LOX inhibitors can be administered by controlled- or delayed-release means. Controlled-release pharmaceutical products have a common goal of improving drug therapy over that achieved by their non-controlled release counterparts. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. Kim, Cherng-ju, Controlled Release Dosage Form Design, 2 (Technomic Publishing, Lancaster, Pa.: 2000).

Conventional dosage forms generally provide rapid or immediate drug release from the formulation. Depending on the pharmacology and pharmacokinetics of the drug, use of conventional dosage forms can lead to wide fluctuations in the concentrations of the drug in a patient's blood and other tissues. These fluctuations can impact a number of parameters, such as dose frequency, onset of action, duration of efficacy, maintenance of therapeutic blood levels, toxicity, side effects, and the like. Advantageously, controlled-release formulations can be used to control a drug's onset of action, duration of action, plasma levels within the therapeutic window, and peak blood levels. In particular, controlled- or extended-release dosage forms or formulations can be used to ensure that the maximum effectiveness of a drug is achieved while minimizing potential adverse effects and safety concerns, which can occur both from under-dosing a drug (i.e., going below the minimum therapeutic levels) as well as exceeding the toxicity level for the drug.

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, ionic strength, osmotic pressure, temperature, enzymes, water, and other physiological conditions or compounds.

A variety of known controlled- or extended-release dosage forms, formulations, and devices can be adapted for use with the salts and compositions of the disclosure. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185 B1; each of which is incorporated herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), multilayer coatings, microparticles, liposomes, or microspheres or a combination thereof to provide the desired release profile in varying proportions. Additionally, ion exchange materials can be used to prepare immobilized, adsorbed salt forms of the disclosed compounds and thus effect controlled delivery of the drug. Examples of specific anion exchangers include, but are not limited to, Duolite® A568 and Duolite® AP143 (Rohm&Haas, Spring House, Pa. USA).

One embodiment of the disclosure encompasses a unit dosage form that includes a pharmaceutically acceptable salt of the disclosed compounds (e.g., a sodium, potassium, or lithium salt), or a polymorph, solvate, hydrate, dehydrate, co-crystal, anhydrous, or amorphous form thereof, and one or more pharmaceutically acceptable excipients or diluents, wherein the pharmaceutical composition or dosage form is formulated for controlled-release. Specific dosage forms utilize an osmotic drug delivery system.

A particular and well-known osmotic drug delivery system is referred to as OROS® (Alza Corporation, Mountain View, Calif. USA). This technology can readily be adapted for the delivery of compounds and compositions of the disclosure. Various aspects of the technology are disclosed in U.S. Pat. Nos. 6,375,978 B1; 6,368,626 B1; 6,342,249 B1; 6,333,050 B2; 6,287,295 B1; 6,283,953 B1; 6,270,787 B1; 6,245,357 B1; and 6,132,420; each of which is incorporated herein by reference. Specific adaptations of OROS® that can be used to administer compounds and compositions of the disclosure include, but are not limited to, the OROS® Push-Pull™, Delayed Push-Pull™, Multi-Layer Push-Pull™, and Push-Stick™ Systems, all of which are well known. See, e.g. worldwide website alza.com. Additional OROS® systems that can be used for the controlled oral delivery of compounds and compositions of the disclosure include OROS®-CT and L-OROS®; see, Delivery Times, vol. 11, issue II (Alza Corporation).

Conventional OROS® oral dosage forms are made by compressing a drug powder (e.g., a 12/15-LOX inhibitor salt) into a hard tablet, coating the tablet with cellulose derivatives to form a semi-permeable membrane, and then drilling an orifice in the coating (e.g., with a laser). Kim, Cherng-ju, Controlled Release Dosage Form Design, 231-238 (Technomic Publishing, Lancaster, Pa.: 2000). The advantage of such dosage forms is that the delivery rate of the drug is not influenced by physiological or experimental conditions. Even a drug with a pH-dependent solubility can be delivered at a constant rate regardless of the pH of the delivery medium. But because these advantages are provided by a build-up of osmotic pressure within the dosage form after administration, conventional OROS® drug delivery systems cannot be used to effectively delivery drugs with low water solubility.

In some embodiments, the 12/15-LOX inhibitor is administered to a subject by sustained release or in pulses. Pulse therapy is not a form of discontinuous administration of the same amount of a composition over time, but comprises administration of the same dose of the composition at a reduced frequency or administration of reduced doses. Sustained release or pulse administration are particularly preferred when the angiogenesis is associated with tumor growth as it leads to regression of blood vessels feeding the tumor and ultimately to regression of the tumor itself. Each pulse dose can be reduced and the total amount of drug administered over the course of treatment to the patient is minimized.

The number of pulses in a single therapeutic regimen may be as little as two, but is typically from about 5 to 10, 10 to 20, 15 to 30 or more. In fact, patients can receive drugs for life according to the methods of this invention without the problems and inconveniences associated with current therapies. Compositions can be administered by most any means, but are preferable delivered to the patient as an injection (e.g. intravenous, subcutaneous, intraarterial), infusion or instillation. Various methods and apparatus for pulsing compositions by infusion or other forms of delivery to the patient are disclosed in U.S. Pat. Nos. 4,747,825; 4,723,958; 4,948,592; 4,965,251 and 5,403,590.

Parenteral Formulations.

Parenteral dosage forms can be administered to patients by various routes, including, but not limited to, subcutaneous, intravenous (including bolus injection), intramuscular, and intraarterial. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. In addition, controlled-release parenteral dosage forms can be prepared for administration of a patient, including, but not limited to, administration DUROS®-type dosage forms, and dose-dumping.

Suitable vehicles that can be used to provide parenteral dosage forms of the disclosure are well known to those skilled in the art. Examples include, without limitation: sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate.

Compounds that alter or modify the solubility of a pharmaceutically acceptable salt of a 12/15-LOX inhibitor disclosed herein can also be incorporated into the parenteral dosage forms of the disclosure, including conventional and controlled-release parenteral dosage forms.

Topical, Transdermal, and Mucosal Formulations.

Topical dosage forms of the disclosure include, but are not limited to, creams, lotions, ointments, gels, shampoos, sprays, aerosols, solutions, emulsions, and other forms known to one of skill in the art. See, e.g., Remington's Pharmaceutical Sciences, 18th ed., Mack Publishing, Easton, Pa. (1990); and Introduction to Pharmaceutical Dosage Forms, 4th ed., Lea & Febiger, Philadelphia, Pa. (1985). For non-sprayable topical dosage forms, viscous to semi-solid or solid forms comprising a carrier or one or more excipients compatible with topical application and having a dynamic viscosity preferably greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, preferably in combination with a solid or liquid inert carrier, is packaged in a mixture with a pressurized volatile (e.g., a gaseous propellant, such as freon), or in a squeeze bottle. Moisturizers or humectants can also be added to pharmaceutical compositions and dosage forms if desired. Examples of such additional ingredients are well known in the art. See, e.g., Remington's Pharmaceutical Sciences, 18.sup.th Ed., Mack Publishing, Easton, Pa. (1990).

Transdermal and mucosal dosage forms of the 12/15-LOX inhibitor compositions of the disclosure include, but are not limited to, ophthalmic solutions, patches, sprays, aerosols, creams, lotions, suppositories, ointments, gels, solutions, emulsions, suspensions, or other forms known to one of skill in the art. Dosage forms suitable for treating mucosal tissues within the oral cavity can be formulated as mouthwashes, as oral gels, or as buccal patches. Additional transdermal dosage forms include "reservoir type" or "matrix type" patches, which can be applied to the skin and worn for a specific period of time to permit the penetration of a desired amount of active ingredient.

Examples of transdermal dosage forms and methods of administration that can be used to administer the active ingredient(s) of the disclosure include, but are not limited to, those disclosed in U.S. Pat. Nos. 4,624,665; 4,655,767; 4,687,481; 4,797,284; 4,810,499; 4,834,978; 4,877,618; 4,880,633; 4,917,895; 4,927,687; 4,956,171; 5,035,894; 5,091,186; 5,163,899; 5,232,702; 5,234,690; 5,273,755; 5,273,756; 5,308,625; 5,356,632; 5,358,715; 5,372,579; 5,421,816; 5,466,465; 5,494,680; 5,505,958; 5,554,381; 5,560,922; 5,585,111; 5,656,285; 5,667,798; 5,698,217; 5,741,511; 5,747,783; 5,770,219; 5,814,599; 5,817,332; 5,833,647; 5,879,322; and 5,906,830, each of which are incorporated herein by reference in their entirety.

Suitable excipients (e.g., carriers and diluents) and other materials that can be used to provide transdermal and mucosal dosage forms encompassed by this disclosure are well known to those skilled in the pharmaceutical arts, and depend on the particular tissue or organ to which a given pharmaceutical composition or dosage form will be applied. With that fact in mind, typical excipients include, but are not limited to water, acetone, ethanol, ethylene glycol, propylene glycol, butane-1,3-diol, isopropyl myristate, isopropyl palmitate, mineral oil, and mixtures thereof, to form dosage forms that are non-toxic and pharmaceutically acceptable.

Depending on the specific tissue to be treated, additional components may be used prior to, in conjunction with, or subsequent to treatment with a 12/15-LOX inhibitor of the disclosure. For example, penetration enhancers can be used to assist in delivering the active ingredients to or across the tissue. Suitable penetration enhancers include, but are not limited to: acetone; various alcohols such as ethanol, oleyl, an tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as TWEEN 80 (polysorbate 80) and SPAN 60 (sorbitan monostearate).

The pH of a pharmaceutical composition or dosage form, or of the tissue to which the pharmaceutical composition or dosage form is applied, may also be adjusted to improve delivery of the active ingredient(s). Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of the active ingredient(s) so as to improve delivery. In this regard, stearates can serve as a lipid vehicle for the formulation, as an emulsifying agent or surfactant, and as a delivery-enhancing or penetration-enhancing agent. Different hydrates, dehydrates, co-crystals, solvates, polymorphs, anhydrous, or amorphous forms of the pharmaceutically acceptable salt of a 12/15-LOX inhibitor can be used to further adjust the properties of the resulting composition.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized.

The therapeutically effective dose can be estimated initially from cell culture assays. A dose may be formulated in animal models to achieve a circulating plasma concentration range that includes the IC50 (i.e., the concentration of the therapeutic which achieves a half-maximal inhibition of symptoms) as determined in cell culture. Levels in plasma may be measured, for example, by high performance liquid chromatography. The effects of any particular dosage can be monitored by a suitable bioassay.

The dosage can be determined by one of skill in the art and can also be adjusted by the individual physician in the event of any complication. Typically, the dosage of a composition comprising a 12/15-LOX inhibitor disclosed herein can range from 0.001 mg/kg body weight to 5 g/kg body weight. In some embodiments, the dosage range is from 0.001 mg/kg body weight to 1 g/kg body weight, from 0.001 mg/kg body weight to 0.5 g/kg body weight, from 0.001 mg/kg body weight to 0.1 g/kg body weight, from 0.001 mg/kg body weight to 50 mg/kg body weight, from 0.001 mg/kg body weight to 25 mg/kg body weight, from 0.001 mg/kg body weight to 10 mg/kg body weight, from 0.001 mg/kg body weight to 5 mg/kg body weight, from 0.001 mg/kg body weight to 1 mg/kg body weight, from 0.001 mg/kg body weight to 0.1 mg/kg body weight, or from 0.001 mg/kg body weight to 0.005 mg/kg body weight. Alternatively, in some embodiments the dosage range is from 0.1 g/kg body weight to 5 g/kg body weight, from 0.5 g/kg body weight to 5 g/kg body weight, from 1 g/kg body weight to 5 g/kg body weight, from 1.5 g/kg body weight to 5 g/kg body weight, from 2 g/kg body weight to 5 g/kg body weight, from 2.5 g/kg body weight to 5 g/kg body weight, from 3 g/kg body weight to 5 g/kg body weight, from 3.5 g/kg body weight to 5 g/kg body weight, from 4 g/kg body weight to 5 g/kg body weight, or from 4.5 g/kg body weight to 5 g/kg body weight. Effective doses may be extrapolated from dose-response curves derived from in vitro or animal model test bioassays or systems. The dosage should not be so large as to cause unacceptable adverse side effects.

In some embodiments, the dosage of a composition comprising a 12/15-LOX inhibitor disclosed herein can be administered in a dose of from about 20 mg/m$^2$ to about 5,000 mg/m$^2$ body surface area. For example, the dose can be from about 20 mg/m$^2$ to about 200 mg/m$^2$ body surface area; the dose can be from about 150 mg/m$^2$ to about 500 mg/m$^2$ body surface area; the dose can be from about 400 mg/m$^2$ to about 1000 mg/m$^2$ body surface area; the dose can be from about 900 mg/m$^2$ to about 5,000 mg/m$^2$ body surface area; the dose can be from about 200 mg/m$^2$ to about 1,000 mg/m$^2$ body surface area; or the dose can be from about 500 mg/m$^2$ to about 600 mg/m$^2$ body surface area.

Treatment

Another aspect of the invention relates to the use of the compounds or compositions disclosed herein for the treatment of a condition involving 12/15-LOX. As used herein, the term "condition(s) involving 12/15-LOX" refers to any condition having 12/15-LOX as a cause of the condition, or a condition that can be worsened by the activity of 12/15-LOX, or a condition the progression of which is linked to the activity of 12/15-LOX. A condition involving 12/15-LOX can therefore benefit therapeutically by inhibiting 12/15-LOX.

A method is provided herein for treating a condition involving 12/15-lipoxygenase in a subject, the method comprising administering to the subject an effective amount of a 12/15-LOX inhibitor disclosed herein. In methods of treatment described herein, the administration of 12/15-LOX inhibitor can be for either "prophylactic" or "therapeutic" purpose. When provided prophylactically, the 12/15-LOX inhibitor is provided in advance of any symptom. When provided therapeutically, the 12/15-LOX inhibitor is provided at (or after) the onset of a symptom or indication of a condition involving 12/15-LOX. For example, stroke symptoms can include, but are not limited to, sudden numbness, tingling, weakness, or loss of movement in the face, arm, or leg, especially on only one side of the body; sudden vision changes; sudden trouble speaking; sudden confusion or trouble understanding simple statements; sudden problems with walking or balance; a sudden, severe headache that is different from past headaches.

12/15-LOX is an enzyme that is involved in several important diseases and conditions such as strokes, atherosclerosis, diabetes, obesity, asthma, glomerulonephritis, osteoporosis, and Alzheimer's. 12/15-LOX has recently been implicated in the disease of the newborn periventricular leukomalacia, as well as in breast cancer growth. 12/15-LOX has also been found to increase in mouse models of cardiac arrest with resuscitation, and mice in which the gene encoding 12/15-LOX has been deleted, are protected against brain injury in these mouse models. Examples of conditions involving 12/15-LOX also include, but are not limited to, diseases involving apoptosis in cancer cells such as prostatic cancer, gastric cancer, breast cancer, pancreatic cancer, colorectal or esophageal cancer and airways carcinoma; diseases involving hypoxia, or anoxia such as atherosclerosis, myocardial infarction, cardiovascular disease, heart failure (including chronic and congestive heart failure), cerebral ischemia, retinal ischemia, myocardial ischemia, post-surgical cognitive dysfunction and other ischemias; diseases involving inflammation, including diabetes, arterial inflammation, inflammatory bowel disease, Crohn's disease, renal disease, pre-menstrual syndrome, asthma, allergic rhinitis, gout; cardiopulmonary inflammation, rheumatoid arthritis, osteoarthritis, muscle fatigue and inflammatory disorders of the skin including acne, dermatitis and psoriasis; disorders of the airways such as asthma, chronic bronchitis, human airway carcinomas, mucus hypersecretion, chronic obstructive pulmonary disease (COPD), pulmonary fibrosis caused by chemotherapy or other drugs, idiopathic pulmonary fibrosis, cystic fibrosis, and adult respiratory distress syndrome; diseases involving central nervous system (CNS) disorders including psychiatric disorders including anxiety and depression; neurodegeneration and neuroinflammation including Alzheimer's, dementia and Parkinson's disease; peripheral neuropathy including spinal chord injury, head injury and surgical trauma, and allograft tissue and organ transplant rejection; diseases involving the autoimmune system such as psoriasis, eczema, rheumatoid arthritis, and diabetes; and disorders involving bone loss or bone formation.

A suitable 12/15-LOX inhibitor can have an IC50 of less than 50 µM, e.g., a suitable 12/15-LOX inhibitor can have an IC50 of from about 50 µM to about 5 nM, or less than 5 nM. For example, in some embodiments, a suitable 12/15-LOX inhibitor has an IC50 of from about 50 µM to about 25 µM, from about 25 µM to about 10 µM, from about 10 µM to about 5 µM, from about 5 µM to about 1 µM, from about 1 µM to about 500 nM, from about 500 nM to about 400 nM, from about 400 nM to about 300 nM, from about 300 nM to about 250 nM, from about 250 nM to about 200 nM, from about 200 nM to about 150 nM, from about 150 nM to about 100 nM, from about 100 nM to about 50 nM, from about 50 nM to about 30 nM, from about 30 nM to about 25 nM, from about 25 nM to about 20 nM, from about 20 nM to about 15 nM, from about 15 nM to about 10 nM, from about 10 nM to about 5 nM, or less than about 5 nM.

The 12/15-LOX inhibitors of the present invention can also be used in applications known to benefit from the inhibition of 12/15-LOX. Non-limiting examples of these applications are disclosed in, US20060193797, US20120053220, US20060106014, US20060079488, U.S. Pat. No. 7,576,094, US20130131140, US2005070589, US20080207588, US2005065198, and U.S. Pat. No. 8,048,900, the contents of each of which are incorporated by reference in its entirety.

With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment or make other alteration to treatment regimen. The dosing schedule can vary from once a week to daily depending on a number of clinical factors, such as the subject's sensitivity to the drug. The desired dose can be administered at one time or divided into subdoses, e.g., 2-4 subdoses and administered over a period of time, e.g., at appropriate intervals through the day or other appropriate schedule. Such sub-doses can be administered as unit dosage forms. In some embodiments, administration is chronic, e.g., one or more doses daily over a period of weeks or months. Examples of dosing schedules are administration daily, twice daily, three times daily or four or more times daily over a period of 1 week, 2 weeks, 3 weeks, 4 weeks, 1 month, 2 months, 3 months, 4 months, 5 months, or 6 months or more.

Figures 5A, 5B:
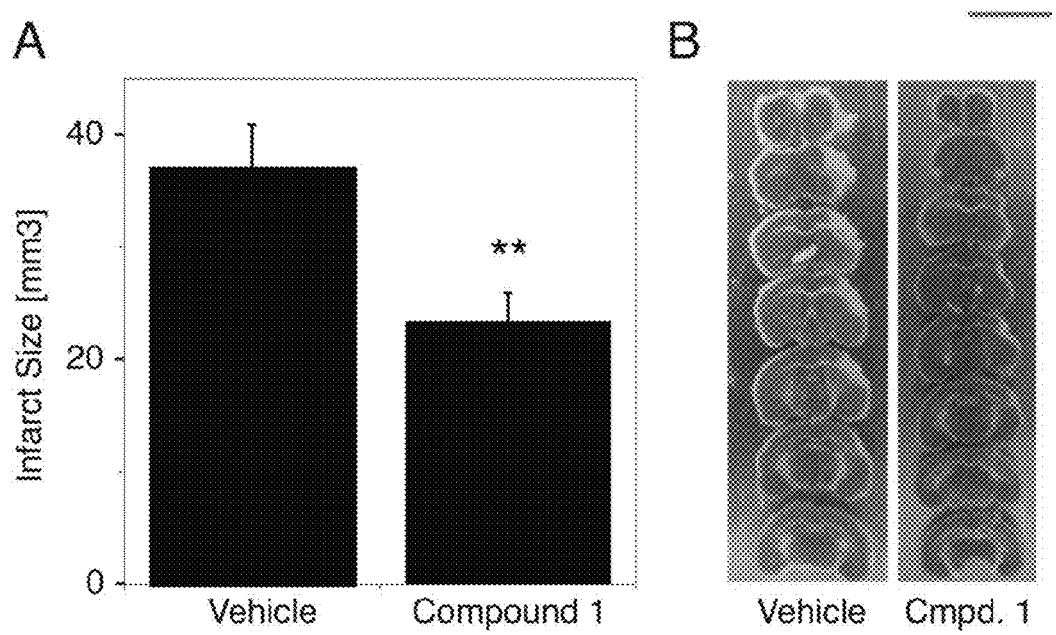
FIG. 5A is a plot showing activity of compound 1 (50 mg/kg) administered via intraperitoneal (IP) injection in mouse distal MCAO model of permanent focal ischemia (**p<0.01).
FIG. 5B is a set of images showing typical examples of sequential (top to bottom represents front to back sections of a single brain) TTC-stained brain sections from vehicle- and Compound 1-treated mice. The white areas in the cortex (top right) indicate non-viable infarcted tissue.
Figure 6A:
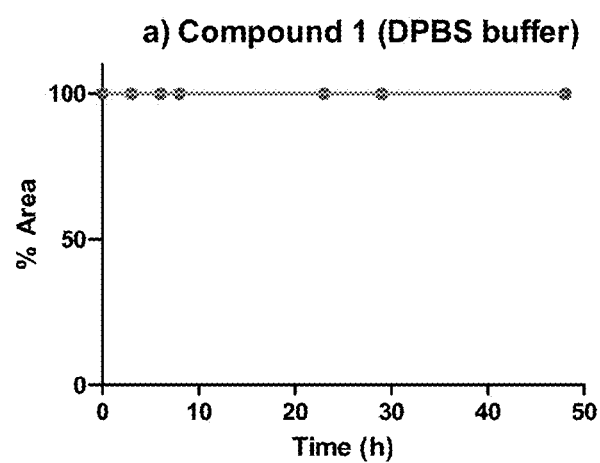
FIGS. 6A-6D are plots showing stability of 1 measured as percent composition of probe molecule in aqueous solution (contains 20% acetonitrile) at r.t. over 48 hr in (FIG. 6A) DPBS buffer (pH 7.4), (FIG. 6B) Lipoxygenase UV-Vis assay buffer (1M HEPES buffer, pH 7.3), (FIG. 6C) pH 2 buffer, and (FIG. 6D) pH 10 buffer.
Figure 6B:
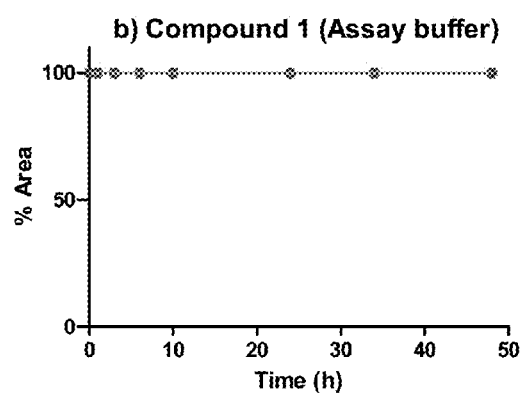
Figure 6C:
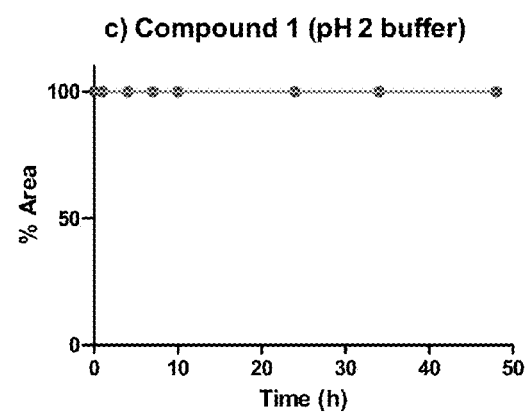
Figure 6D:
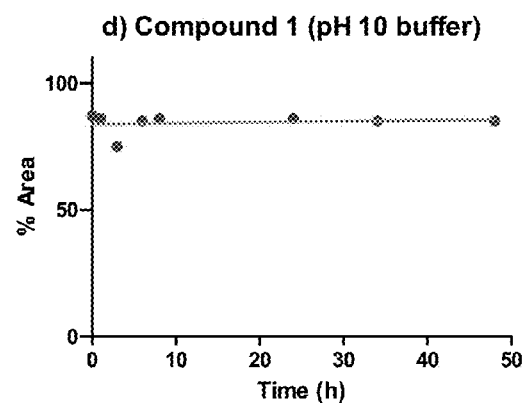

In some embodiments, the method is provided herein for treating a stroke in a subject using the 12/15-LOX inhibitors disclosed herein. For example, FIG. 5B shows that ML351 significantly reduces infarct size in a mouse model of permanent focal ischemia. Strokes are sudden neurological disorders that occur when blood flow to the brain is disturbed. There are two kinds of strokes. One is called acute ischemic stroke (AIS), which is due to blood flow blockage, and it accounts for 87% of strokes. AIS is an episode of neurological dysfunction caused by focal brain, spinal cord, or retina ischemia with evidence of acute infarction (Easton et al., Stroke 2009, 40, 2276-2293). There are at least four different causes of blood flow interruption: (1) a blood clot in a blood vessel; (2) a blood clot in the dural venous sinuses, which drain blood from the brain; (3) an embolus clogging a blood vessel; or (4) a sudden drop in blood pressure. Stroke symptoms can and frequently do persist beyond 24 hours if the patient survives the initial damage. The other kind of strokes is called hemorrhagic stroke, which is caused by a weakened blood vessel that ruptures and bleeds into the surrounding brain tissue. A transient ischemic attack (TIA) is a condition mimicking AIS, in which a temporary interruption in blood flow to part of the brain results in impaired brain functions, but does not necessarily result in brain tissue damage.

Without wishing to be bound by theory, because oxidative stress is a major neurodegenerative process in ischemic diseases such as stroke, a role for 12/15-LOX in stroke-induced brain injury seemed reasonable and indeed, was found. Later work showed that 12/15-LOX was detrimental not just to neurons, but also to the brain vasculature after stroke, via a mechanism that involves an intracellular attack on mitochondria and translocation of the apoptosis-inducing factor (AIF) to the nucleus. Recent studies have shown that 12/15-LOX is also increased in human stroke (Yigitkanli et al., Ann. Neurol. 2013, 73, 129-135). In line with these findings, several LOX inhibitors have been found to reduce infarct size, leakage of the blood brain barrier and edema formation, and even hemorrhagic transformation following infusion of tPA.

Diagnostic methods for strokes include, but are not limited to, neuroimaging (e.g., magnetic resonance imaging (MM), computerized tomography (CT), diffuse optical imaging, event-related optical signal, functional MM, magnetoencephalography, positron emission tomography, or single-photon emission computed tomography), medical history, and physical exam.

In some embodiments, the 12/15-LOX inhibitors disclosed herein can be used in combination with other therapies to treat a stroke. An ischemic stroke can be treated by administering an antithrombotic agent to dissolve the blood clot. Antithrombotic agents are further divided into the following three subtypes: anticoagulants, antiplatelet drugs, and thrombolytic drugs. Non-limiting examples of anticoagulants include: coumarins, heparin, warfarin, acenocoumarol, phenprocoumon, atromentin, phenindione, fondaparinux, idraparinux, direct factor Xa inhibitors, direct thrombin inhibitors, antithrombin protein therapeutics, batroxobin, and hementin. Non-limiting examples of antiplatelet drugs include: irreversible cyclooxygenase inhibitors (e.g., aspirin or triflusal), adenosine diphosphate receptor inhibitors (e.g., clopidogrel, prasugrel, ticagrelor, or ticlopidine), phosphodiesterase inhibitors (e.g., cilostazol), glycoprotein IIB/IIIA inhibitors (e.g., abciximab, eptifibatide, or tirofiban), adenosine reuptake inhibitors (e.g., dipyridamole), and thromboxane inhibitors (e.g., thromboxane synthase inhibitors or thromboxane receptor antagonists). Non-limiting examples of thrombolytic drugs include: tissue plasminogen activator t-PA (e.g., alteplase, reteplase, or tenecteplase), anistreplase, streptokinase, and urokinase. An ischemic stroke can also be treated by endovascular procedures, in which a catheter is sent to the blood flow blockage site to remove the blood clot. t-PA can be optionally administered during the endovascular procedures.

In some embodiments, the 12/15-LOX inhibitors disclosed herein can be used to treat a stroke with hemorrhagic transformation. Hemorrhagic transformation refers to hemorrhages that develop inside areas of ischemia. For example, a subject who is on an oral anticoagulant and experience a stroke, can be treated with the 12/15-LOX inhibitors disclosed herein. In some embodiments, the 12/15-LOX inhibitors disclosed herein can be administered as adjuvant to tPA.

For the treatment of strokes, the 12/15-LOX inhibitors disclosed herein can be administered during the early phase of stroke or days (e.g., 1, 2, 3, 4, 5, 6, 7, 8, 9, 10, or more) after a stroke to aid in stroke recovery.

In some embodiments, the method is provided herein for treating periventricular leukomalacia (PVL) in a subject using the 12/15-LOX inhibitors disclosed herein. PVL patients also feature increased 12/15-LOX. Periventricular leukomalacia is the most frequent cause of cerebral palsy in premature infants. This early neonatal disorder is due to the formation of single or multiple lesions of the ring of periventricular white matter, occurring during prenatal or neonatal life. Periventricular leukomalacia is responsible for the majority of motor sequelae of prematurity.

Another aspect of the invention relates to the use of the compounds described herein for the preparation of a medicament for the treatment of a condition involving 12/15-LOX.

It should be understood that this invention is not limited to the particular methodology, protocols, and reagents, etc., disclosed herein and as such may vary. The terminology used herein is for the purpose of describing particular embodiments only, and is not intended to limit the scope of the present invention, which is defined solely by the claims.

As used herein and in the claims, the singular forms include the plural reference and vice versa unless the context clearly indicates otherwise. Other than in the operating examples, or where otherwise indicated, all numbers expressing quantities of ingredients or reaction conditions used herein should be understood as modified in all instances by the term "about."

Although any known methods, devices, and materials may be used in the practice or testing of the invention, the methods, devices, and materials in this regard are disclosed herein.

Some embodiments of the invention are listed in the following paragraphs: paragraph 1. A method of treating a condition involving 12/15-lipoxygenase in a subject, the method comprising administering to the subject an effective amount of a compound of Formula I:

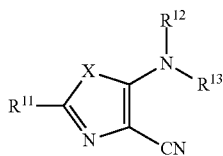

Formula I or a pharmaceutically acceptable salt thereof, wherein: X is O or S; $R^{11}$ is an aryl, heteroaryl, cyclyl, or heterocyclyl, each of which can be optionally substituted; and $R^{12}$ and $R^{13}$ are independently hydrogen, halogen, alkyl, alkenyl, alkynyl, aralkyl, acyl, aryl, heteroaryl, cyclyl or heterocyclyl, each of which can be optionally substituted.

paragraph 2. The method of paragraph 1, wherein $R^{11}$ is an aryl or heteroaryl, each of which can be optionally substituted.

paragraph 3. The method of paragraph 2, wherein $R^{11}$ is 1-naphthyl, 2-naphthyl, 6-isoquinolinyl, 2,3-dichlorophenyl, or 3,4-dichlorophenyl.

paragraph 4. The method of any of paragraphs 1-3, wherein $R^{12}$ is hydrogen, alkyl, aralkyl, acyl, aryl, or heterocyclyl, each of which can be optionally substituted.

paragraph 5. The method of paragraph 4, wherein $R^{12}$ is hydrogen, methyl, ethyl, propyl, butyl, pentyl, or phenyl.

paragraph 6. The method of any of paragraphs 1-5, wherein $R^{13}$ is hydrogen, alkyl, aralkyl, acyl, aryl, or heterocyclyl, each of which can be optionally substituted.

paragraph 7. The method of paragraph 6, wherein $R^{13}$ is hydrogen, methyl, ethyl, propyl, butyl, pentyl, or phenyl.

paragraph 8. The method of any of paragraphs 1-7, wherein $R^{12}$ is hydrogen and $R^{13}$ is hydrogen, methyl, ethyl, propyl, butyl, pentyl, or phenyl.

paragraph 9. The method of any of paragraphs 1-8, wherein X is O.

paragraph 10. The method of any of paragraphs 1-8, wherein X is S.

paragraph 11. The method of paragraph 1, wherein the compound of Formula I is of:
(i) Formula II

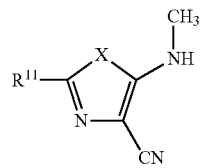

Formula II or a pharmaceutically acceptable salt thereof, wherein: X is O or S; and
$R^{11}$ is an aryl, heteroaryl, cyclyl, or heterocyclyl, each of which can be optionally substituted; or
(ii) Formula III

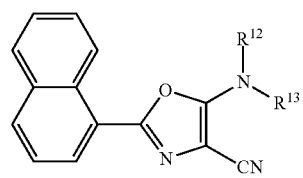

Formula III or a pharmaceutically acceptable salt thereof, wherein:
$R^{12}$ and $R^{13}$ are independently hydrogen, halogen, alkyl, alkenyl, alkynyl, aralkyl, acyl, aryl, heteroaryl, cyclyl or heterocyclyl, each of which can be optionally substituted.

paragraph 12. The method of paragraph 1, wherein the compound is selected from the group consisting of 5-(methylamino)-2-naphthalen-1-yl-1,3-oxazole-4-carbonitrile (ML351), 2-(2,3-dichlorophenyl)-5-(methylamino)-1,3-oxazole-4-carbonitrile, 2-(3,4-dichlorophenyl)-5-(methylamino)-1,3-oxazole-4-carbonitrile, 5-(methylamino)-2-naphthalen-1-yl-1,3-thiazole-4-carbonitrile.

paragraph 13. The method of paragraph 12, wherein the compound is 5-(methylamino)-2-naphthalen-1-yl-1,3-oxazole-4-carbonitrile (ML351).

paragraph 14. The method of any of paragraphs 1-13, wherein the compound inhibits 12/15-lipoxygenase.

paragraph 15. The method of any of paragraphs 1-14, wherein the condition is stroke, periventricular leukomalacia, cardiac arrest with resuscitation, atherosclerosis, Parkinson's disease, Alzheimer's disease, or breast cancer.

paragraph 16. The method of any of paragraphs 1-15, wherein the subject is a mammal.

paragraph 17. The method of any of paragraphs 1-16, wherein the subject is a human.

paragraph 18. Use of a compound of Formula I:

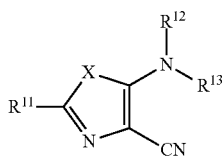

Formula I or a pharmaceutically acceptable salt thereof for the preparation of a medicament for the treatment of a condition involving 12/15-lipoxygenase, wherein:
X is O or S;
$R^{11}$ is an aryl, heteroaryl, cyclyl, or heterocyclyl, each of which can be optionally substituted; and
$R^{12}$ and $R^{13}$ are independently hydrogen, halogen, alkyl, alkenyl, alkynyl, aralkyl, acyl, aryl, heteroaryl, cyclyl or heterocyclyl, each of which can be optionally substituted.

paragraph 19. The use paragraph 18, wherein the compound of Formula I is of:
(i) Formula II:

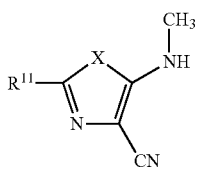

Formula II or a pharmaceutically acceptable salt thereof, wherein:
X is O or S; and
$R^{11}$ is an aryl, heteroaryl, cyclyl, or heterocyclyl, each of which can be optionally substituted; or
(ii) Formula III:

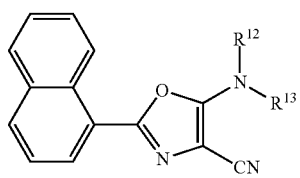

Formula III or a pharmaceutically acceptable salt thereof, wherein:
$R^{12}$ and $R^{13}$ are independently hydrogen, halogen, alkyl, alkenyl, alkynyl, aralkyl, acyl, aryl, heteroaryl, cyclyl or heterocyclyl, each of which can be optionally substituted.

paragraph 20. The use of paragraph 18 or 19, wherein the compound is selected from the group consisting of 5-(methylamino)-2-naphthalen-1-yl-1,3-oxazole-4-carbonitrile (ML351), 2-(2,3-dichlorophenyl)-5-(methylamino)-1,3-oxazole-4-carbonitrile, 2-(3,4-dichlorophenyl)-5-(methylamino)-1,3-oxazole-4-carbonitrile, and 5-(methylamino)-2-naphthalen-1-yl-1,3-thiazole-4-carbonitrile.

paragraph 21. The use of paragraph 18, wherein the condition is stroke, periventricular leukomalacia, cardiac arrest with resuscitation, atherosclerosis, Parkinson's disease, Alzheimer's disease, or breast cancer.

Definitions

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Further, unless otherwise required by context, singular terms shall include pluralities and plural terms shall include the singular.

As used herein the term "comprising" or "comprises" is used in reference to compositions, methods, and respective component(s) thereof, that are useful to an embodiment, yet open to the inclusion of unspecified elements, whether useful or not.

As used herein the term "consisting essentially of" refers to those elements required for a given embodiment. The term permits the presence of elements that do not materially affect the basic and novel or functional characteristic(s) of that embodiment of the invention.

The terms "decrease", "reduce", or "inhibit" are all used herein to mean a decrease by a statistically significant amount. In some embodiments, "decrease", "reduce", or "inhibit" typically means a decrease by at least 10% as compared to a reference level (e.g., the absence of a given treatment) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. A 12/15-LOX inhibitor can therefore decrease the biological function or activity of 12/15-LOX by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more.

The term "disease", "disorder", or "condition" is used interchangeably herein, refers to any alternation in state of the body or of some of the organs, interrupting or disturbing the performance of the functions and/or causing symptoms such as discomfort, dysfunction, distress, or even death to the person afflicted or those in contact with a person. A disease, disorder, or condition can also related to a distemper, ailing, ailment, malady, disorder, sickness, illness, complaint, affectation.

As used here, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used here, the term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient.

The phrase "therapeutically-effective amount" as used herein means that amount of a compound, material, or composition which is effective for producing some desired therapeutic effect in at least a sub-population of cells in an animal at a reasonable benefit/risk ratio applicable to any medical treatment. For example, an amount of a compound administered to a subject that is sufficient to produce a statistically significant, measurable change in at least one symptom of strokes. For example, the brain infarct size is decreased by at least about 5%, at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. Determination of a therapeutically effective amount is well within the capability of those skilled in the art. Generally, a therapeutically effective amount can vary with the subject's history, age, condition, sex, as well as the severity and type of the medical condition in the subject, and administration of other pharmaceutically active agents.

As used herein, the term "administer" refers to the placement of a 12/15-LOX inhibitor into a subject by a method or route which results in at least partial localization of the 12/15-LOX inhibitor at a desired site such that desired effect is produced. A compound or composition described herein can be administered by any appropriate route known in the art including, but not limited to, oral or parenteral routes, including intravenous, intramuscular, subcutaneous, transdermal, airway (aerosol), pulmonary, nasal, rectal, and topical (including buccal and sublingual) administration.

Exemplary modes of administration include, but are not limited to, injection, infusion, instillation, inhalation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In preferred embodiments, the compositions are administered by intravenous infusion or injection.

By "treatment", "prevention" or "amelioration" of a disease, disorder, or condition is meant delaying or preventing the onset of such a disease or disorder, reversing, alleviating, ameliorating, inhibiting, slowing down or stopping the progression, aggravation or deterioration the progression or severity of a condition associated with such a disease, disorder, or condition. The term "treatment" of a disease, disorder, or condition also includes providing relief from the symptoms or side-effects of the disease (including palliative treatment). In one embodiment, the symptoms of a disease, disorder, or condition are alleviated by at least 5%, at least 10%, at least 20%, at least 30%, at least 40%, or at least 50%.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, and canine species, e.g., dog, fox, wolf. The terms, "patient", "individual" and "subject" are used interchangeably herein.

Preferably, the subject is a mammal. The mammal can be a human, non-human primate, mouse, rat, dog, cat, horse, or cow, but are not limited to these examples.

Certain compounds of the present invention and definitions of specific functional groups are also described in more detail below. For purposes of this invention, the chemical elements are identified in accordance with the Periodic Table of the Elements, CAS version, *Handbook of Chemistry and Physics,* 75th Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito: 1999, the entire contents of which are incorporated herein by reference.

As used herein, the term "aliphatic" means a moiety characterized by a straight or branched chain arrangement of constituent carbon atoms and can be saturated or partially unsaturated with one or more (e.g., one, two, three, four, five or more) double or triple bonds.

As used herein, the term "alicyclic" means a moiety comprising a nonaromatic ring structure. Alicyclic moieties can be saturated or partially unsaturated with one or more double or triple bonds. Alicyclic moieties can also optionally comprise heteroatoms such as nitrogen, oxygen and sulfur. The nitrogen atoms can be optionally quaternerized or oxidized and the sulfur atoms can be optionally oxidized. Examples of alicyclic moieties include, but are not limited to moieties with $C_3$-$C_8$ rings such as cyclopropyl, cyclohexane, cyclopentane, cyclopentene, cyclopentadiene, cyclohexane, cyclohexene, cyclohexadiene, cycloheptane, cycloheptene, cycloheptadiene, cyclooctane, cyclooctene, and cyclooctadiene.

The term, "heteroatom" refers to an atom that is not a carbon atom. Particular examples of heteroatoms include, but are not limited to nitrogen, oxygen, sulfur and halogens. A "heteroatom moiety" includes a moiety where the atom by which the moiety is attached is not a carbon. Examples of heteroatom moieties include —N=, —$NR^N$—, —$N^+$($O^-$)=, —O—, —S— or —$S(O)_2$—, —$OS(O)_2$—, and —SS—, wherein $R^N$ is H or a further substituent.

As used herein, the term "alkyl" means a straight or branched, saturated aliphatic radical having a chain of carbon atoms. $C_x$ alkyl and $C_x$-$C_y$ alkyl are typically used where X and Y indicate the number of carbon atoms in the chain. For example, $C_1$-$C_6$ alkyl includes alkyls that have a chain of between 1 and 6 carbons (e.g., methyl, ethyl, propyl, isopropyl, butyl, sec-butyl, isobutyl, tert-butyl, pentyl, neopentyl, hexyl, and the like). Alkyl represented along with another radical (e.g., as in arylalkyl) means a straight or branched, saturated alkyl divalent radical having the number of atoms indicated or when no atoms are indicated means a bond, e.g., ($C_6$-$C_{10}$)aryl($C_0$-$C_3$)alkyl includes phenyl, benzyl, phenethyl, 1-phenylethyl 3-phenylpropyl, and the like. Backbone of the alkyl can be optionally inserted with one or more heteroatoms, such as N, O, or S.

In preferred embodiments, a straight chain or branched chain alkyl has 30 or fewer carbon atoms in its backbone (e.g., C1-C30 for straight chains, C3-C30 for branched chains), and more preferably 20 or fewer. Likewise, preferred cycloalkyls have from 3-10 carbon atoms in their ring structure, and more preferably have 5, 6 or 7 carbons in the ring structure. The term "alkyl" (or "lower alkyl") as used throughout the specification, examples, and claims is intended to include both "unsubstituted alkyls" and "substituted alkyls", the latter of which refers to alkyl moieties having one or more substituents replacing a hydrogen on one or more carbons of the hydrocarbon backbone. In some embodiments, a straight chain or branched chain alkyl has 5 or fewer carbon atoms, 10 or fewer carbon atoms, or 15 or fewer carbon atoms.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Throughout the application, preferred alkyl groups are lower alkyls. In preferred embodiments, a substituent designated herein as alkyl is a lower alkyl.

Substituents of a substituted alkyl can include halogen, hydroxy, nitro, thiols, amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. In some embodiments, the substituted alkyl is a perfluorinated alkyl.

As used herein, the term "alkenyl" refers to unsaturated straight-chain, branched-chain or cyclic hydrocarbon radicals having at least one carbon-carbon double bond. $C_x$ alkenyl and $C_x$-$C_y$ alkenyl are typically used where X and Y indicate the number of carbon atoms in the chain. For example, $C_2$-$C_6$alkenyl includes alkenyls that have a chain of between 1 and 6 carbons and at least one double bond, e.g., vinyl, allyl, propenyl, isopropenyl, 1-butenyl, 2-butenyl, 3-butenyl, 2-methylallyl, 1-hexenyl, 2-hexenyl, 3-hexenyl, and the like). Alkenyl represented along with another radical (e.g., as in arylalkenyl) means a straight or branched, alkenyl divalent radical having the number of atoms indicated. Backbone of the alkenyl can be optionally inserted with one or more heteroatoms, such as N, O, or S. In some embodiments, the substituted alkenyl is a perfluorinated alkenyl.

As used herein, the term "alkynyl" refers to unsaturated hydrocarbon radicals having at least one carbon-carbon triple bond. $C_x$ alkynyl and $C_x$-$C_y$ alkynyl are typically used where X and Y indicate the number of carbon atoms in the chain. For example, $C_2$-$C_6$alkynyl includes alkynls that have a chain of between 1 and 6 carbons and at least one triple bond, e.g., ethynyl, 1-propynyl, 2-propynyl, 1-butynyl, isopentynyl, 1,3-hexa-diyn-yl, n-hexynyl, 3-pentynyl, 1-hexen-3-ynyl and the like. Alkynyl represented along with another radical (e.g., as in arylalkynyl) means a straight or branched, alkynyl divalent radical having the number of atoms indicated. Backbone of the alkynyl can be optionally inserted with one or more heteroatoms, such as N, O, or S. In some embodiments, the substituted alkynyl is a perfluorinated alkynyl.

The terms "alkylene," "alkenylene," and "alkynylene" refer to divalent alkyl, alkelyne, and alkynylene" radicals. Prefixes $C_x$ and $C_x$-$C_y$ are typically used where X and Y indicate the number of carbon atoms in the chain. For example, $C_1$-$C_6$alkylene includes methylene, (—$CH_2$—), ethylene (—$CH_2CH_2$—), trimethylene (—$CH_2CH_2CH_2$—), tetramethylene (—$CH_2CH_2CH_2CH_2$—), 2-methyltetramethylene (—$CH_2CH(CH_3)CH_2CH_2$—), pentamethylene (—$CH_2CH_2CH_2CH_2CH_2$—) and the like).

As used herein, the term "alkylidene" means a straight or branched unsaturated, aliphatic, divalent radical having a general formula =$CR_aR_b$. $C_x$ alkylidene and $C_x$-$C_y$alkylidene are typically used where X and Y indicate the number of carbon atoms in the chain. For example, $C_2$-$C_6$alkylidene includes methylidene (=$CH_2$), ethylidene (=$CHCH_3$), isopropylidene (=$C(CH_3)_2$), propylidene (=$CHCH_2CH_3$), allylidene (=CH—CH=$CH_2$), and the like).

As used herein, the term "halogen" or "halo" refers to an atom selected from fluorine, chlorine, bromine and iodine.

The term "aryl" refers to monocyclic, bicyclic, or tricyclic fused aromatic ring system. $C_x$ aryl and $C_x$-$C_y$ aryl are typically used where X and Y indicate the number of carbon atoms in the ring system. An aryl group can comprise a 4-atom ring, a 5-atom ring, a 6-atom ring, a 7-atom ring, a 8-atom ring, a 9 atom ring, or more. Exemplary aryl groups include, but are not limited to, pyridinyl, pyrimidinyl, furanyl, thienyl, imidazolyl, thiazolyl, pyrazolyl, pyridazinyl, pyrazinyl, triazinyl, tetrazolyl, indolyl, benzyl, phenyl, naphthyl, anthracenyl, azulenyl, fluorenyl, indanyl, indenyl, naphthyl, phenyl, tetrahydronaphthyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl, and the like. In some embodiments, 1, 2, 3, or 4 hydrogen atoms of each ring can be substituted by a substituent.

The term "heteroaryl" refers to an aromatic 5-8 membered monocyclic, 8-12 membered fused bicyclic, or 11-14 membered fused tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively. $C_x$ heteroaryl and $C_x$-$C_y$heteroaryl are typically used where X and Y indicate the number of carbon atoms in the ring system. Heteroaryls include, but are not limited to, those derived from benzo[b]furan, benzo[b]thiophene, benzimidazole, imidazo[4,5-c]pyridine, quinazoline, thieno[2,3-c]pyridine, thieno[3,2-b]pyridine, thieno[2,3-b]pyridine, indolizine, imidazo[1,2a]pyridine, quinoline, isoquinoline, phthalazine, quinoxaline, naphthyridine, quinolizine, indole, isoindole, indazole, indoline, benzoxazole, benzopyrazole, benzothiazole, imidazo[1,5-a]pyridine, pyrazolo[1,5-a]pyridine, imidazo[1,2-a]pyrimidine, imidazo[1,2-c]pyrimidine, imidazo[1,5-a]pyrimidine, imidazo[1,5-c]pyrimidine, pyrrolo[2,3-b]pyridine, pyrrolo[2,3c]pyridine, pyrrolo[3,2-c]pyridine, pyrrolo[3,2-b]pyridine, pyrrolo[2,3-d]pyrimidine, pyrrolo[3,2-d]pyrimidine, pyrrolo[2,3-b]pyrazine, pyrazolo[1,5-a]pyridine, pyrrolo[1,2-b]pyridazine, pyrrolo[1,2-c]pyrimidine, pyrrolo[1,2-a]pyrimidine, pyrrolo[1,2-a]pyrazine, triazo[1,5-a]pyridine, pteridine, purine, carbazole, acridine, phenazine, phenothiazene, phenoxazine, 1,2-dihydropyrrolo[3,2,1-hi]indole, indolizine, pyrido[1,2-a]indole, 2(1H)-pyridinone, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxepanyl, oxetanyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydropyranyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl. Some exemplary heteroaryl groups include, but are not limited to, pyridyl, furyl or furanyl, imidazolyl, benzimidazolyl, pyrimidinyl, thiophenyl or thienyl, pyridazinyl, pyrazinyl, quinolinyl, indolyl, thiazolyl, naphthyridinyl, 2-amino-4-oxo-3,4-dihydropteridin-6-yl, tetrahydroisoquinolinyl, and the like. In some embodiments, 1, 2, 3, or 4 hydrogen atoms of each ring may be substituted by a substituent.

Aryl and heteroaryls can be optionally substituted with one or more substituents at one or more positions, for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The term "cyclyl" or "cycloalkyl" refers to saturated and partially unsaturated cyclic hydrocarbon groups having 3 to 12 carbons, for example, 3 to 8 carbons, and, for example, 3 to 6 carbons. C$_x$cyclyl and C$_x$-C$_y$cylcyl are typically used where X and Y indicate the number of carbon atoms in the ring system. The cycloalkyl group additionally can be optionally substituted, e.g., with 1, 2, 3, or 4 substituents. C$_3$-C$_{10}$cyclyl includes cyclopropyl, cyclobutyl, cyclopentyl, cyclohexyl, cyclohexenyl, 2,5-cyclohexadienyl, cycloheptyl, cyclooctyl, bicyclo[2.2.2]octyl, adamantan-1-yl, decahydronaphthyl, oxocyclohexyl, dioxocyclohexyl, thiocyclohexyl, 2-oxobicyclo[2.2.1]hept-1-yl, and the like.

The term "heterocyclyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively). C$_x$ heterocyclyl and C$_x$-C$_y$ heterocyclyl are typically used where X and Y indicate the number of carbon atoms in the ring system. In some embodiments, 1, 2 or 3 hydrogen atoms of each ring can be substituted by a substituent. Exemplary heterocyclyl groups include, but are not limited to piperazinyl, pyrrolidinyl, dioxanyl, morpholinyl, tetrahydrofuranyl, piperidyl, 4-morpholyl, 4-piperazinyl, pyrrolidinyl, perhydropyrrolizinyl, 1,4-diazaperhydroepinyl, 1,3-dioxanyl, 1,4-dioxanyland the like.

The terms "bicyclic" and "tricyclic" refers to fused, bridged, or joined by a single bond polycyclic ring assemblies.

The term "cyclylalkylene" means a divalent aryl, heteroaryl, cyclyl, or heterocyclyl.

As used herein, the term, "aromatic" means a moiety wherein the constituent atoms make up an unsaturated ring system, all atoms in the ring system are sp$^2$ hybridized and the total number of pi electrons is equal to 4n+2. An aromatic ring can be such that the ring atoms are only carbon atoms (e.g., aryl) or can include carbon and non-carbon atoms (e.g., heteroaryl).

As used herein, the term "substituted" refers to independent replacement of one or more (typically 1, 2, 3, 4, or 5) of the hydrogen atoms on the substituted moiety with substituents independently selected from the group of substituents listed below in the definition for "substituents" or otherwise specified. In general, a non-hydrogen substituent can be any substituent that can be bound to an atom of the given moiety that is specified to be substituted. Examples of substituents include, but are not limited to, acyl, acylamino, acyloxy, aldehyde, alicyclic, aliphatic, alkanesulfonamido, alkanesulfonyl, alkaryl, alkenyl, alkoxy, alkoxycarbonyl, alkyl, alkylamino, alkylcarbanoyl, alkylene, alkylidene, alkylthios, alkynyl, amide, amido, amino, aminoalkyl, aralkyl, aralkylsulfonamido, arenesulfonamido, arenesulfonyl, aromatic, aryl, arylamino, arylcarbanoyl, aryloxy, azido, carbamoyl, carbonyls (including ketones), carboxy, carboxylates, CF$_3$, cyano (CN), cycloalkyl, cycloalkylene, ester, ether, haloalkyl, halogen, halogen, heteroaryl, heterocyclyl, hydroxy, hydroxy, hydroxyalkyl, imino, iminoketone, ketone, mercapto, nitro, oxaalkyl, oxo, oxoalkyl, phosphoryl (including phosphonate and phosphinate), silyl groups, sulfonamido, sulfonyl (including sulfate, sulfamoyl and sulfonate), thiols, and ureido moieties, each of which may optionally also be substituted or unsubstituted. In some cases, two substituents, together with the carbon(s) to which they are attached to, can form a ring.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy, n-propyloxy, isopropyloxy, n-butyloxy, iso-butyloxy, and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, and —O-alkynyl. Aroxy can be represented by —O-aryl or O-heteroaryl, wherein aryl and heteroaryl are as defined below. The alkoxy and aroxy groups can be substituted as described above for alkyl.

The term "aralkyl", as used herein, refers to an alkyl group substituted with an aryl group (e.g., an aromatic or heteroaromatic group).

The term "alkylthio" refers to an alkyl group, as defined above, having a sulfur radical attached thereto. In preferred embodiments, the "alkylthio" moiety is represented by one of —S-alkyl, —S-alkenyl, and —S-alkynyl. Representative alkylthio groups include methylthio, ethylthio, and the like. The term "alkylthio" also encompasses cycloalkyl groups, alkene and cycloalkene groups, and alkyne groups. "Arylthio" refers to aryl or heteroaryl groups.

As used herein, the term "amino" means —NH$_2$. The term "alkylamino" means a nitrogen moiety having at least one straight or branched unsaturated aliphatic, cyclyl, or heterocyclyl radicals attached to the nitrogen. For example, representative amino groups include —NH$_2$, —NHCH$_3$, —N(CH$_3$)$_2$, —N(C$_1$-C$_{10}$alkyl)$_2$, and the like. The term "alkylamino" includes "alkenylamino," "alkynylamino," "cyclylamino," and "heterocyclylamino." The term "arylamino" means a nitrogen moiety having at least one aryl radical attached to the nitrogen. For example —NHaryl, and —N(aryl)$_2$. The term "heteroarylamino" means a nitrogen moiety having at least one heteroaryl radical attached to the nitrogen. For example —NHheteroaryl, and —N(heteroaryl)$_2$. Optionally, two substituents together with the nitrogen can also form a ring. Unless indicated otherwise, the compounds described herein containing amino moieties can include protected derivatives thereof. Suitable protecting groups for amino moieties include acetyl, tertbutoxycarbonyl, benzyloxycarbonyl, and the like.

The term "aminoalkyl" means an alkyl, alkenyl, and alkynyl as defined above, except where one or more substituted or unsubstituted nitrogen atoms (—N—) are positioned between carbon atoms of the alkyl, alkenyl, or alkynyl. For example, an (C$_2$-C$_6$) aminoalkyl refers to a chain comprising between 2 and 6 carbons and one or more nitrogen atoms positioned between the carbon atoms.

As used herein, the term "carbonyl" means the radical —C(O)—. It is noted that the carbonyl radical can be further substituted with a variety of substituents to form different carbonyl groups including acids, acid halides, amides, esters, ketones, and the like.

The term "carboxyl" refers to a functional group with the formula —COOH.

The term "carboxy" means the radical —C(O)O—. It is noted that compounds described herein containing carboxy moieties can include protected derivatives thereof, i.e., where the oxygen is substituted with a protecting group. Suitable protecting groups for carboxy moieties include benzyl, tert-butyl, and the like.

The term "hydroxyl" means the radical —OH.

The term "nitro" means the radical —NO$_2$.

The term "sulfonyl" means the radical —SO$_2$—. It is noted that the sulfonyl radical can be further substituted with a variety of substituents to form different sulfonyl groups including sulfonic acids (—SO$_3$H), sulfonamides, sulfonate esters, sulfones, and the like.

As used herein, the term "pharmaceutically-acceptable salts" refers to the conventional nontoxic salts or quaternary ammonium salts of therapeutic agents, e.g., from non-toxic organic or inorganic acids. These salts can be prepared in situ in the administration vehicle or the dosage form manufacturing process, or by separately reacting a therapeutic agent in its free base or acid form with a suitable organic or inorganic acid or base, and isolating the salt thus formed during subsequent purification. Conventional nontoxic salts include those derived from inorganic acids such as sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like. See, for example, Berge et al., "Pharmaceutical Salts", *J. Pharm. Sci.* 66:1-19 (1977), content of which is herein incorporated by reference in its entirety.

In some embodiments of the aspects described herein, representative salts include the hydrobromide, hydrochloride, sulfate, bisulfate, phosphate, nitrate, acetate, succinate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like.

The singular terms "a," "an," and "the" include plural referents unless context clearly indicates otherwise. Similarly, the word "or" is intended to include "and" unless the context clearly indicates otherwise.

Other than in the operating examples, or where otherwise indicated, all numbers expressing quantities of ingredients or reaction conditions used herein should be understood as modified in all instances by the term "about." The term "about" when used in connection with percentages may mean±5% of the value being referred to. For example, about 100 means from 95 to 105.

Although methods and materials similar or equivalent to those disclosed herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. Further, to the extent not already indicated, it will be understood by those of ordinary skill in the art that any one of the various embodiments herein described and illustrated can be further modified to incorporate features shown in any of the other embodiments disclosed herein.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology disclosed herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are disclosed herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments disclosed herein can be combined to provide further embodiments. Aspects of the disclosure can be modified, if necessary, to employ the compositions, functions and concepts of the above references and application to provide yet further embodiments of the disclosure.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

EXAMPLES

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The following examples do not in any way limit the invention.

The technology disclosed herein is further illustrated by the following examples which in no way should be construed as being further limiting.

Example 1: Potent and Selective Inhibitors of Human Reticulocyte 12/15-Lipoxygenase A key challenge facing drug discovery today is variability of the drug target between species, such as with 12/15-lipoxygenase (12/15-LOX), which contributes to ischemic brain injury, but its human and rodent isozymes have different inhibitor specificities. Described herein, the inventors have utilized a quantitative high-throughput (qHTS) screen to identify, among other things, compound 1 (ML351), a novel chemotype for 12/15-LOX inhibition, which has nanomolar potency ($IC_{50}$=200 nM) against human 12/15-LOX and is protective against oxidative glutamate toxicity in mouse neuronal HT-22 cells. In addition, it exhibited greater than 250-fold selectivity versus related LOX isozymes, was a mixed inhibitor, and did not reduce the active-site ferric ion. Finally, 1 significantly reduced infarct size following permanent focal ischemia in a mouse model of ischemic stroke. As such, this represents the first report of a selective inhibitor of human 12/15-LOX with demonstrated in vivo activity in proof-of-concept mouse models of stroke.

Chemistry

The compounds 1-18 from Table 1 were synthesized as shown in FIG. 1A. The intermediates 1i-18i and 19 were obtained by propylphosphonic anhydride (T3P®) assisted coupling of the corresponding commercially available carboxylic acids with 2-aminomalanonitrile, followed by cyclization in one step. This modified synthesis of 5-amino-2-substituted-1,3-oxazole-4-carbonitriles allows facile access to a variety of compounds via a simple work up and purification from commercially available carboxylic acids. Due to low nucleophilicity of the amine group, the initial attempts to monomethylate the 5-amino-2-substituted-1,3-oxazole-4-carbonitrile intermediate with several known methylation methods including methyl iodide, formic acid or methyl boronic acid were met with limited success. However, condensation with paraformaldehyde in the presence of sodium methoxide in methanol, followed by in situ reduction with sodium borohydride, afforded the required products 1-18 in modest yields.

TABLE 1

Variations to compound 1 (analogs 2-18).[a]

| Compound | R | $IC_{50}$ (μM) [±SD μM] |
|---|---|---|
| 1 | 1-naphthyl | 0.20 [0.04] |
| 2 | 2-naphthyl | >30[b] |
| 3 | isoquinolin-5-yl | >30[b] |
| 4 | quinolin-5-yl | 3.6 [0.5] |
| 5 | isoquinolin-6-yl | 0.73 |

TABLE 1-continued

Variations to compound 1 (analogs 2-18).[a]

[Core structure: 2-R-5-(methylamino)-oxazole-4-carbonitrile]

| Compound | R | IC$_{50}$ (μM) [±SD μM] |
|---|---|---|
| 6 | quinoxalin-5-yl | >40 |
| 7 | 2,3-dichlorophenyl | 0.46 [0.06] |
| 8 | 3,4-dichlorophenyl | 0.81 [0.2] |
| 9 | 2,3-dihydrobenzo[1,4]dioxin-6-yl | >40 |
| 10 | benzo[1,3]dioxol-5-yl | 7.6 [2] |
| 11 | 4-phenylphenyl (biphenyl-4-yl) | >40 |
| 12 | 2-phenylphenyl (biphenyl-2-yl) | 23 [13] |
| 13 | 1H-indol-6-yl | >40 |
| 14 | 1H-indol-3-yl | 3.9 [0.2] |
| 15 | 4-chlorophenyl | 25 [4] |
| 16 | 3-chlorophenyl | 6.3 [0.5] |
| 17 | 4-fluorophenyl | 15 [1] |
| 18 | cyclopentyl | >50[b] |

In Table 1, [a]IC$_{50}$ values represent the half maximal (50%) inhibitory concentration as determined in the UV-Vis cuvette-based assay in triplicate. [b]Compound possessed low efficacy, with less than 50% maximal inhibition at 25 μM inhibitor.

Figure 1B:
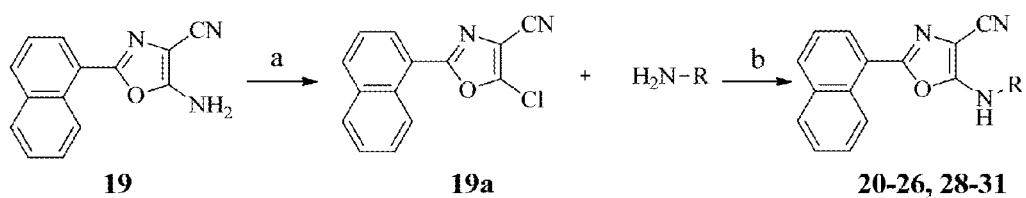

FIG. 1B represents the general methodology utilized for the synthesis of compounds listed in Table 2. Towards this end, 5-Amino-2-(naphthalen-1-yl)oxazole-4-carbonitrile 19 was converted to an advanced intermediate (19a), via Sandmeyer reaction by treating with t-butyl nitrite in the presence of copper (II) chloride. Heating the various amines to reflux with intermediate 19a in THF afforded the required analogs 20-26 and 28-31. Compound 27 was obtained via acetylation of intermediate 19 with acetic anhydride, cat. DMAP.

TABLE 2

Variations to compound 1 (analogs 19-31).[a]

[Structure: 1-naphthyl group attached to oxazole ring with R at 5-position and CN at 4-position]

| Compound | R | IC$_{50}$ (μM) [±SD (μM)] |
|---|---|---|
| 1 | NHMe | 0.20 [0.04] |
| 19 | NH$_2$ | 25 [10] |
| 20 | N(Me)$_2$ | >30[b] |
| 21 | HN-ethyl | 0.12 [0.3] |
| 22 | HN-propyl | 0.10 [0.3] |
| 23 | HN-butyl | 0.12 [0.05] |
| 24 | HN-pentyl | 0.3 [0.04] |
| 25 | HN-allyl | 3.0 [1] |
| 26 | HN-iPr | >40 |
| 27 | NHAc | 10 [3] |
| 28 | HN-CH$_2$Ph | >30[b] |
| 29 | HN·Ph | >30[b] |
| 30 | HN-oxetanyl | >25 |
| 31 | HN-azetidinyl(NH) | >40 |

In Table 2, [a]IC$_{50}$ values represent the half maximal (50%) inhibitory concentration as determined in the UV-Vis cuvette-based assay in triplicate. [b]Compound possessed low efficacy, with less than 50% maximal inhibition at 25 μM inhibitor.

Figure 1C:
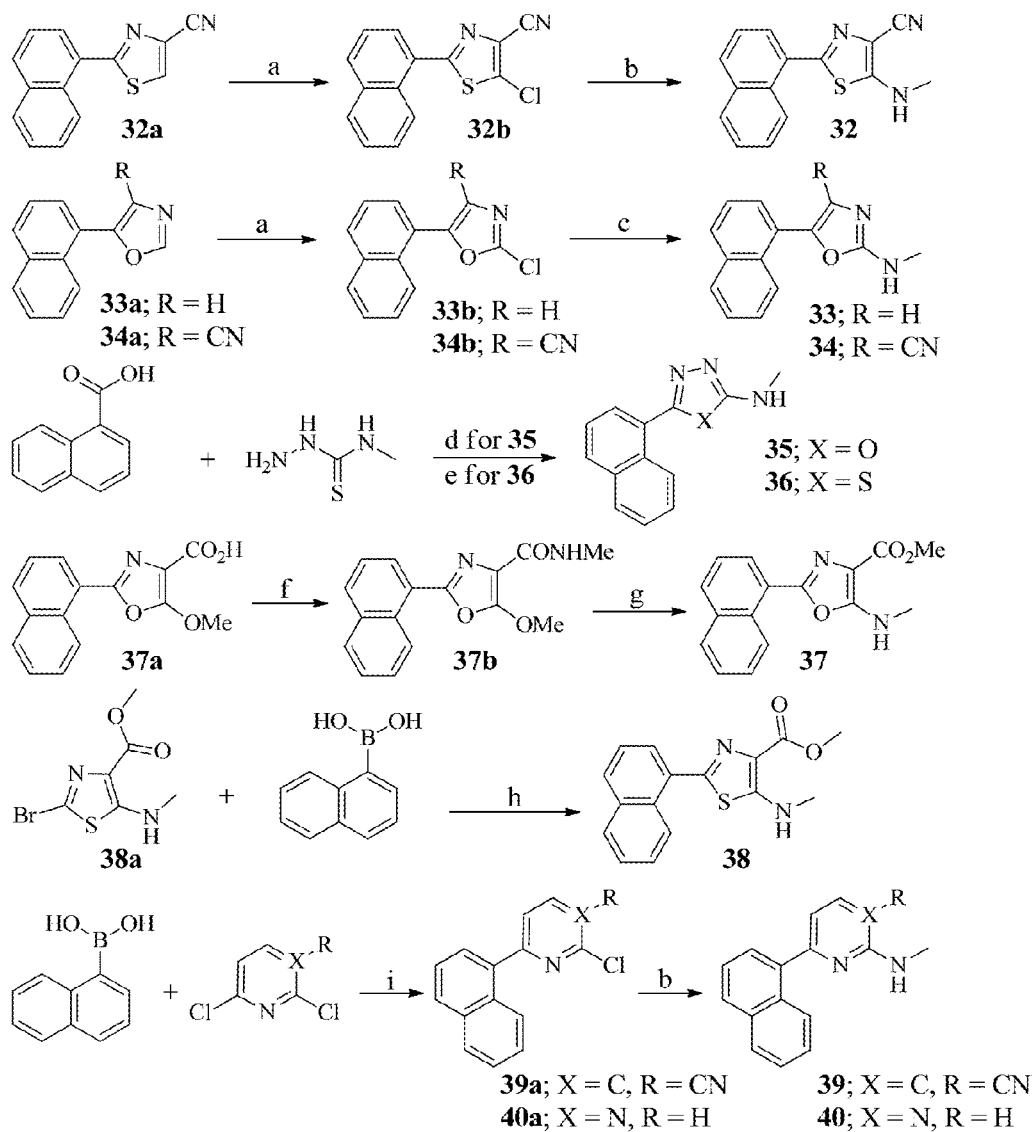

The synthesis of compounds 32-40 (Table 3) is outlined in FIG. 1C. Analogs 32-34 were prepared via chlorination of the intermediates, 32a-34a, with hexachloroethane in the presence of LDA, followed by condensation with methylamine. Amination of 5-chloro-2-(naphthalen-1-yl)thiazole-4-carbonitrile (32b) required microwave heating in a polar solvent, such as 2-propanol, for complete conversion of the starting material. The details of the synthesis of the intermediate, 32a,[63,64] is described somewhere else in the Example. Intermediates 33a and 33b were synthesized following the literature protocols described for similar compounds. The reaction of 4-methyl-3-thiosemicarbazide with 1-naphthoic acid in the presence of EDC furnished the oxadiazole analog 35, but surprisingly when T$_3$P coupling condition was used, only the thiadiazole analog 36 was formed. Synthesis of compound 37 was accomplished utilizing a Cornforth rearrangement of the intermediate 37b, which is prepared from the intermediate 37a by coupling with methylamine as shown in Scheme 3. The intermediate 37a was prepared according to a known protocol reported to similar compounds in the literature.[65] The synthesis of analog 38 from 1-naphthyl boronic acid and the intermediate 38a using classical Suzuki conditions was met with limited success.[66] The Suzuki coupling reaction was successful using a silica bound DPP-Pd catalyst (SiliaCat®-DPP-Pd) under reflux conditions over 24 hours. Synthesis of the intermediates, 39a-40a, were accomplished using a Pd(PPh$_3$)$_4$-catalyzed microwave assisted regioselective Suzuki coupling between 1-naphthyl boronic acid and 2,6-dichloro pyridine or pyrimidine derivative, respectively. Subsequent condensation of these intermediates with methylamine furnished the desired analogs, 39-40, following HPLC purification.

TABLE 3

Variations to compound 1 (analogs 32-40)[a]

[Structure: 1-naphthyl attached to R group]

| Compound | R | IC$_{50}$ (μM) [±SD (μM)] |
|---|---|---|
| 1 | oxazole with NHMe and CN | 0.20 [0.04] |
| 32 | thiazole with NHMe and CN | 0.55 [0.06] |
| 33 | oxazole with NHMe (2-position) | >40 |
| 34 | oxazole with NHMe (2-position), CN at 4 | >40 |
| 35 | oxadiazole with NHMe | 5.4 [1.8] |
| 36 | thiadiazole with NHMe | >40 |
| 37 | oxazole with NHMe and C(O)OMe | >40 |

TABLE 3-continued

Variations to compound 1 (analogs 32-40)[a]

| Compound | R | IC$_{50}$ (μM) [±SD (μM)] |
|---|---|---|
| 38 | thiazole with NHMe, OMe, C=O substituents | >30[b] |
| 39 | pyridine with CN and NHMe | >40 |
| 40 | pyrimidine with NHMe | >40 |

In Table 3, [a]IC$_{50}$ values represent the half maximal (50%) inhibitory concentration as determined in the UV-Vis cuvette-based assay in triplicate. [b]Compound possessed low efficacy, with less than 50% maximal inhibition at 25 μM inhibitor.

Results and Discussion

To investigate structural requirements for optimal 12/15-LOX inhibition, a SAR study of the lead molecule was conducted, as shown in Tables 1-3 (1-40). Initially, the 1-naphthyl group on the left side of the molecule was replaced with various aryl and heterocyclic groups as shown in Table 1. The bioisosteric replacement of 1-naphthyl with 2,3-dichlorophenyl (7) or 3,4-dichlorophenyl (8) groups showed comparable, albeit slightly lower potencies than 1 (IC$_{50}$=0.46 μM, 0.81 μM and 0.20 μM, respectively). Replacement with a 2-naphthyl group showed reduced potency (2, IC$_{50}$>30 μM) compared to the 1-naphthyl substitution, which based on space-filling analysis, agreed with the findings observed for dichloro analogs 7 and 8. Several other modifications, including saturated rings or heterocyclic rings at this region (3-6 and 9-18), also resulted in reduced potency. Thus, in general, the 1-naphthyl group appeared to be optimal for 12/15-LOX inhibition, as variations in size and electrostatics in this region were not well tolerated. Accordingly, the 1-naphthyl group was held constant while other regions of the molecule were explored for further SAR (Tables 2 & 3).

Having explored modifications to the 1-naphthyl moiety, the next focus was to explore modifications of the N-methyl side chain at the 5-position, as shown in Table 2 (19-31). Removal of the methyl group drastically reduced potency (19, IC$_{50}$=25 μM) and di-methylation reduced potency as well (20, IC$_{50}$>30 Modifications of the methyl group with other alkyl substitutions, such as ethyl, n-propyl, n-butyl and n-pentyl groups, were tolerated (21-25), with comparable or even improved potency being observed. However, replacing the methyl group with a branched alkyl group (26) or cycloalkyl groups (30-31) significantly reduced the potency. Larger groups, such as benzyl (28, IC$_{50}$>30 μM) or phenyl substituted analogs (29, IC$_{50}$>30 also showed diminished 12/15-LOX activity. Overall, these data suggested that the mono-alkylation with straight chain alkyl groups is important for optimal 12/15-LOX inhibition.

Finally, attention was turned to optimization of the 1,3-oxazole core and its various substituents (Table 3). Replacing the 1,3-oxazole core with a 1,3-thiazole ring (32, IC$_{50}$=0.55 μM) resulted in a two-fold decrease in potency. This result could be partly attributed to the difference in size and hardness/softness of the sulfur and oxygen atoms in the thiazole and oxazole rings respectively. The diminished potency trend continued further for the pyridine (39, IC$_{50}$>40 μM) and pyrimidine analogs (40, IC$_{50}$>40 Attempts to mimic the interaction of the oxazole core were largely unsuccessful with the N-methyl/oxadiazole derivative (35, IC$_{50}$=5.4 μM) or the thiadiazole analog (36, IC$_{50}$>40 Interchanging the positions of the 1-naphthyl group and the —NHMe group (analogs 33-34) also led to complete loss of activity. In summary, this chemotype showed very tight SAR and the efforts to make several changes around the lead molecule resulted in similar or lower potency, with exception to analogs 21-23, which showed marginally improved potency.

Biological Evaluation of ML351

Concurrently with the SAR investigations against human 12/15-LOX in vitro, the potency of 1 against mouse 12/15-LOX was investigated, utilizing a neuronal cell based assay. Glutamate-induced oxidative stress[67-69] leads to time-dependent cell death mediated by 12/15-LOX in both immature primary neurons and mouse hippocampal HT22 cells.[38, 46,70] Primary neurons require a lengthy isolation procedure and also show relatively modest increases in cell death in this assay, indicating they are not suited for a high-throughput testing approach. In contrast, HT22 cells grow quickly and consistently feature low cell death under control conditions, but a majority of cells die after glutamate treatment (50-100%). This assay can be adapted to 96-well plates, allowing for moderate to high throughput against the screened compounds. The characteristic Z' score used to evaluate the technical quality and suitability as screening tool averaged 0.77 over ten experiments (SD=0.13; range, 0.49-0.94), where values above 0.5 indicate an excellent assay.[71]

Figures 2A, 2B:
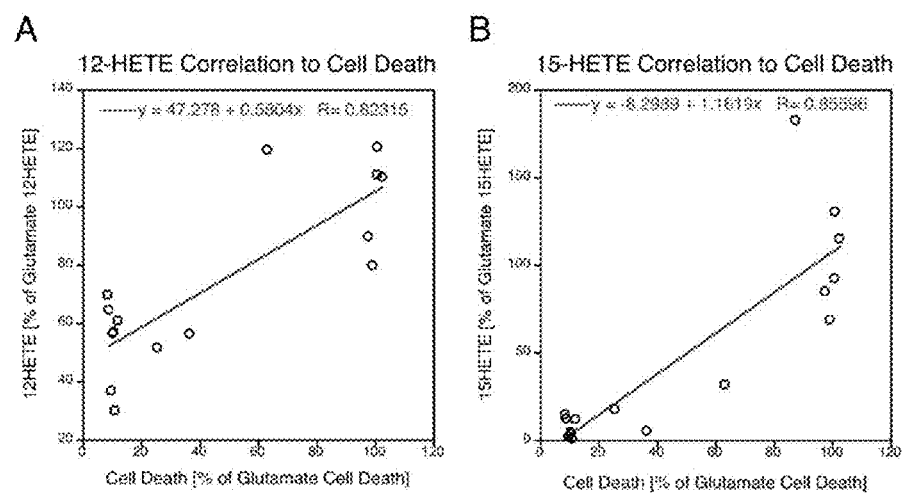
FIGS. 2A-2B show correlation between arachidonic acid metabolites and cell death.

To verify that inhibition of oxidative stress-related cell death in HT22 cells is indeed a good measure of the efficacy of a given inhibitor against the mouse 12/15-LOX, the characteristics of cell injury in this model was investigated. Levels of the mouse 12/15-LOX product, 12-HETE, are known to be increased in the mouse brain following ischemia,[34] and they are also elevated by glutamate treatment of HT22 cells.[34,38] HPLC/MS was used to measure 12-HETE secreted to the medium from cells incubated under control conditions or treated with glutamate, as well as co-treated with several compounds with or without inhibitory activity for mouse 12/15-LOX. Following exclusion of one outlier with extremely high 12-HETE (but also high levels of cell death), there was a good correlation between cell death and levels of 12-HETE secreted; when 12-HETE levels were high, there was increased cell death, when 12-HETE levels were low, there was little cell death (FIG. 2A). Interestingly, levels of 15-HETE were also increased in the medium of glutamate-treated HT22 cells, to a similar extent as 12-HETE (FIG. 2B). This was surprising because the mouse 12/15-LOX is generally thought to make only minor amounts of 15-HETE, typically less than 20% of the 12-HETE generated. Nonetheless, 15-HETE production was also blocked by 12/15-LOX inhibitors that protected HT22 cells and reduced 12-HETE levels, indicating that both arachidonic acid metabolites were made by the same enzyme.

Figures 3A, 3B:
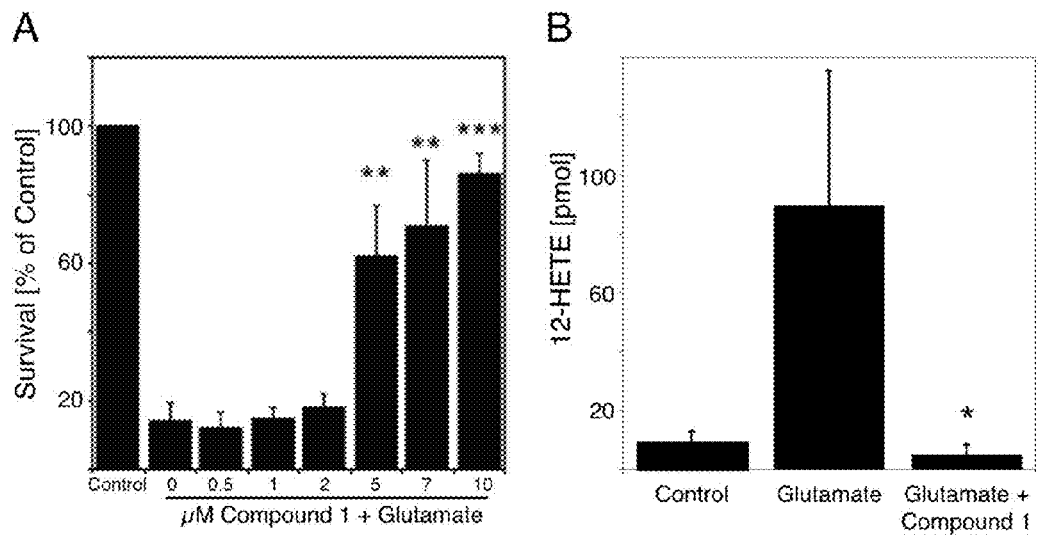
FIG. 3A is a plot showing protection against glutamate-induced HT-22 death by increasing amounts of 1 (p<0.01, *P<0.001 vs glutamate only).
FIG. 3B is a plot showing inhibition of 12-HETE in HT-22 cells by 10 μM of 1, following treatment with 5 mM glutamate (*P<0.05 vs glutamate only).

Upon testing of compound 1 in HT22 cells, a dose-dependent protection against oxidative glutamate toxicity (FIG. 3A) was found. To verify the on-target efficacy of 1, 12-HETE secreted from the cells was also measured. The increase in 12-HETE following glutamate treatment was completely reversed by incubation in the presence of 10 µM of 1 (FIG. 3B). These results suggest that 1 is capable of reaching its target in the cell and effectively inhibiting the mouse 12/15-LOX, albeit with lower affinity than seen against human 12/15-LOX in vitro ($IC_{50}$=200 nM).

Figure 4:
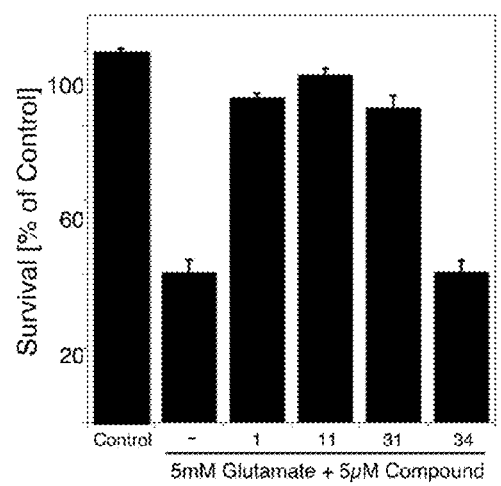
FIG. 4 is a plot showing cellular protection at 5 μM concentration in HT22 cells by 1 and some analogs. Despite not inhibiting human 12/15-LOX, 11 and 31 show similar protection to 1, indicating they inhibit the mouse enzyme, while 34 does not protect.

In addition to analogs that were active in vitro against human 12/15-LOX, several inactive analogs (11, 31, 34) were also tested in HT22 cells, with the goal of identifying a good negative control (FIG. 4). Surprisingly, 11 and 31 featured similar protective qualities at 5 µM concentration, suggesting they are able to inhibit the mouse homologue of 12/15-LOX, even though they are inactive against human 12/15-LOX. In contrast, 5 µM of 34 did not protect HT22 cells, suggesting it is inactive against both human and mouse 12/15-LOX and is a suitable negative control for 1. These data re-emphasize the importance of screening 12/15-LOX inhibitors against both human and mouse 12/15-LOX, since activity against one species does not guarantee activity or inactivity against the other.

Upon the determination that 1 was potent against both in vitro human 12/15-LOX and ex vivo mouse 12/15-LOX (HT-22 cell assay), the selectivity of a few of the top analogs against related human LOX isozymes (5-LOX, 12-LOX and 15-LOX-2) was then investigated. Of the four 12/15-LOX inhibitors tested, 1, 7, 8, and 32, all displayed excellent selectivity against all 3 isozymes ($IC_{50}$>50 µM, Table 4). Few compounds reported in the literature have achieved nM potency towards 12/15-LOX while maintaining excellent selectivity towards other isozymes. Moreover, none of these analogs displayed inhibition against cyclooxygenase-1 (COX-1) and/or COX-2 (<10% at 15 µM).

Mechanistic Investigations of Compound 1

Figure 7A:
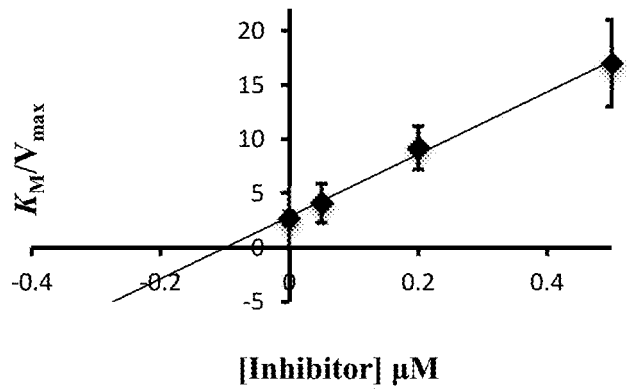
FIGS. 7A-7B are plots showing steady-state kinetics data for the determination of $K_i$ and $K_i'$ for 12/15-LOX with 1.
Figure 7B:
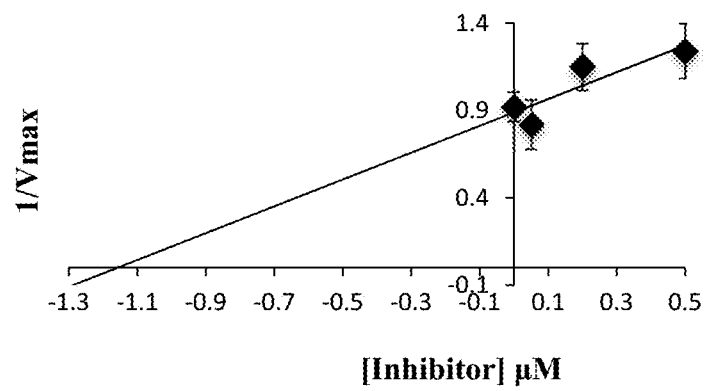
Figure 8:
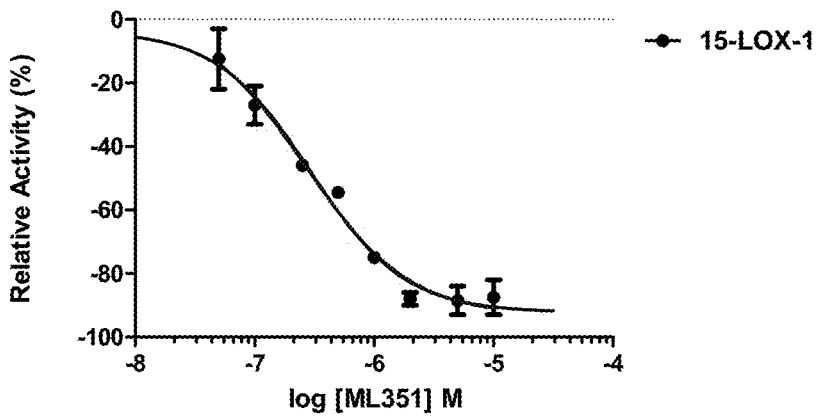
FIG. 8 is a dose response curves for probe ML351 showing inhibition of 15-LOX-1 in the UV-Vis assay.

LOX inhibitors are known to exhibit a variety of inhibitory mechanisms, such as chelative, reductive or competitive. The UV-Vis pseudoperoxidase activity assay was therefore performed on four selected analogs (1, 7, 8, 32, Table 4) to determine if the mechanism was reductive in nature. It was observed that the hydroperoxide product was not degraded, 12/15-LOX was not irreversibly inhibited and there was no elongation of the enzymatic lag phase (data not shown). These data are consistent with a non-reductive inhibitory mechanism. To investigate the nature of inhibition further, steady-state kinetics were performed using compound 1 by monitoring the formation of 15-HpETE as a function of substrate and inhibitor concentration in the presence of 0.01% Triton X-100. Replots of $K_M/V_{max}$ and $1/V_{max}$ versus inhibitor concentration yielded linear plots (FIG. 7), with $K_i$ equaling 0.1+/−0.002 µM and $K_i'$ equaling 1.2+/−0.02 µM. These parameters are defined as the equilibrium constants of dissociation from the catalytic ($K_i$) and secondary sites ($K_i'$), respectively. The $K_i$ is in good agreement with the $IC_{50}$ value and due to the greater than 10-fold difference between $K_i$ and $K_i'$, the secondary site was assume to be the allosteric site,[72,73] which is consistent with previous studies of 12/15-LOX inhibition.[56]

TABLE 4

Selectivity profiling of compound 1 and other top compounds.

| Analog | 12/15-LOX[a] | 15-LOX-2[a] | 12-LOX[a] | 5-LOX[a] | Redox Activity[b] |
|---|---|---|---|---|---|
| 1 | 0.02 | >100 | >100 | >50 | No |
| 7 | 0.46 | >100 | >100 | >100 | No |
| 8 | 0.81 | >100 | >100 | >50 | No |
| 32 | 0.55 | >100 | >40 | >50 | No |

In Table 4, [a]$IC_{50}$ values are reported in µM. [b] UV-vis pseudoperoxidase activity assay was performed on all the four selected analogs and no degradation of the hydroperoxide product was observed at 234 nm, indicating a non-reductive inhibitory mechanism.

In Vitro ADME and In Vivo PK Profile

The previously reported small molecule inhibitor for 12/15-LOX inhibition, ML094, demonstrated excellent potency and selectivity but lacked sufficient solubility, cell permeability and microsomal stability ($T_{1/2}$<2 mins).[56] Moreover, this compound possessed an essential ester moiety that could be susceptible to intracellular and plasma esterases, rendering it inactive and possibly limiting its utility in advanced biological models. Thus, the in vitro ADME (Table 5) and in vivo PK properties (Table 6) of 1 represent a vast improvement over the majority of compounds reported previously (vide infra). The majority of the compounds possess the low molecular weight (e.g. 249 Da), and a favorable log D (pH 7.4) between 2-3, which was obtained by Analiza Inc. using their "scaled-down shake flask lipophilicity method", yet most analogs have poor solubility. The aqueous kinetic solubility in PBS buffer (pH 7.4) was determined to be 1.2 µM, which is about 7 times the in vitro $IC_{50}$. Empirically, a vast improvement in the solubility in the 15-LOX assay buffer was observed (data not shown), which was encouraging and suggests that solubility was not a detrimental factor in the biochemical studies. Importantly, the compound demonstrated favorable PAMPA permeability (passive) and acceptable Caco-2 permeability of >1 (1.5 cm/s$^{-6}$) with no evidence of efflux (efflux ratio: 0.7) indicating the compound is not susceptible to the action of P-glycoprotein 1 (Pgp), a well-characterized ABC-transporter. Moreover, 1 was stable in various aqueous solutions (pH 2, pH 7.4, pH 9) (described somewhere else in the Example) and mouse plasma (Table 5). In addition, 1 exhibited minimal CYP inhibition of the 2D6 and 3A4 isoforms at 10.3% and 3.5% inhibition respectively. Microsomal stability appears to be species dependent with 1 possessing moderate stability to rat liver microsomes (18 minutes) while being less stable to mouse liver microsomes (5.5 mins). The compounds were completely stable in the absence of NADPH, suggesting a CYP-mediated degradation. Given the plan to test compound 1 in proof of concept mouse models of stroke, the inventors also obtained in vivo PK data on 1 (Table 6) and found a suitable formulation for 1 (10% Solutol, 10% Cremophor EL, 20% PEG400 in saline). As anticipated from the microsomal stability studies, 1 has a relatively fast half-life in both plasma and brain ($T_{1/2}$=~1 h), with a $C_{max}$ of 13.8 µM in plasma and 28.8 µM in brain. Encouragingly, 1 has a brain/plasma ratio of 2.8, which demonstrates favorable BBB permeability and suggested that this compound was suitable for in vivo proof of concept (POC) models of ischemic stroke (vide infra).

TABLE 5

ADME profile for Compound 1

| Compound | Kinetic Solubility (µM)[a] | Microsomal Stability $T_{1/2}$ (min)[b] | CYP 2D6 Inhibition @ 3 µM[c] | CYP 3A4 Inhibition @ 3 µM[d] | Permeability ($10^{-6}$ cm/s) | | Mouse Plasma Stability remaining at 2 hours |
|---|---|---|---|---|---|---|---|
| 1 | 1.2 | 18 (rat) 5.5 (mouse) | 10.30% | 3.50% | 723 (PAMPA) | 1.5 (Caco-2) | 100% |

In Table 5, all experiments were conducted at Pharmaron Inc. [a]In PBS buffer (pH 7.4). [b]Represents the stability in the presence of NADPH. The probe compound showed no degradation without NADPH present over a 1 hr period. [c]Dextromethorphan was used as the substrate. [d]Midazolam was used as the substrate.

TABLE 6

In vivo PK (mouse) at 30 mpk IP for Compound 1

| Compound | Tissue | $T_{1/2}$ | $T_{max}$ | $C_{max}$ (µM) | $AUC_{inf}$ (µM*h) | Brain/Plasma[b] |
|---|---|---|---|---|---|---|
| 1 | Plasma | 1.1 h | 0.25 h | 13.8 | 13 | 2.8 |
|   | Brain | 1 h | 0.5 h | 28.8 | 35.5 |   |

In Table 6, all experiments were conducted at Pharmaron Inc. using male CD1 mice (6-8 weeks of age). Data was collected in triplicate at 8 time points over a 24 h period. [a]Formulated as a solution (10% Solutol, 10% Cremophor EL, 20% PEG 400 in saline). [b]Brain to plasma ratio [$AUC_{last}$(brain)/$AUC_{last}$(plasma)].

Cell Activity and In Vivo Efficacy

After having established the SAR profile against recombinant human 12/15-LOX, determining the efficacy of 1 in the cellular mouse 12/15-LOX assay, and measuring its in vitro ADME/in vivo PK properties, its efficacy in mouse models of ischemic stroke was then determined. For these initial studies, the permanent focal ischemia model in mice was chosen, which has been shown to mimic the pathophysiological mechanisms following ischemic injury.[74] The advantage of this model is that it does not inflict surgical trauma, and has a low mortality compared to other methods. The thrombosis event in the middle cerebral artery (MCA) is induced by topical application of $FeCl_3$ to the intact dura mater, leading to a cortical infarct. Laser Doppler flowmetry is used to monitor blood flow reduction and infarct size is measured following sacrifice at 24 hours by staining of 1 mm thick brain slices with 2,3,5-triphenylterazolium hydrochloride (TTC). IP administration of 1 administered 2 hours after the induced ischemia resulted in a ~30% reduction in infarct size (p<0.01), demonstrating efficient neuroprotection in this mouse model of permanent focal ischemia (FIG. 5).

Conclusion

12/15-LOX contributes to neuronal cell death in oxidative stress models[38-44] and is also detrimental to not just neurons, but also to the brain vasculature after stroke,[45] via intracellular attack on mitochondria and translocation of the apoptosis-inducing factor (AIF) to the nucleus.[46-48] Moreover, the protein level of 12/15-LOX gradually increases over time after experimental stroke,[47] providing an opportunity for therapeutic intervention. Initial efforts to identify a stroke relevant 12/15-LOX inhibitor proved unsuccessful due to its inactivity in the mouse ex vivo model, either due to cellular inactivation or inactivity against mouse 12/15-LOX.[56] Fortunately, re-interrogation of the HTS data along with simultaneous cellular mouse 12/15-LOX screening revealed another 12/15-LOX inhibitor (1), with better "drug-like" properties and more importantly, mouse ex vivo activity. The initial medicinal chemistry efforts, described herein, provided important SAR to guide future investigations. The most significant loss of inhibition was observed at the 1-naphthyl position, where almost all substitutions resulted in significant loss in activity, with the exception of its bio-isosteric dichloro analogs (7 and 8), which only showed a slight decrease in activity. Modifications of the methyl group on the N-methyl side chain were not well tolerated either, indicating the straight chain, mono alkylated amine was critical for potency. Moreover, the only substitution tolerated for 1,3 oxazole core ring was the replacement with a 1,3 diazole (32), which resulted in a two-fold decrease in the potency. The cyanide group on the oxazole core was found to be essential, with modifications to this group completely abolishing activity. Subsequent selectivity studies of 1 and related analogs revealed that these compounds have minimal activity towards 5-LOX, 12-LOX, 15-LOX-2, COX-1 and COX-2.

Most importantly, 1 was active in both protecting mouse neuronal cells (HT22) and in reducing the infarct size of stroke-induced mice. This is a significant discovery because identifying therapeutically useful specific inhibitors of 12/15-LOX is not trivial due to the differences between the human and mouse 12/15-LOX isozymes. Interestingly, analogs of compound 1 (11 and 31) did not inhibit human 12/15-LOX, but protected HT22 cells against oxidative stress. These might work in mice to protect against experimental stroke, yet in human stroke, they would most likely fail, because of their inability to target human 12/15-LOX. The lessons to be drawn from this are that simply because a given inhibitor is selective for a LOX isoform in one species, its efficacy cannot be readily extrapolated to other species. Moreover, the LOX isotype involved in a given process cannot be reliably inferred from inhibitor experiments without taking into account the species from which the cells were derived.

In conclusion, compound 1 is the first highly selective 12/15-LOX inhibitor to be active against human 12/15-LOX and mouse 12/15-LOX, as seen by its effectiveness in the mouse stroke model. This critical quality of 1 is significant because it maintains the human 12/15-LOX selectivity, which is beneficial to a human therapeutic, but is also functional in a mouse stroke model, which is critical to developing its biological efficacy. Therefore, by using pipeline approach described herein, the inventors have identified a potent and selective inhibitor of human 12/15-LOX that is neuroprotective in a mouse model of stroke and therefore can be utilized in pre-clinical studies to develop it as a potential first-line stroke therapy.

Experimental Section

General Methods for Chemistry

All air or moisture sensitive reactions were performed under positive pressure of nitrogen with oven-dried glassware. Anhydrous solvents such as dichloromethane, N,N-dimethylforamide (DMF), acetonitrile, dioxan, dimethoxyethane, methanol and triethylamine were purchased from Sigma-Aldrich. Tetrakis and a 50% of solution of propylphosphonic anhydride (T3P®) in DMF or ethyl acetate were purchased from Strem chemicals and used as such. SiliaCat® Heterogeneous Catalyst DPP-Pd (Catalog # R390-100) was purchased from SiliCycle Inc. Preparative purification was performed on a Waters semi-preparative HPLC system using a Phenomenex Luna C18 column (5 micron, 30×75 mm) at a flow rate of 45 mL/min. The mobile phase consisted of acetonitrile and water (each containing 0.1% trifluoroacetic acid). A gradient of 10% to 50% acetonitrile over 8 minutes was used during the purification. Fraction collection was triggered by UV detection (220 nm). Analytical analysis was performed on an Agilent LC/MS (Agilent Technologies, Santa Clara, Calif.). Method 1: A 7 minute gradient of 4% to 100% Acetonitrile (containing 0.025% trifluoroacetic acid) in water (containing 0.05% trifluoroacetic acid) was used with an 8 minute run time at a flow rate of 1 mL/min. A Phenomenex Luna C18 column (3 micron, 3×75 mm) was used at a temperature of 50° C. Method 2: A 3 minute gradient of 4% to 100% Acetonitrile (containing 0.025% trifluoroacetic acid) in water (containing 0.05% trifluoroacetic acid) was used with a 4.5 minute run time at a flow rate of 1 mL/min. A Phenomenex Gemini Phenyl column (3 micron, 3×100 mm) was used at a temperature of 50° C. Method 3: Analysis was performed on an Agilent 1290 Infinity Series HPLC. UHPLC Long Gradient Equivalent 4% to 100% acetonitrile (0.05% trifluoroacetic acid) in water over 3.5 minutes run time of 4 minutes with a flow rate of 0.8 mL/min. A Phenomenex Kinetex 1.7 micron C18 column (2.1×100 mm) was used at a temperature of 50° C. Purity determination was performed using an Agilent Diode Array Detector for both Method 1, Method 2 and Method 3. Mass determination was performed using an Agilent 6130 mass spectrometer with electrospray ionization in the positive mode. $^1$H NMR spectra were recorded on Varian 400 MHz spectrometers. Chemical shifts are reported in ppm with undeuterated solvent (DMSO-$d_6$ at 2.49 ppm) as internal standard for DMSO-$d_6$ solutions. All of the analogs tested in the biological assays have purity greater than 95%, based on both analytical methods. High resolution mass spectrometry was recorded on Agilent 6210 Time-of-Flight LC/MS system. Confirmation of molecular formula was accomplished using electrospray ionization in the positive mode with the Agilent Masshunter software (version B.02).

Experimental Procedures

General Procedure for the Preparation of 5-Amino-2-Substituted Oxazole-4-Carbonitrile Intermediates (1i-18i,19)

A mixture of carboxylic acid (5.77 mmol, 1 eq.) and 2-aminomalononitrile.TsOH (5.77 mmol, 1 eq.) in ethyl acetate (15 mL) was added NEt$_3$ (17.32 mmol, 3 eq.) followed by a 50% solution of propylphosphonic anhydride (T$_3$P®) in ethyl acetate (14.44 mmol, 2.5 eq.). The reaction was allowed to stir at room temperature for 12 h and then diluted with ethyl acetate. The organic layer was successively washed with water, saturated bicarbonate solution and brine. The organic layer was then dried with MgSO$_4$, and concentrated under reduced pressure. The crude product was purified on a biotage Flash® system eluting with 50-100% ethyl acetate in hexanes containing 0.1% triethylamine to provide pure products.

General Procedure for the Preparation of 2-Substituted-5-(Methylamino)Oxazole-4-Carbonitrile (1-18)

A mixture of 5-amino-2-substituted oxazole-4-carbonitrile (1.79 mmol, 1 eq.), paraformaldehyde (0.11 g, 3.57 mmol, 2 eq.) and sodium methoxide (0.096 g, 1.79 mmol, 1 eq.) in methanol (10 mL) was stirred at 65° C. for 1 h until a clear mixture was obtained. The reaction mixture was cooled to room temperature and sodium borohydride (3.57 mmol, 2 eq.) was added slowly and stirred further at room temperature for 1 h. The crude product was extracted with ethyl acetate and successively washed with water and brine. The ethyl acetate layer was dried with MgSO$_4$, and concentrated under reduced pressure. The crude product was taken up in DMSO and purified on a reversed-phase HPLC system. Characterization data for key compounds is given below.

5-(Methylamino)-2-(naphthalen-1-yl)oxazole-4-carbonitrile (1-ML351)

This compound was prepared starting from 1-naphthoic acid and aminomalononitrile via intermediate 19 following the above general procedure. LC-MS Retention Time: (Method 1)=6.011 min and (Method 2)=2.42 min; $^1$H NMR (400 MHz, DMSO-$d_6$) δ 9.15 (dq, J=8.7 and 0.9 Hz, 1H), 8.44 (brs, 1H), 8.10-7.99 (m, 3H), 7.74-7.57 (m, 3H), 3.07-3.01 (m, 3H); $^{13}$C NMR (400 MHz, DMSO-$d_6$) δ 161.9, 161.9, 149.5, 134.1, 134.0, 131.2, 129.2, 128.3, 127.2, 127.2, 127.0, 126.9, 125.8, 125.8, 125.8, 125.7, 122.1, 116.5, 116.5, 84.1, 84.1, 84.1, 29.7, 29.7, 29.6; HRMS (ESI) m/z (M+H)$^+$ calcd. for $C_{15}H_{12}N_3O$, 250.0975. found 250.0975.

5-(Methylamino)-2-(naphthalen-2-yl)oxazole-4-carbonitrile TFA (2)

LC-MS Retention Time: (Method 3)=2.496 min and (Method 2)=3.556 min; $^1$H NMR (400 MHz, DMSO-$d_6$) δ 8.41 (d, J=5.0 Hz, 1H), 8.34 (d, J=1.7 Hz, 1H), 8.09-8.00 (m, 2H), 7.99-7.89 (m, 2H), 7.63-7.56 (m, 2H), 3.07-3.02 (m, 3H); HRMS (ESI) m/z (M+H)+ calcd. for $C_{15}H_{12}N_3O$, 250.0975. found 250.0980.

2-(Isoquinolin-5-yl)-5-(methylamino)oxazole-4-carbonitrile TFA (3)

LC-MS Retention Time: (Method 3)=1.228 min and (Method 2)=2.466 min; $^1$H NMR (400 MHz, DMSO-$d_6$) δ 9.49 (s, 1H), 9.04 (d, J=6.2 Hz, 1H), 8.68 (d, J=6.2 Hz, 1H), 8.55 (q, J=4.8 Hz, 1H), 8.31 (d, J=7.7 Hz, 2H), 7.85 (t, J=7.8 Hz, 1H), 3.05 (d, J=4.9 Hz, 3H); HRMS (ESI) m/z (M+H)+ calcd. for $C_{14}H_{11}N_4O$, 251.0927. found 251.0918.

5-(Methylamino)-2-(quinolin-5-yl)oxazole-4-carbonitrile TFA (4)

LC-MS Retention Time: (Method 1)=3.621 min and (Method 2)=2.582 min; $^1$H NMR (400 MHz, DMSO-$d_6$) δ

9.61-9.53 (m, 1H), 9.01 (dd, J=4.2, 1.7 Hz, 1H), 8.53 (q, J=4.9 Hz, 1H), 8.20-8.08 (m, 2H), 7.94-7.83 (m, 1H), 7.73 (dd, J=8.7, 4.2 Hz, 1H), 3.05 (d, J=4.9 Hz, 3H); HRMS (ESI) m/z (M+H)+ calcd. for $C_{14}H_{11}N_4O$, 251.0927. found 251.0938.

2-(Isoquinolin-6-yl)-5-(methylamino)oxazole-4-carbonitrile TFA (5)

LC-MS Retention Time: (Method 1)=3.259 min and (Method 2)=2.534 min; $^1H$ NMR (400 MHz, DMSO-$d_6$) δ 9.50 (s, 1H), 8.61 (dd, J=5.5, 3.8 Hz, 2H), 8.45 (d, J=1.6 Hz, 1H), 8.33 (d, J=8.6 Hz, 1H), 8.20-8.11 (m, 2H), 3.06 (d, J=4.9 Hz, 3H); HRMS (ESI) m/z (M+H)+ calcd. for $C_{14}H_{11}N_4O$, 251.0927. found 251.0928.

5-(Methylamino)-2-(quinoxalin-5-yl)oxazole-4-carbonitrile TFA (6)

LC-MS Retention Time: (Method 3)=1.862 min and (Method 2)=2.95 min; $^1H$ NMR (400 MHz, DMSO-$d_6$) δ 9.04-8.96 (m, 2H), 8.58 (d, J=5.0 Hz, 1H), 8.37 (d, J=1.8 Hz, 1H), 8.29-8.17 (m, 2H), 3.05 (dd, J=5.0, 0.6 Hz, 1H); HRMS (ESI) m/z (M+H)+ calcd. for $C_{13}H_{10}N_5O$, 252.088. found 252.0883.

2-(2,3-Dichlorophenyl)-5-(methylamino)oxazole-4-carbonitrile TFA (7)

This compound was prepared starting from 2,3-benzoic acid and aminomalononitrile via intermediate 7i following the above general procedure. LC-MS Retention Time: (Method 3)=2.639 min and (Method 2)=3.559 min; $^1H$ NMR (400 MHz, DMSO-$d_6$) δ 8.50 (q, J=4.9 Hz, 1H), 7.83 (ddd, J=7.9, 1.5, 0.4 Hz, 1H), 7.78 (ddd, J=8.1, 1.6, 0.4 Hz, 1H), 7.54-7.46 (m, 1H), 2.99 (d, J=4.9 Hz, 3H); HRMS (ESI) m/z (M+H)+ calcd. for $C_{11}H_8Cl_2N_3O$, 269.0039. found 267.0031.

2-(3,4-Dichlorophenyl)-5-(methylamino)oxazole-4-carbonitrile TFA (8)

This compound was prepared starting from 3,4-benzoic acid and aminomalononitrile via intermediate 8i following the above general procedure. LC-MS Retention Time: (Method 2)=3.737 min; $^1H$ NMR (400 MHz, DMSO-$d_6$) δ 8.48 (q, J=4.9 Hz, 1H), 7.95 (td, J=1.8, 0.7 Hz, 1H), 7.80-7.72 (m, 2H), 3.09-2.91 (m, 3H); HRMS (ESI) m/z (M+H)+ calcd. for $C_{11}H_8Cl_2N_3O$, 269.0039. found 267.0043.

2-(2,3-Dihydrobenzo[b][1,4]dioxin-6-yl)-5-(methylamino)oxazole-4-carbonitrile TFA (9)

LC-MS Retention Time: (Method 1)=4.905 min and (Method 2)=3.323 min; $^1H$ NMR (400 MHz, DMSO-$d_6$) δ 8.24 (q, J=4.9 Hz, 1H), 7.34-7.15 (m, 2H), 6.97 (dd, J=8.5, 0.4 Hz, 1H), 4.29 (d, J=1.0 Hz, 4H), 2.96 (d, J=4.9 Hz, 3H); HRMS (ESI) m/z (M+H)+ calcd. for $C_{13}H_{12}N_3O_3$, 258.873. found 258.875.

2-(Benzo[d][1,3]dioxol-5-yl)-5-(methylamino)oxazole-4-carbonitrile TFA (10)

LC-MS Retention Time: (Method 3)=2.019 min and (Method 2)=3.338 min; $^1H$ NMR (400 MHz, DMSO-$d_6$) δ 8.24 (q, J=5.0 Hz, 1H), 7.45-7.18 (m, 2H), 7.03 (dt, J=8.1, 0.5 Hz, 1H), 6.10 (d, J=0.6 Hz, 2H), 2.97 (d, J=5.0 Hz, 3H); HRMS (ESI) m/z (M+H)+ calcd. for $C_{12}H_{10}N_3O_3$, 244.0717. found, 244.0712.

2-([1,1'-Biphenyl]-4-yl)-5-(methylamino)oxazole-4-carbonitrile TFA (11)

This compound was prepared starting from 4-phenylbenzoic acid and aminomalononitrile via intermediate 111 following the above general procedure. LC-MS Retention Time: (Method 1)=6.215 min and (Method 2)=3.708 min; $^1H$ NMR (400 MHz, DMSO-$d_6$) δ 8.38 (q, J=4.9 Hz, 1H), 7.92-7.79 (m, 4H), 7.76-7.68 (m, 2H), 7.53-7.46 (m, 2H), 7.43-7.37 (m, 1H), 3.01 (dd, J=4.8, 0.6 Hz, 3H); HRMS (ESI) m/z (M+H)+ calcd. for $C_{17}H_{14}N_3O$, 276.1131. found 276.1143.

2-(1H-indol-6-yl)-5-(methylamino)oxazole-4-carbonitrile TFA (13)

LC-MS Retention Time: (Method 3)=2.004 min and (Method 2)=3.308 min; $^1H$ NMR (400 MHz, DMSO-$d_6$) δ 11.38 (s, 1H), 8.22 (q, J=4.9 Hz, 1H), 7.83 (dq, J=1.4, 0.7 Hz, 1H), 7.63 (dt, J=8.3, 0.7 Hz, 1H), 7.56-7.41 (m, 2H), 6.49 (ddd, J=3.0, 1.9, 0.9 Hz, 1H), 3.00 (d, J=5.0 Hz, 3H); HRMS (ESI) m/z (M+H)+ calcd. for $C_{13}H_{11}N_4O$, 239.0927. found 239.0934.

2-(1H-indol-3-yl)-5-(methylamino)oxazole-4-carbonitrile TFA (14)

LC-MS Retention Time: (Method 3)=1.938 min and (Method 2)=3.236 min; $^1H$ NMR (400 MHz, DMSO-$d_6$) δ 11.73 (d, J=13.4 Hz, 1H), 8.10-7.95 (m, 2H), 7.89 (dd, J=10.7, 2.8 Hz, 1H), 7.52-7.44 (m, 1H), 7.26-7.12 (m, 2H), 2.99 (d, J=5.0 Hz, 3H); HRMS (ESI) m/z (M+H)+ calcd. for $C_{13}H_{11}N_4O$, 239.0927. found 239.0923.

Synthesis of 5-(Azetidin-3-ylamino)-2-(naphthalen-1-yl)oxazole-4-carbonitrile TFA (31)

A mixture of 5-chloro-2-(naphthalen-1-yl)oxazole-4-carbonitrile (19a) (0.25 mmol, 1 eq.) and 1-Boc-3-(amino)azetidine (1 mmol, 4 eq) in THF was heated to reflux for 0.5 h. The reaction mixture was then cooled and the solvent was removed by forced air. The crude product was taken up in DMSO and purified via reversed phase preparative HPLC. This pure product was suspended in dichloromethane (2 mL) and treated with TFA (0.5 mL). After stirring for 0.5 h at room temperature, the volatiles were removed by forced air. The crude product was taken up in DMSO and purified on a preparative HPLC to give pure product (31) as TFA salt. LC-MS Retention Time: (Method 1)=4.078 min and $t_2$ (Method 2)=3.812 min; $^1H$ NMR (400 MHz, DMSO-$d_6$) δ 9.29 (s, 1H), 9.12 (d, J=8.6 Hz, 1H), 8.90 (s, 1H), 8.14-8.01 (m, 2H), 7.75-7.59 (m, 3H), 4.77 (p, J=7.0, 6.0 Hz, 1H), 4.32-4.18 (m, 2H), 4.18-4.08 (m, 2H); HRMS (ESI) m/z (M+H)+ calcd. for $C_{17}H_{15}N_4O$, 291.1252. found 291.125.

Synthesis of (methylamino)-2-(naphthalen-1-yl)thiazole-4-carbonitrile TFA (32)

A mixture of 2-bromothiazole-4-carbonitrile (1.85 g, 9.79 mmol, 1 eq.), naphthalen-1-ylboronic acid (2.52 g, 14.68 mmol, 1.5 eq.), 2 M sodium carbonate (12.23 mL, 24.47 mmol, 2.5 eq.) and Pd(PPh$_3$)$_4$ (1.11 g, 0.979 mmol, 10 mol %) in dimethoxy ethane (20 mL) was degassed with argon then heated under microwave for 45 minutes at 150° C. The reaction mixture was concentrated and taken up in dichloromethane then stirred with palladium scavenger resin and filtered through celite. The crude product obtained after evaporating the solvent was purified on a Biotage® flash system eluting with 10% ethyl acetate in hexanes to obtain 1.52 g (Yield: 66%) of 2-(naphthalen-1-yl)thiazole-4-carbonitrile (32a) as white solid.

A solution of the above 2-(naphthalen-1-yl)thiazole-4-carbonitrile 32a (0.5 g, 2.12 mmol, 1 eq.) in THF (10 mL) was added a 2 M THF solution of LDA (1.16 mL, 2.33 mmol, 1.1 eq.) dropwise at −78° C. After stirring for 30 minutes at −78° C., perchloroethane (0.551 g, 2.33 mmol, 1.1 eq) was added in one portion and allowed to warm to room temperature over 4 h. The reaction was then quenched with saturated ammonium chloride and extracted with ethyl acetate. The organic layer was washed with water and brine. The ethyl acetate layer was subsequently dried over MgSO$_4$ and filtered. The crude product obtained after concentrating under diminished pressure was purified on a Biotage® flash system eluting with 50% CH$_2$Cl$_2$ in hexanes to furnish 4.5 g (Yield: 79%) of 5-chloro-2-(naphthalen-1-yl)thiazole-4-carbonitrile 32b as a white solid. $^1$H NMR (400 MHz, DMSO-d$_6$) δ 8.67 (d, J=8.4 Hz, 1H), 8.20 (d, J=8.3 Hz, 1H), 8.13-8.05 (m, 1H), 7.94 (dd, J=7.3, 1.3 Hz, 1H), 7.69 (dddd, J=14.7, 9.3, 6.9, 1.7 Hz, 3H).

A mixture of 5-chloro-2-(naphthalen-1-yl)thiazole-4-carbonitrile 32b (0.2 g, 0.739 mmol, 1 eq.) and a 2 M THF solution of methylamine (1.9 mL, 3.69 mmol, 5 eq) in 2-propanol (1 mL) was heated via microwave for 30 min at 120° C. The crude product obtained after evaporation of the solvent was taken up in DMSO and purified by reversed phase preparative HPLC to obtain 5-(methylamino)-2-(naphthalen-1-yl)thiazole-4-carbonitrile (32) as TFA salt. LC-MS Retention Time: (Method 3)=2.814 min and (Method 2)=3.756 min; $^1$H NMR (400 MHz, DMSO-d$_6$) δ 8.88 (ddt, J=8.5, 1.4, 0.8 Hz, 1H), 8.17 (q, J=4.7 Hz, 1H), 8.07-7.98 (m, 2H), 7.77 (dd, J=7.2, 1.2 Hz, 1H), 7.71-7.53 (m, 3H), 3.01 (d, J=4.7 Hz, 3H); HRMS (ESI) m/z (M+H)$^+$ calcd. for C$_{15}$H$_{12}$N$_3$S, 266.0754. found 266.0746.

Synthesis of N-methyl-5-(naphthalen-1-yl)oxazol-2-amine (34)

A solution of 5-(naphthalen-1-yl)oxazole-4-carbonitrile 34a (0.9 g, 4.09 mmol, 1 eq.) in THF (15 mL) was added a 1 M THF solution of LHMDS (4.5 mL, 4.5 mmol, 1.1 eq.) dropwise at −78° C. The reaction mixture was stirred for 30 minutes at −78° C. then perchloroethane (1.064 g, 4.5 mmol, 1.1 eq.) was added in one portion and allowed to reach room temperature over 4 h. The reaction mixture was quenched with saturated ammonium chloride and extracted with ethyl acetate. The organic layer was washed with water and brine then dried over magnesium sulfate, filtered and concentrated under diminished pressure. The crude product was purified on a Biotage® flash system eluting with 10% ethyl acetate in hexanes to furnish 0.75 g (Yield: 72%) of 2-chloro-5-(naphthalen-1-yl)oxazole-4-carbonitrile 34b as white solid.

A solution of 2-chloro-5-(naphthalen-1-yl)oxazole-4-carbonitrile 34b (0.1 g, 0.393 mmol, 1 eq.) in THF (1 mL) was added a 2 M solution of methanamine in THF (1.0 mL, 1.98 mmol, 5 eq) and stirred at 65° C. for 1 h in a sealed tube. The solvent was removed by forced air to obtain a crude solid. This crude product was taken up in DMSO and purified on a preparative HPLC to obtain pure product (34) as TFA salt. LC-MS Retention Time: (Method 1)=5.509 min and (Method 2)=3.498 min; $^1$H NMR (400 MHz, DMSO-d$_6$) δ 8.17-7.96 (m, 4H), 7.81 (dd, J=7.3, 1.3 Hz, 1H), 7.71-7.59 (m, 3H), 2.88 (d, J=4.8 Hz, 3H); FIRMS (ESI) m/z (M+H)$^+$ calcd. for C$_{15}$H$_{12}$N$_3$O, 250.0975. found 250.0979.

Figure 1D:
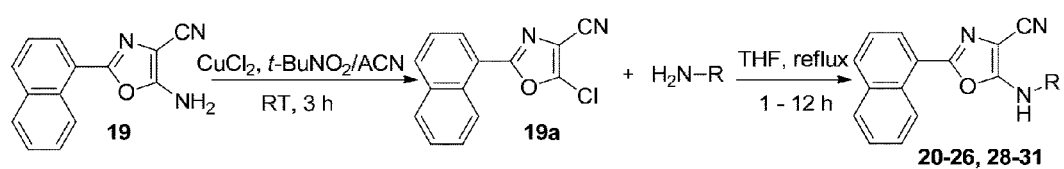

General Procedure for the Synthesis of Compounds 20-26 and 28-31 (FIG. 1D)

A suspension of copper(II) chloride (13.10 g, 97 mmol, 2.05 eq.) in acetonitrile (200 mL) was added t-butyl nitrite (13.82 mL, 105 mmol, 2.2 eq.) followed by 5-amino-2-(naphthalen-1-yl)oxazole-4-carbonitrile (11.18 g, 47.5 mmol, 1 eq.) in portions at room temperature. The reaction mixture was stirred for 3 h then concentrated and extracted with ethyl acetate. The organic layer was successively washed with 1% HCl, water and brine. The organic layer was dried over MgSO$_4$, filtered and concentrated under diminished pressure. The crude product was purified on a Biotage® flash system eluting with 40% CH$_2$Cl$_2$ in hexanes to furnish 4.2 g (Yield: 35%) of 5-chloro-2-(naphthalen-1-yl)oxazole-4-carbonitrile (19a) as white solid. $^1$H NMR (400 MHz, DMSO-d6) δ 8.99 (dq, J=8.6, 0.9 Hz, 1H), 8.27-8.18 (m, 2H), 8.09 (ddt, J=8.1, 1.3, 0.6 Hz, 1H), 7.79-7.63 (m, 3H).

A mixture of 5-chloro-2-(naphthalen-1-yl)oxazole-4-carbonitrile (19a) (0.25 mmol, 1 eq.) and appropriate amine (10 eq) in THF was heated to reflux for 0.5 h. The reaction mixture was then cooled and the solvent was removed by forced air. The crude product was taken up in DMSO and purified via reversed phase preparative HPLC to obtain pure products as TFA salts.

5-(Ethylamino)-2-(naphthalen-1-yl)oxazole-4-carbonitrile TFA (21)

LC-MS Retention Time: (Method 1)=6.278 min and (Method 2)=3.724 min; $^1$H NMR (400 MHz, DMSO-d$_6$) δ 9.14 (ddq, J=8.6, 1.3, 0.7 Hz, 1H), 8.55 (t, J=5.6 Hz, 1H), 8.12-8.00 (m, 3H), 7.75-7.57 (m, 3H), 3.47-3.41 (m, 2H), 1.26 (td, J=7.2, 0.6 Hz, 3H); HRMS (ESI) m/z (M+H)$^+$ calcd. for C$_{16}$H$_{14}$N$_3$O, 264.1131. found 264.113.

2-(Naphthalen-1-yl)-5-(propylamino)oxazole-4-carbonitrile TFA (22)

LC-MS Retention Time: (Method 1)=6.586 min and (Method 2)=3.819 min; $^1$H NMR (400 MHz, DMSO-d$_6$) δ 9.15 (ddt, J=9.1, 1.3, 0.7 Hz, 1H), 8.59 (t, J=5.8 Hz, 1H), 8.12-7.98 (m, 3H), 7.75-7.57 (m, 3H), 3.38-3.35 (m, 2H), 1.71-1.60 (m, 2H), 0.96 (td, J=7.4, 0.5 Hz, 3H); HRMS (ESI) m/z (M+H)$^+$ calcd. for C$_{17}$H$_{16}$N$_3$O, 278.1288. found 278.1289.

5-(Butylamino)-2-(naphthalen-1-yl)oxazole-4-carbonitrile TFA (23)

LC-MS Retention Time: (Method 3)=2.496 min and (Method 2)=3.909 min; $^1$H NMR (400 MHz, DMSO-d$_6$) δ 9.18-9.11 (m, 1H), 8.57 (t, J=5.9 Hz, 1H), 8.10-7.99 (m, 3H), 7.74-7.58 (m, 3H), 3.45-3.38 (m, 2H), 1.68-1.56 (m, 2H), 1.48-1.33 (m, 2H), 0.94 (t, J=7.4 Hz, 3H); HRMS (ESI) m/z (M+H)$^+$ calcd. for C$_{18}$H$_{18}$N$_3$O, 292.1444. found 292.1453.

2-(Naphthalen-1-yl)-5-(pentylamino)oxazole-4-carbonitrile TFA (24)

LC-MS Retention Time: (Method 3)=2.496 min and (Method 2)=3.909 min; $^1$H NMR (400 MHz, DMSO-d$_6$) δ

9.15 (ddt, J=8.7, 1.4, 0.8 Hz, 1H), 8.57 (t, J=5.8 Hz, 1H), 8.10-7.96 (m, 3H), 7.73-7.52 (m, 3H), 3.43-3.30 (m, 2H), 1.71-1.58 (m, 2H), 1.45-1.26 (m, 4H), 0.96-0.82 (m, 3H); HRMS (ESI) m/z (M+H)$^+$ calcd. for $C_{19}H_{20}N_3O$, 306.1601. found 306.1609.

5-(Allylamino)-2-(naphthalen-1-yl)oxazole-4-carbonitrile TFA (25)

LC-MS Retention Time: (Method 2)=3.534 min; $^1$H NMR (400 MHz, DMSO-d$_6$) δ 10.30 (s, 1H), 8.26-8.12 (m, 1H), 8.13-7.95 (m, 1H), 7.78 (dd, J=7.1, 1.2 Hz, 1H), 7.74-7.54 (m, 4H), 5.99 (ddt, J=17.2, 10.2, 7.2 Hz, 1H), 5.63-5.47 (m, 2H), 3.21 (dt, J=7.3, 1.1 Hz, 2H); HRMS (ESI) m/z (M+H)$^+$ calcd. for $C_{17}H_{14}N_3O$, 276.1131. found 276.1142.

5-(Isopropylamino)-2-(naphthalen-1-yl)oxazole-4-carbonitrile TFA (26)

LC-MS Retention Time: (Method 1)=6.553 min and (Method 2)=3.82 min; $^1$H NMR (400 MHz, DMSO-d$_6$) δ 9.15 (dq, J=8.6, 0.9 Hz, 1H), 8.51 (d, J=7.9 Hz, 1H), 8.11-7.96 (m, 3H), 7.74-7.58 (m, 3H), 3.91 (dq, J=7.8, 6.4 Hz, 1H), 1.29 (d, J=6.5 Hz, 6H); HRMS (ESI) m/z (M+H)$^+$ calcd. for $C_{17}H_{16}N_3O$, 278.1288. found 278.1301.

5-(Benzylamino)-2-(naphthalen-1-yl)oxazole-4-carbonitrile TFA (28)

LC-MS Retention Time: (Method 3)=2.975 min and t$_2$ (Method 2)=3.857 min; $^1$H NMR (400 MHz, DMSO-d$_6$) δ 9.14 (t, J=6.2 Hz, 1H), 9.10-9.04 (m, 1H), 8.10-7.96 (m, 3H), 7.71-7.54 (m, 3H), 7.49-7.35 (m, 4H), 7.34-7.25 (m, 1H), 4.61 (d, J=6.2 Hz, 2H); HRMS (ESI) m/z (M+H)$^+$ calcd. for $C_{21}H_{16}N_3O$, 326.1288. found 326.1295.

2-(Naphthalen-1-yl)-5-(phenylamino)oxazole-4-carbonitrile TFA (29)

LC-MS Retention Time: (Method 1)=6.759 min and (Method 2)=3.875 min; $^1$H NMR (400 MHz, DMSO-d$_6$) δ 9.00-8.98 (m, 1H), 8.25-8.25 (m, 2H), 8.15-8.02 (m, 3H), 7.80-7.60 (m, 5H), 7.47-7.37 (m, 2H); HRMS (ESI) m/z (M+Na)$^+$ calcd. for $C_{20}H_{14}N_3O$, 334.0955. found 334.0951.

2-(Naphthalen-1-yl)-5-(oxetan-3-ylamino)oxazole-4-carbonitrile TFA (30)

LC-MS Retention Time: (Method 3)=2.484 min and (Method 2)=3.405 min; $^1$H NMR (400 MHz, DMSO-d$_6$) δ 9.31 (d, J=6.1 Hz, 1H), 9.12 (dt, J=8.9, 1.0 Hz, 1H), 8.14-7.98 (m, 3H), 7.74-7.58 (m, 3H), 4.95-4.82 (m, 3H), 4.69-4.61 (m, 2H); HRMS (ESI) m/z (M+H)$^+$ calcd. for $C_{17}H_{14}N_3O_2$, 292.1081. found 292.1088.

N-methyl-5-(naphthalen-1-yl)oxazol-2-amine (33)

Figure 1E:
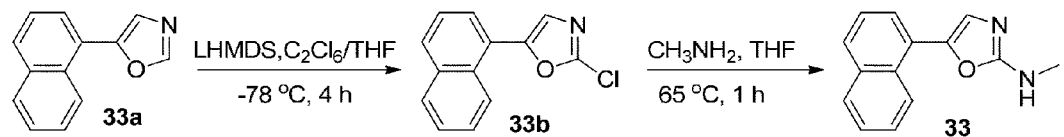

For synthesis scheme, see FIG. 1E. A solution of 5-(naphthalen-1-yl)oxazole 33a (0.5 g, 2.56 mmol, 1 eq.) in THF (15 mL) was added a 1 M THF solution of LHMDS (2.82 mL, 2.82 mmol, 1.1 eq.) dropwise at −78° C. The reaction mixture was stirred for 30 minutes at −78° C. then perchloroethane (0.667 g, 2.82 mmol, 1.1 eq.) was added in one portion and allowed to reach room temperature over 4 h. The reaction mixture was quenched with saturated ammonium chloride and extracted with ethyl acetate. The organic layer was washed with water and brine then dried over magnesium sulfate, filtered and concentrated under diminished pressure. The crude product was purified on a Biotage® flash system eluting with 10% ethyl acetate in hexanes to furnish 0.54 g (Yield: 92%) of 2-chloro-5-(naphthalen-1-yl) oxazole 33b as white solid. A solution of 2-chloro-5-(naphthalen-1-yl)oxazole 33b (0.1 g, 0.435 mmol, 1 eq.) in THF (1 mL) was added a 2 M solution of methanamine in THF (1.09 mL, 2.18 mmol, 5 eq.) and stirred at 65° C. for 1 h in a sealed tube. The solvent was removed by forced air to obtain a crude solid. This crude product was taken up in DMSO and purified on a preparative HPLC to obtain N-methyl-5-(naphthalen-1-yl)oxazol-2-amine (33) as TFA salt. LC-MS Retention Time: (Method 3)=1.593 min and (Method 2)=2.831 min; $^1$H NMR (400 MHz, DMSO-d$_6$) δ 8.64 (s, 1H), 8.32-8.23 (m, 1H), 8.05-7.93 (m, 2H), 7.74-7.50 (m, 6H), 2.95 (s, 3H); HRMS (ESI) m/z (M+H)$^+$ calcd. for $C_{14}H_{13}N_2O$, 225.1022. found 225.1032.

N-methyl-5-(naphthalen-1-yl)-1,3,4-oxadiazol-2-amine (35)

Figure 1F:
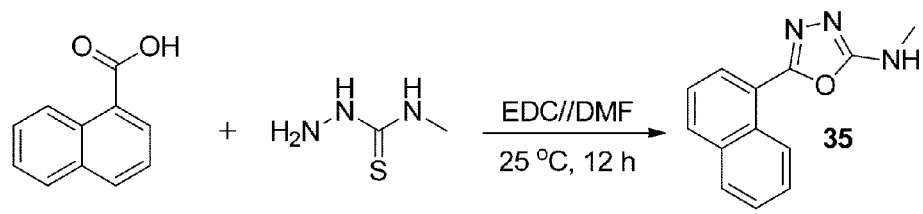

For synthesis scheme, see FIG. 1F. A mixture of 1-naphthoic acid (0.2 g, 1.16 mmol, 1 eq.), N-methylhydrazinecarbothioamide (0.122 g, 1.16 mmol, 1 eq.) and EDC (0.668 g, 3.48 mmol, 3 eq.) in DMF (3 mL) was stirred at room temperature for 12 h. The reaction mixture was filtered and purified on a HPLC. LC-MS Retention Time: (Method 3)=1.905 min and (Method 2)=3.048 min; $^1$H NMR (400 MHz, DMSO-d$_6$) δ 9.11 (ddq, J=8.7, 1.5, 0.7 Hz, 1H), 8.14-7.93 (m, 3H), 7.78-7.50 (m, 4H), 2.92 (dd, J=4.9, 0.6 Hz, 3H); HRMS (ESI) m/z (M+H)$^+$ calcd. for $C_{13}H_{12}N_3O$, 226.0975. found 226.0976.

N-methyl-5-(naphthalen-1-yl)-1,3,4-thiadiazol-2-amine (36)

Figure 1G:
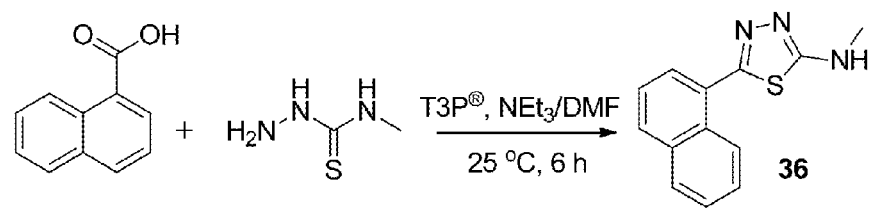

For synthesis scheme, see FIG. 1G. A solution of 1-naphthoic acid (0.1 g, 0.581 mmol, 1 eq.), N-methylhydrazinecarbothioamide (0.061 g, 0.581 mmol, 1 eq.) in DMF (1 mL) was added triethylamine (0.24 mL, 1.74 mmol, 3 eq.) followed by a 50% solution of propylphosphonic anhydride (T$_3$P) (0.92 g, 1.45 mmol, 2.5 eq.) dropwise. The reaction mixture was stirred at room temperature for 6 h then filtered through a celite plug. The crude product was purified via reversed phase preparative HPLC. LC-MS Retention Time: (Method 3)=1.852 min and (Method 2)=2.972 min; $^1$H NMR (400 MHz, DMSO-d$_6$) δ 8.81-8.74 (m, 1H), 8.09-7.94 (m, 3H), 7.74 (dd, J=7.2, 1.2 Hz, 1H), 7.68-7.56 (m, 3H), 2.98 (d, J=4.1 Hz, 3H); HRMS (ESI) m/z (M+H)$^+$ calcd. for $C_{13}H_{12}N_3S$, 242.0746. found 242.0751.

Methyl 5-(methylamino)-2-(naphthalen-1-yl)oxazole-4-carboxylate (37)

Figure 1H:
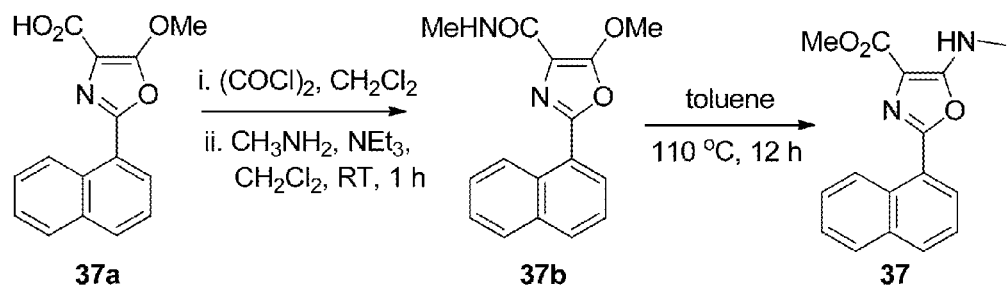

For synthesis scheme, see FIG. 1H. A suspension of 5-methoxy-2-(naphthalen-1-yl)oxazole-4-carboxylic acid 37a (3.6 g, 13.37 mmol, 1 eq.) in dichloromethane (50 mL) was added few drops of DMF and cooled in an ice bath. To the cold suspension was added oxalyl chloride (1.8 mL, 20.06 mmol, 1.5 eq.) dropwise. The reaction mixture was stirred at room temperature for 2 h. Excess solvent was evaporated under diminished pressure and the product was dried under vacuum. The crude solid was re-dissolved in dichloromethane (25 mL) and a 2 M solution of methanamine in THF (8 mL, 16.04 mmol) was added followed by triethyl amine (2.80 mL, 20.06 mmol) upon cooling. The reaction mixture was stirred at room temperature for 1 h then concentrated and purified on a Biotage® flash system eluting with 50% ethyl acetate in hexanes to furnish 2.2 g (Yield: 58%) of 5-methoxy-N-methyl-2-(naphthalen-1-yl)oxazole-4-carboxamide (37b) as yellow solid. A portion of this yellow solid (0.25 g, 0.886 mmol) was heated to reflux in toluene over 12 h. After completion of the reaction, the solvent was removed by forced air. The crude product was taken up in DMSO (2 mL) and purified via reversed phase HPLC. LC-MS Retention Time: (Method 1)=5.947 min and (Method 2)=3.647 min; $^1$H NMR (400 MHz, DMSO-$d_6$) δ 9.33 (ddq, J=8.7, 1.4, 0.7 Hz, 1H), 8.11 (dt, J=7.5, 0.8 Hz, 1H), 8.06-7.98 (m, 2H), 7.73-7.67 (m, 1H), 7.66-7.57 (m, 2H), 7.53 (q, J=4.9 Hz, 1H), 3.78 (d, J=0.6 Hz, 3H), 3.09 (dd, J=5.0, 0.6 Hz, 3H); HRMS (ESI) m/z (M+H)$^+$ calcd. for $C_{16}H_{15}N_2O_3$, 283.1077. found 283.1085.

Methyl 5-(methylamino)-2-(naphthalen-1-yl)thiazole-4-carboxylate (38)

Figure 1I:
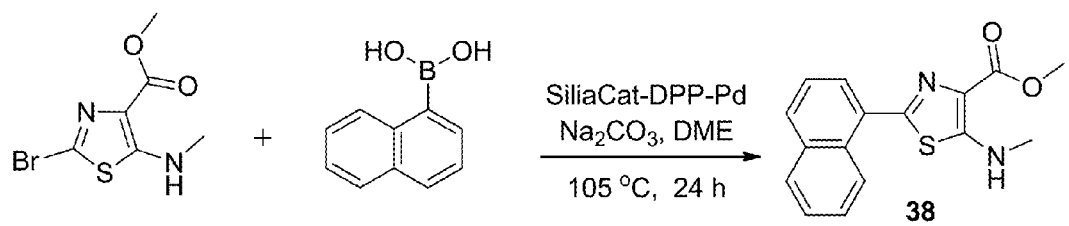

For synthesis scheme, see FIG. 1I. To a suspension of methyl 2-bromo-5-(methylamino)thiazole-4-carboxylate (1.55 g, 6.17 mmol, 1 eq.), naphthalen-1-ylboronic acid (2.12 g, 12.35 mmol, 2 eq.), SiliaCat-DPP-Pd (2.0 g, 0.309 mmol, 5 mol %) (purchased from silicycle, catalog # R390-100) in dimethoxyethane (30 mL) was added a 2 M solution of sodium carbonate in water (9.3 mL, 18.52 mmol, 3 eq.). The reaction mixture was bubbled with argon for 5 minutes and then stirred at 105° C. for 24 h. The reaction mixture was concentrated and taken up in dichloromethane and stirred with palladium scavenger resin. After filtering through celite and removal of the solvent, a portion of the crude product was purified on HPLC. LC-MS Retention Time: (Method 3)=2.793 min and (Method 2)=3.781 min; $^1$H NMR (400 MHz, DMSO-$d_6$) δ 9.01 (dd, J=8.2, 1.6 Hz, 1H), 8.08-7.97 (m, 2H), 7.88-7.74 (m, 2H), 7.72-7.53 (m, 3H), 3.82 (s, 3H), 3.04 (d, J=4.9 Hz, 3H); HRMS (ESI) m/z (M+H)$^+$ calcd. for $C_{16}H_{15}N_2O_2S$, 299.0849. found 299.0841.

2-(Methylamino)-6-(naphthalen-1-yl)nicotinonitrile (39)

Figure 1J:
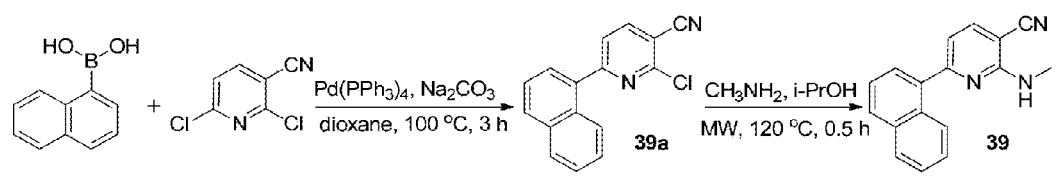

For synthesis scheme, see FIG. 1J. A mixture of 2,6-dichloronicotinonitrile (0.500 g, 2.89 mmol, 1 eq.), naphthalen-1-ylboronic acid (0.522 g, 3.03 mmol, 1.05 eq.) and a solution of sodium carbonate in 3 mL of water (0.680 g, 8.09 mmol, 2.8 eq.) in dioxane (12 mL) was bubbled with argon for 5 minutes. Pd(PPh$_3$)$_4$ (0.167 g, 0.145 mmol, 5 mol %) was then added and heated to reflux under nitrogen for 3 h. The reaction mixture was then stirred with palladium scavenger resin and filtered through celite. The filtrate was concentrated and purified on a Biotage® flash system eluting with 20% ethyl acetate in hexanes to give 0.45 g (Yield: 59%) of 39a. The above 2-chloro-6-(naphthalen-1-yl)nicotinonitrile (0.12 g, 0.453 mmol) (39a) and a 2 M THF solution of methanamine (1.13 ml, 2.27 mmol) in 2-iPrOH (1 mL) was heated in a MW for 30 min at 120° C. The crude product obtained upon concentration was taken up in DMSO and purified via reversed phase HPLC to obtain pure 39 as a TFA salt. LC-MS Retention Time: (Method 3)=1.803 min and (Method 2)=3.796 min; $^1$H NMR (400 MHz, DMSO-$d_6$) δ 8.26-8.17 (m, 1H), 8.15-7.92 (m, 3H), 7.76-7.48 (m, 4H), 7.25 (q, J=4.6 Hz, 1H), 6.91 (d, J=7.8 Hz, 1H), 2.88 (d, J=4.5 Hz, 3H); HRMS (ESI) m/z (M+H)$^+$ calcd. for $C_{17}H_{14}N_3$, 260.1182. found 260.1172.

N-methyl-4-(naphthalen-1-yl)pyrimidin-2-amine (40)

This compound was synthesized following the protocol used for compound 39 to obtain pure product 40 as a TFA salt after HPLC purification. LC-MS Retention Time: (Method 3)=1.803 min and (Method 2)=2.759 min; $^1$H NMR (400 MHz, DMSO-$d_6$) δ 8.45 (d, J=5.2 Hz, 1H), 8.25 (m, 1H), 8.04 (ddd, J=15.4, 7.7, 2.2 Hz, 2H), 7.71-7.51 (m, 4H), 6.92 (d, J=5.2 Hz, 1H), 2.88 (s, 3H); HRMS (ESI) m/z (M+H)$^+$ calcd. for $C_{15}H_{14}N_3$, 236.1189. found 236.1182.

Materials and Methods

Materials:

Different commercial fatty acids as lipoxygenase substrates, were purchased from Nu Chek Prep, Inc. (MN, USA). The fatty acids were further re-purified using a Higgins HAISIL column (5 μm, 250×10 mm) C-18 column. An isocratic elution of 85% solvent A (99.9% methanol and 0.1% acetic acid): 15% solvent B (99.9% water and 0.1% acetic acid) was used to purify all the fatty acids. Post purification, the fatty acids were stored at −80° C. for a maximum of 6 months. Lipoxygenase product 13-(S)-HPODE was generated by reacting the linoleic acid (LA) with soybean LOX-1. The product generation protocol involved reacting 50 μM substrate in 500 mL of 100 mM Borate buffer pH 9.2 with soybean LOX-1. A small sample from the big reaction was monitored on the UV-Vis spectrometer till complete turnover. The products were then extracted using dichloromethane, reduced with trimethylphosphite, evaporated to dryness and reconstituted in methanol. The products were HPLC purified using an isocratic elution of 75% A (99.9% methanol and 0.1% acetic acid): 25% B (99.9% water and 0.1% acetic acid). The products were tested for their purity using LC-MS/MS and were found to have >98% purity. Ovine COX-1 (Cat. No. 60100) and human COX-2 (Cat. No. 60122) were purchased from Cayman chemicals. All other chemicals were of high quality and used without further purification.

High-Throughput Screen (HTS)

HTS Materials.

Dimethyl sulfoxide (DMSO) ACS grade was from Fisher, while ferrous ammonium sulfate, Xylenol Orange (XO), sulfuric acid, and Triton X-100 were obtained from Sigma-Aldrich.

HTS Compound Library.

A 74,290 compound library was screened in 7 to 15 concentrations ranging from 0.7 nM to 57 μM. The library included 61,548 diverse small drug-like molecules that are part of the NIH Small Molecule Repository. A collection of 1,372 compounds from the Centers of Methodology and Library Development at Boston University (BUCMLD) and University of Pittsburgh (UPCMLD) were added to the library. Several combinatorial libraries from Pharmacopeia, Inc. totaled 2,419 compounds. An additional 1,963 compounds from the NCI Diversity Set were included. Lastly, 6,925 compounds with known pharmacological activity were added to provide a large and diverse screening collection.

HTS Protocol and Analysis.

All screening operations were performed on a fully integrated robotic system (Kalypsys Inc, San Diego, Calif.) as before (Kenyon et al., J. Med. Chem., 54, 5485-5497). Three μL of enzyme (40 nM 15-hLO-1, final concentration) was dispensed into 1536-well Greiner black clear-bottom assay plate. Compounds and controls (23 nL) were transferred via Kalypsys PinTool equipped with 1536-pin array. The plate was incubated for 15 min at room temperature, and then a 1 μL aliquot of substrate solution (50 μM arachidonic acid final concentration) was added to start the reaction. The reaction was stopped after 6.5 min by the addition of 4 μL FeXO solution (final concentrations of 200 μM Xylenol Orange (XO) and 300 μM ferrous ammonium sulfate in 50 mM sulfuric acid). After a short spin (1000 rpm, 15 sec), the assay plate was incubated at room temperature for 30 minutes. The absorbances at 405 and 573 nm were recorded using ViewLux high throughput CCD imager (Perkin-Elmer, Waltham, Mass.) using standard absorbance protocol settings. During dispense, enzyme and substrate bottles were kept submerged into +4° C. recirculating chiller bath to minimize degradation. Plates containing DMSO only (instead of compound solutions) were included approximately every 50 plates throughout the screen to monitor any systematic trend in the assay signal associated with reagent dispenser variation or decrease in enzyme specific activity.

Data was analyzed in a similar method as described before (Kenyon et al., *J. Med. Chem.*, 54, 5485-5497). Briefly, assay plate-based raw data was normalized to controls and plate-based data corrections were applied to filter out background noise. All concentration response curves (CRCs) were fitted using in-house developed software (http://ncgc.nih.gov/pub/openhts/). Curves were categorized into four classes: complete response curves (Class 1), partial curves (Class 2), single point actives (Class 3) and inactives (Class 4). Compounds with the highest quality, Class 1 and Class 2 curves, were prioritized for follow-up.

Overexpression and Purification of Lipoxygenases.

Different lipoxygenases such as, human reticulocyte 15-lipoxygenase-1 (12/15-LOX), human epithelial 15-lipoxygenase-2 (15-LOX-2), human platelet 12-lipoxygenase (12-LOX) were expressed as N-terminal $His_6$-tagged proteins and were purified via immobilized metal affinity chromatography (IMAC) using Ni-NTA resins for 12/15-LOX and 15-LOX-2, whereas Ni-IDA resin for 12-LOX.[75,76] The protein purity was evaluated by SDS-PAGE analysis and was found to be greater than 90%. Human 5-lipoxygenase (5-LOX) was expressed as a non-tagged protein and used as a crude ammonium sulfate protein fraction, as published previously.[77]

Lipoxygenase UV-Vis Assay.

The inhibitor compounds were screened initially using one concentration point on a Perkin-Elmer Lambda 40 UV-Vis spectrometer. The percent inhibition was determined by comparing the enzyme rates of the control (DMSO solvent) and the inhibitor sample by following the formation of the conjugated diene product at 234 nm ($\varepsilon$=25,000 $M^{-1}$ $cm^{-1}$). The reactions were initiated by adding either of ~40 nM 12-LOX, 40 nM 12/15-LOX, 0.5 μM 15-LOX-2 or ~200 nM 5-LOX (ammonium sulfate suspension) to a cuvette with a 2 mL reaction buffer constantly stirred using a magnetic stir bar at room temperature (22° C.). It should be noted that LOX isozymes are often expressed in the inactive demetallated form, so it is best to utilize activity to determine the optimal LOX concentration for the assay (optimal rate of approximately 0.001 abs/sec at 10 μM AA). Reaction buffers used for various lipoxygenase were as follows-25 mM HEPES (pH 7.3), 0.3 mM $CaCl_2$, 0.1 mM EDTA, 0.2 mM ATP, 0.01% Triton X-100, 10 μM AA for the crude, ammonium sulfate precipitated 5-LOX; 25 mM Hepes (pH 8), 0.01% Triton X-100, 10 μM AA for 12-LOX and 25 mM Hepes buffer (pH 7.5), 0.01% Triton X-100, 10 μM AA for 12/15-LOX and 15-LOX-2. The substrate concentration was quantitatively determined by allowing the enzymatic reaction to go to completion in the presence of 15-LOX-2. For the inhibitors that showed more than 50% inhibition at the one point screens (25 μM inhibitor), $IC_{50}$ values were obtained by determining the enzymatic rate at various inhibitor concentrations and plotted against inhibitor concentration (Approximate range: 0.1 to 25 μM inhibitor), followed by a hyperbolic saturation curve fit (assuming total enzyme concentration [E]<<$K_i^{app}$, so $IC_{50}$~$K_i^{app}$). It should be noted that all of the potent inhibitors displayed greater than 80% maximal inhibition, unless stated in the tables. Inhibitors were stored at −20° C. in DMSO.

Pseudoperoxidase Assay.

The pseudo-peroxidase activity rates were determined with BWb70c as the positive control, 13-(S)-HPODE as the oxidizing product and 12/15-LOX on a Perkin-Elmer Lambda 40 UV-Vis spectrometer, as described previously.[78] Briefly, activity was determined by monitoring the decrease at 234 nm (product degradation) in buffer (50 mM Sodium Phosphate (pH 7.4), 0.3 mM $CaCl_2$, 0.1 mM EDTA, 0.01% Triton X100, and 20 μM 13-(S)-HPODE). 12/15-LOX was added to buffer (22° C.) and the reaction initiated by addition of 20 μM inhibitor (1:1 ratio to product). The percent consumption of 13-(S)-HPODE was recorded, with individual controls being conducted with inhibitor alone with product and enzyme alone with product.

Steady-State Inhibition Kinetics.

The steady-state kinetics experiments were performed with the parent analogue, compound 1 (ML351) to determine the mode of inhibition, as described before.[56,79] The inhibitor concentrations ranging from 0, 0.05, 2 and 5 μM were used. Reactions were initiated by adding approximately 40-60 nM 12/15-LOX to a constantly stirring 2 mL cuvette containing 1-20 μM AA in 25 mM HEPES buffer (pH 7.5), in the presence of 0.01% Triton X-100. Lipoxygenase rates were determined by monitoring the formation of the conjugated product, 15-HpETE, at 234 nm ($\varepsilon$=25 000 $M^{-1}$ $cm^{-1}$) with a Perkin-Elmer Lambda 40 UV-Vis spectrometer. The substrate concentration was quantitatively determined by allowing the enzymatic reaction to proceed to completion using 15-LOX-2. Kinetic data were obtained by recording initial enzymatic rates, at varied substrate and inhibitor concentrations, and subsequently fitted to the Henri-Michaelis-Menten equation, using KaleidaGraph (Synergy) to determine the microscopic rate constants, $V_{max}$ (μmol/min/mg) and $V_{max}/K_M$ (μmol/min/mg/μM). These rate constants were subsequently replotted with $1/V_{max}$ and $K_M/V_{max}$ versus inhibitor concentration, yielding $K_i'$ and $K_i$, respectively.

Cyclooxygenase Assay.

About 2-5 μg of either COX-1 or COX-2 were added to buffer containing 0.1 M Tris-HCl buffer (pH 8.0), 5 mM EDTA, 2 mM phenol and 1 μM hematin at 37° C. The inhibitors were added to the reaction cell, followed by an incubation of 5 minutes with either of the COX enzymes. The reaction was then initiated by adding 100 μM AA in the reaction cell. Data was collected using a Hansatech DW1 oxygen electrode and the consumption of oxygen was recorded. Indomethacin and the solvent DMSO, were used as positive and negative controls, respectively and the percent inhibition of the enzyme was calculated by comparing the rates from samples and the controls.

HT22 Cell Culture Assay.

Glutathione depletion was induced in HT22 cells by glutamate treatment, and LDH release into the medium was measured to detect cell death as described.[38] Briefly, HT22 cells were cultured in DMEM containing 10% fetal bovine serum and penicillin/streptomycin (all media from Invitrogen). For viability experiments, cells were seeded at $1 \times 10^4$ cells/well in 96-well plates (Corning) and treated 18 h later, when the cells were approximately 50-70% confluent. Treatment consisted of exchanging the medium to 100 μl fresh culturing medium and adding 5 mM glutamate (stock solution 0.5 M in PBS) in the presence or absence of DMSO (maximum 0.1% final concentration) as control or the indicated concentrations of 1. Lactate dehydrogenase (LDH) content was determined separately for the cell extracts and corresponding media using a Cytotoxicity Detection Kit (Roche), and the percentage of LDH released to the medium calculated after subtracting the corresponding background value. To determine levels of the 12/15-LOX metabolite, 12-HETE, HT22 cells were cultured in 75 cm² flasks in DMEM medium without phenol red, supplemented with 5% FBS, and treated the cells the next day when cells were 50-70% confluent. 24 hours later, the eicosanoid-containing fraction was isolated via Sep-Pak C-18 column, and 12-HETE was detected with a 12-HETE ELISA kit (Enzo Life Sciences), used according to the manufacturer's instruction. Three independent experiments were evaluated. For the MS samples, the above procedure was modified slightly. The eicosanoids containing fractions were transferred to scintillation vials followed by addition of perdeuterated 13-HODE (13-$d_{31}$-HODE), as an internal control for extraction and 1.5% glacial acetic acid for protein precipitation. The samples were extracted with methylene chloride, reduced with trimethylphosphite and evaporated to dryness. The dry samples were then re-constituted in methanol and an internal control 12-deuterated ($d_8$)-HETE (12-$d_8$-HETE), was added to each sample for detector response variation and it was assumed that the change in detector response for 12-HETE and 12-$d_8$-HETE would be similar. The samples were run on and analyzed by Finnigan LTQ liquid chromatography-tandem mass spectrometry (LC-MS/MS) system. A Thermo Electron Corp. Aquasil (3 μm, 100 mm×2.1 mm) C-18 column was used to detect the HETEs with an elution protocol consisting of 0.2 mL/min flow rate and a linear gradient from 54.9% ACN, 45% H₂O, and 0.1% THF to 69.9% ACN, 30% H₂O, and 0.1% THF. The electrospray voltage was set to 5.0 kV and a global acquisition MS mode was used. The MS-MS scan was performed for the five most abundant precursor ions. The Collision Induced Dissociation (CID) was used for MS-MS with collision energy of 35 eV. The corresponding 12-HETE, 12-$d_8$-HETE and 13-$d_{31}$-HODE compounds were detected using selective ion monitoring analysis (m/z=318.7 to 319.7, 326.8 to 327.7 and 325.8 to 326.8 respectively) in negative ion mode and then identified by fragmentation pattern (12-HETE, parent ion at m/z 319 and fragments at m/z 179 and 163; 12-$d_8$-HETE, parent ion at m/z 327 and fragments at m/z 184 and 13-$d_{31}$-HODE, parent ion m/z 326 and fragments at m/z 213) from MS-MS. The peak area of 12-$d_8$-HETE for each sample was normalized to the area of 13-$d_{31}$-HODE. The peak intensities of 12-HETEs were normalized to the corrected 12-$d_8$-HETE intensities. The amount of 12-HETE in samples was estimated from the pure 12-(S)-HETE standard curve.

Distal MCAO Model of Permanent Focal Ischemia in Mice.

To study 1 in a model of distal middle cerebral artery occlusion (distal MCAO),[74] C57B16J mice were treated with ferric chloride (FeCl₃) to cause occlusion of the distal middle cerebral artery. Mice were kept under anesthesia with 1.5% isoflurane in a nitrous oxide/oxygen mixture via facemask. The body temperature was monitored by a rectal probe and maintained at 37±0.3° C. by a homoeothermic blanket control unit. Briefly, mice were placed in a stereotaxic frame, the scalp was opened and right temporal muscle was dissected. The area between zygomatic arch and squamous bone was thinned by a high-speed drill and cooled with saline. The trace of MCA was visualized and thin bony film was lifted up by forceps. After that a laser-Doppler flowmetry probe was placed 2 mm posterior, 6 mm lateral to the bregma to monitor the regional cerebral blood flow (rCBF). After obtaining a stable epoch of the pre-ischemic rCBF, a piece of 10% FeCl₃ saturated filter paper was placed over the intact dura mater along the trace of MCA and the rCBF was continuously monitored during the next 3 hours. After 2 hours of ischemia, either 50 mg/kg 1, or DMSO vehicle was injected intraperitoneally. Following sacrifice at 24 hours, brains were sectioned into 1 mm slices, and infarct sizes were determined by staining with 2,3,5-triphenyltetrazolium chloride (TTC), using the indirect method (infarct volume=contralateral volume minus uninfarcted ipsilateral volume). Both the surgeon carrying out the procedure, as well as the researcher determining infarct volumes were blinded as to which treatment the mice received.

Abbreviations.

LOX, lipoxygenase; sLOX-1, soybean lipoxygenase-1; 12/15-LOX, human reticulocyte 15-lipoxygenase-1; 15-LOX-1, human reticulocyte 15-lipoxygenase-1; 15-LOX-2, human epithelial 15-lipoxygenase-2; 12-LOX, human platelet 12-lipoxygenase; rabbit 12/15-LOX, rabbit reticulocyte 12/15-lipoxygenase; mouse 12/15-LOX, mouse reticulocyte 12/15-lipoxygenase; COX, Cyclooxygenase; NDGA, nordihydroguaiaretic acid; AA, arachidonic acid; 15-HpETE, 15-(S)-hydroperoxyeicosatetraenoic acid; 12-HpETE, 12-(S)-hydroperoxyeicosatetraenoic acid; LA, linoleic acid; 13-(S)-HpODE, 13-(S)-hydroperoxyoctadecadienoic acid; 12-HETE, 12-(S)-hydroxyeicosatetraenoic acid; 15-HETE, 15-(S)-hydroxyeicosatetraenoic acid; $V_{max}$, maximal velocity (μmol/min); $K_M$, Henri-Michaelis-Menten Constant (μM); [E], total active enzyme concentration; $IC_{50}$, inhibitor constant at 50% inhibition; $K_i^{app}$, apparent inhibition constant when [E]>>$K_i^{app}$; XO, xylenol orange; HTS, high-throughput screening; MLSMR, Molecular Libraries Small Molecule Repository; MLPCN, Molecular Libraries Probe Centers Network; qHTS, quantitative high-throughput screening; CRC, concentration response curve; EDC, 1-Ethyl-3-(3-dimethylaminopropyl)carbodiimide hydrochloride; BTAC, N-benzyl-triethylammonium chloride; BWB70C, N-[3-[3-(-Fluorophenoxy)phenyl]-1-methyl-2-propenyl]-N-hydroxyurea; LDA, lithium diisopropylamide.

REFERENCES FOR EXAMPLE 1

1. Solomon, E. I.; Zhou, J.; Neese, F.; Pavel, E. G. New Insights from Spectroscopy into the Structure/Function Relationships of Lipoxygenases. *Chem. Biol.* 1997, 4, 795-808.
2. Brash, A. R. Lipoxygenases: Occurrence, Functions, Catalysis and Acquisition of Substrate. *J. Biol. Chem.* 1999, 274, 23679-23682.
3. Ivanov, I.; Heydeck, D.; Hofheinz, K.; Roffeis, J.; O'Donnell, V. B.; Kuhn, H.; Walther, M. Molecular Enzymology of Lipoxygenases. *Arch. Biochem. Biophys.* 2010, 503, 161-174.
4. Schnurr, K.; Belkner, J.; Ursini, F.; Schewe, T.; Kuhn, H. The Selenoenzyme Phospholipid Hydroperoxide Glutathione Peroxidase Controls the Activity of the 15-Lipoxygenase with Complex Substrates and Preserves the Specificity of the Oxygenation Products. *J. Biol. Chem.* 1996, 271, 4653-4658.
5. Tong, W. G.; Ding, X. Z.; Hennig, R.; Witt, R. C.; Standop, J.; Pour, P. M.; Adrian, T. E. Leukotriene B4 Receptor Antagonist Ly293111 Inhibits Proliferation and Induces Apoptosis in Human Pancreatic Cancer Cells. *Clin. Can. Res.* 2002, 8, 3232-3242.

6. Wenzel, S. E.; Kamada, A. K. Zileuton: The First 5-Lipoxygenase Inhibitor for the Treatment of Asthma. *Ann. Pharmacother.* 1996, 30, 858-864.
7. O'Byrne, P. M.; Israel, E.; Drazen, J. M. Antileukotrienes in the Treatment of Asthma. *Annals Int. Med.* 1997, 127, 472-480.
8. Berger, W.; De Chandt, M. T.; Cairns, C. B. Zileuton: Clinical Implications of 5-Lipoxygenase Inhibition in Severe Airway Disease. *Int. J. Clin. Pract.* 2007, 61, 663-6676.
9. Muller-Peddinghaus, R. Potential Anti-Inflammatory Effects of 5-Lipoxygenase Inhibition—Exemplified by the Leukotriene Synthesis Inhibitor Bay X 1005. *J. Physiol. Pharmacol* 1997, 48, 529-536.
10. Klickstein, L. B.; Shapleigh, C.; Goetzl, E. J. Lipoxygenation of Arachidonic Acid as a Source of Polymorphonuclear Leukocyte Chemotactic Factors in Synovial Fluid and Tissue in Rheumatoid Arthritis and Spondyloarthritis. *J. Clin. Investig.* 1980, 66, 1166-1170.
11. Weinblatt, M. E.; Kremer, J. M.; Coblyn, J. S.; Helfgott, S.; Maier, A. L.; Petrillo, G.; Henson, B.; Rubin, P.; Sperling, R. Zileuton, a 5-Lipoxygenase Inhibitor in Rheumatoid Arthritis. *J. Rheumatol.* 1992, 19, 1537-1541.
12. Spanbroek, R.; Grabner, R.; Lotzer, K.; Hildner, M.; Urbach, A.; Ruhling, K.; Moos, M. P.; Kaiser, B.; Cohnert, T. U.; Wahlers, T.; Zieske, A.; Plenz, G.; Robenek, H.; Salbach, P.; Kuhn, H.; Radmark, O.; Samuelsson, B.; Habenicht, A. J. Expanding Expression of the 5-Lipoxygenase Pathway within the Arterial Wall During Human Atherogenesis. *P.N.A.S.* 2003, 100, 1238-1243.
13. Funk, C. D. Leukotriene Modifiers as Potential Therapeutics for Cardiovascular Disease. *Nat. Rev. Drug Discovery* 2005, 4, 664-6672.
14. Lotzer, K.; Funk, C. D.; Habenicht, A. J. The 5-Lipoxygenase Pathway in Arterial Wall Biology and Atherosclerosis. *Biochim. Biophys. Acta.* 2005, 1736, 30-37.
15. Bleich, D.; Chen, S.; Gu, J. L.; Nadler, J. L. The Role of 12-Lipoxygenase in Pancreatic-Cells (Review). *Int. J. Mol. Med.* 1998, 1, 265-272.
16. Hedrick, C. C.; Kim, M. D.; Nataraj an, R. D.; Nadler, J. L. 12-Lipoxygenase Products Increase Monocyte:Endothelial Interactions. *Adv. Exp. Med Biol.* 1999, 469, 455-460.
17. Thomas, C. P.; Morgan, L. T.; Maskrey, B. H.; Murphy, R. C.; Kuhn, H.; Hazen, S. L.; Goodall, A. H.; Hamali, H. A.; Collins, P. W.; O'Donnell, V. B. Phospholipid-Esterified Eicosanoids Are Generated in Agonist-Activated Human Platelets and Enhance Tissue Factor-Dependent Thrombin Generation. *J. Biol. Chem.* 2010, 285, 6891-6903.
18. Hussain, H.; Shornick, L. P.; Shannon, V. R.; Wilson, J. D.; Funk, C. D.; Pentland, A. P.; Holtzman, M. J. Epidermis Contains Platlet-Type 12-Lipoxygenase That Is Overexpressed in Germinal Layer Keratinocytes in Psoriasis. *Am. J. Physiol.* 1994, 266, C243-C253.
19. Connolly, J. M.; Rose, D. P. Enhanced Angiogenesis and Growth of 12-Lipoxygenase Gene-Transfected Mcf-7 Human Breast Cancer Cells in Athymic Nude Mice. *Cancer Lett.* 1998, 132, 107-112.
20. Ding, X. Z.; Iversen, P.; Cluck, M. W.; Knezetic, J. A.; Adrian, T. E. Lipoxygenase Inhibitors Abolish Proliferation of Human Pancreatic Cancer Cells. *Biochem. Biophys. Res. Comm.* 1999, 261, 218-223.
21. Haeggstrom, J.; Funk, C. D. Lipoxygenase and Leukotriene Pathways: Biochemistry, Biology, and Roles in Disease. *Chem. Rev.* 2011, 111, 5866-5898.
22. Kuhn, H.; Walther, M.; Kuban, R. J. Mammalian Arachidonate 15-Lipoxygenases: Structure, Function, and Biological Implications. *Prostag. Lipid M.* 2002, 68-69, 263-290.
23. Weaver, J. R.; Holman, T. R.; Imai, Y.; Jadhav, A.; Kenyon, V.; Maloney, D. J.; Nadler, J. L.; Rai, G.; Simeonov, A.; Taylor-Fishwick, D. A. Integration of Pro-Inflammatory Cytokines, 12-Lipoxygenase and Nox-1 in Pancreatic Islet Beta Cell Dysfunction. *Mol. Cell. Endo.* 2012, 358, 88-95.
24. Stavniichuk, R.; Drel, V. R.; Shevalye, H.; Vareniuk, I.; Stevens, M. J.; Nadler, J. L.; Obrosova, I. G. Role of 12/15-Lipoxygenase in Nitrosative Stress and Peripheral Prediabetic and Diabetic Neuropathies. *Free Rad. Bio. & Med.* 2010, 49, 1036-1045.
25. Obrosova, I. G.; Stavniichuk, R.; Drel, V. R.; Shevalye, H.; Vareniuk, I.; Nadler, J. L.; Schmidt, R. E. Different Roles of 12/15-Lipoxygenase in Diabetic Large and Small Fiber Peripheral and Autonomic Neuropathies. *Am. J. Path.* 2010, 177, 1436-1447.
26. Dobrian, A. D.; Lieb, D. C.; Ma, Q.; Lindsay, J. W.; Cole, B. K.; Ma, K.; Chakrabarti, S. K.; Kuhn, N. S.; Wohlgemuth, S. D.; Fontana, M.; Nadler, J. L. Differential Expression and Localization of 12/15 Lipoxygenases in Adipose Tissue in Human Obese Subjects. *Biochem. Biophys. Res. Comm.* 2010, 403, 485-490.
27. Chakrabarti, S. K.; Wen, Y.; Dobrian, A. D.; Cole, B. K.; Ma, Q.; Pei, H.; Williams, M. D.; Bevard, M. H.; Vandenhoff, G. E.; Keller, S. R.; Gu, J.; Nadler, J. L. Evidence for Activation of Inflammatory Lipoxygenase Pathways in Visceral Adipose Tissue of Obese Zucker Rats. *Am. J. Physiol. Endo. Metab.* 2010, 300, E175-E187.
28. Nunemaker, C. S.; Chen, M.; Pei, H.; Kimble, S. D.; Keller, S. R.; Carter, J. D.; Yang, Z.; Smith, K. M.; Wu, R.; Bevard, M. H.; Garmey, J. C.; Nadler, J. L. 12-Lipoxygenase-Knockout Mice Are Resistant to Inflammatory Effects of Obesity Induced by Western Diet. *Am. J. Physiol. Endo. Metab.* 2008, 295, E1065-E1075.
29. Succol, F.; Pratico, D. A Role for 12/15 Lipoxygenase in the Amyloid Beta Precursor Protein Metabolism. *J. Neurochem.* 2007, 103, 380-387.
30. Yao, Y.; Clark, C. M.; Trojanowski, J. Q.; Lee, V. M.; Pratico, D. Elevation of 12/15 Lipoxygenase Products in Ad and Mild Cognitive Impairment. *Ann. Neurol.* 2005, 58, 623-626.
31. Pratico, D.; Zhukareva, V.; Yao, Y.; Uryu, K.; Funk, C. D.; Lawson, J. A.; Trojanowski, J. Q.; Lee, V. M. 12/15-Lipoxygenase Is Increased in Alzheimer's Disease: Possible Involvement in Brain Oxidative Stress. *Am. J. Pathol.* 2004, 164, 1655-1662.
32. Haynes, R. L.; van Leyen, K. 12/15-Lipoxygenase Expression Is Increased in Oligodendrocytes and Microglia of Periventricular Leukomalacia. *Devel. Neuro.* 2013, 35, 140-154.
33. O'Flaherty, J. T.; Wooten, R. E.; Samuel, M. P.; Thomas, M. J.; Levine, E. A.; Case, L. D.; Akman, S. A.; Edwards, I. J. Fatty Acid Metabolites in Rapidly Proliferating Breast Cancer. *PloS one* 2013, 8, e63076.
34. Yigitkanli, K.; Pekcec, A.; Karatas, H.; Pallast, S.; Mandeville, E.; Joshi, N.; Smirnova, N.; Gazaryan, I.; Ratan, R. R.; Witztum, J. L.; Montaner, J.; Holman, T. R.; Lo, E. H.; van Leyen, K. Inhibition of 12/15-Lipoxygenase as Therapeutic Strategy to Treat Stroke. *Ann. Neurol.* 2013, 73, 129-135.
35. van Leyen, K. Lipoxygenase: An Emerging Target for Stroke Therapy. *CNS Neurol. Disord. Drug Targets* 2013, 12, 191-199.

36. Lo, E. H.; Dalkara, T.; Moskowitz, M. A. Mechanisms, Challenges and Opportunities in Stroke. *Nat. Rev. Neurosci.* 2003, 4, 399-415.
37. Donnan, G. A.; Fisher, M.; Macleod, M.; Davis, S. M. Stroke. *Lancet.* 2008, 371, 1612-1623.
38. Li, Y.; Maher, P.; Schubert, D. A Role for 12-Lipoxygenase in Nerve Cell Death Caused by Glutathione Depletion. *Neuron* 1997, 19, 453-463.
39. Lovat, P. E.; Oliverio, S.; Ranalli, M.; Corazzari, M.; Rodolfo, C.; Bernassola, F.; Aughton, K.; Maccarrone, M.; Hewson, Q. D.; Pearson, A. D.; Melino, G.; Piacentini, M.; Redfern, C. P. Gadd153 and 12-Lipoxygenase Mediate Fenretinide-Induced Apoptosis of Neuroblastoma. *Cancer Res.* 2002, 62, 5158-5167.
40. Canals, S.; Casarejos, M. J.; de Bernardo, S.; Rodriguez-Martin, E.; Mena, M. A. Nitric Oxide Triggers the Toxicity Due to Glutathione Depletion in Midbrain Cultures through 12-Lipoxygenase. *J. Biol. Chem.* 2003, 278, 21542-21549.
41. Khanna, S.; Roy, S.; Ryu, H.; Bahadduri, P.; Swaan, P. W.; Ratan, R. R.; Sen, C. K. Molecular Basis of Vitamin E Action: Tocotrienol Modulates 12-Lipoxygenase, a Key Mediator of Glutamate-Induced Neurodegeneration. *J. Biol. Chem.* 2003, 278, 43508-43515.
42. Khanna, S.; Roy, S.; Slivka, A.; Craft, T. K.; Chaki, S.; Rink, C.; Notestine, M. A.; DeVries, A. C.; Parinandi, N. L.; Sen, C. K. Neuroprotective Properties of the Natural Vitamin E Alpha-Tocotrienol. *Stroke* 2005, 36, 2258-2264.
43. van Leyen, K.; Kim, H. Y.; Lee, S. R.; Jin, G.; Arai, K.; Lo, E. H. Baicalein and 12/15-Lipoxygenase in the Ischemic Brain. *Stroke* 2006, 37, 3014-3018.
44. van Leyen, K.; Lee, S. R.; Siddiq, A.; Ratan, R. R.; Lo, E. H. 12/15-Lipoxygenase and the Proteasome as Mediators of Neuronal Oxidative Stress and Stroke. *Program No* 1356, 2004 *Abstract Viewer/Itinerary Planner. Washington, D.C.: Society for Neuroscience* 2004.
45. Jin, G.; Arai, K.; Murata, Y.; Wang, S.; Stins, M. F.; Lo, E. H.; van Leyen, K. Protecting against Cerebrovascular Injury: Contributions of 12/15-Lipoxygenase to Edema Formation Following Transient Focal Ischemia. *Stroke* 2008, 39, 2538-2543.
46. Pallast, S.; Arai, K.; Wang, X.; Lo, E. H.; van Leyen, K. 12/15-Lipoxygenase Targets Neuronal Mitochondria under Oxidative Stress. *J. Neurochem.* 2009, 111, 882-889.
47. Pallast, S.; Arai, K.; Pekcec, A.; Yigitkanli, K.; Yu, Z.; Wang, X.; Lo, E. H.; van Leyen, K. Increased Nuclear Apoptosis-Inducing Factor after Transient Focal Ischemia: A 12/15-Lipoxygenase-Dependent Organelle Damage Pathway. *J. Cereb. Blood Flow Metab.* 2010, 30, 1157-1167.
48. Seiler, A.; Schneider, M.; Forster, H.; Roth, S.; Wirth, E. K.; Culmsee, C.; Plesnila, N.; Kremmer, E.; Radmark, O.; Wurst, W.; Bornkamm, G. W.; Schweizer, U.; Conrad, M. Glutathione Peroxidase 4 Senses and Translates Oxidative Stress into 12/15-Lipoxygenase Dependent- and Aif-Mediated Cell Death. *Cell Metab.* 2008, 8, 237-248.
49. Kenyon, V.; Chorny, I.; Carvajal, W. J.; Holman, T. R.; Jacobson, M. P. Novel Human Lipoxygenase Inhibitors Discovered Using Virtual Screening with Homology Models. *J. Med. Chem.* 2006, 49, 1356-1363.
50. Carroll, J.; Jonsson, E. N.; Ebel, R.; Hartman, M. S.; Holman, T. R.; Crews, P. Probing Sponge-Derived Terpenoids for Human 15-Lipoxygenase Inhibitors. *J. Org. Chem.* 2001, 66, 6847-6851.
51. Whitman, S.; Gezginci, M.; Timmermann, B. N.; Holman, T. R. Structure-Activity Relationship Studies of Nordihydroguaiaretic Acid Inhibitors toward Soybean, 12-Human, and 15-Human Lipoxygenase. *J. Med. Chem.* 2002, 45, 2659-2661.
52. Amagata, T.; Whitman, S.; Johnson, T. A.; Stessman, C. C.; Loo, C. P.; Lobkovsky, E.; Clardy, J.; Crews, P.; Holman, T. R. Exploring Sponge-Derived Terpenoids for Their Potency and Selectivity against 12-Human, 15-Human, and 15-Soybean Lipoxygenases. *J. Nat. Prod.* 2003, 66, 230-235.
53. Cichewicz, R. H.; Kenyon, V. A.; Whitman, S.; Morales, N. M.; Arguello, J. F.; Holman, T. R.; Crews, P. Redox Inactivation of Human 15-Lipoxygenase by Marine-Derived Meroditerpenes and Synthetic Chromanes: Archetypes for a Unique Class of Selective and Recyclable Inhibitors. *J. Am. Chem. Soc.* 2004, 126, 14910-14920.
54. Vasquez-Martinez, Y.; Ohri, R. V.; Kenyon, V.; Holman, T. R.; Sepulveda-Boza, S. Structure-Activity Relationship Studies of Flavonoids as Potent Inhibitors of Human Platelet 12-Hlo, Reticulocyte 15-Hlo-1, and Prostate Epithelial 15-Hlo-2. *Bio. Med. Chem.* 2007, 15, 7408-7425.
55. Deschamps, J. D.; Kenyon, V. A.; Holman, T. R. Baicalein Is a Potent in Vitro Inhibitor against Both Reticulocyte 15-Human and Platelet 12-Human Lipoxygenases. *Bioorg. Med. Chem.* 2006, 14, 4295-4301.
56. Rai, G.; Kenyon, V.; Jadhav, A.; Schultz, L.; Armstrong, M.; Jameson, J. B.; Hoobler, E.; Leister, W.; Simeonov, A.; Holman, T. R.; Maloney, D. J. Discovery of Potent and Selective Inhibitors of Human Reticulocyte 15-Lipoxygenase-1. *J. Med. Chem.* 2010, 53, 7392-7404.
57. Ngu, K.; Weinstein, D. S.; Liu, W.; Langevine, C.; Combs, D. W.; Zhuang, S.; Chen, X.; Madsen, C. S.; Harper, T. W.; Ahmad, S.; Robl, J. A. Pyrazole-Based Sulfonamide and Sulfamides as Potent Inhibitors of Mammalian 15-Lipoxygenase. *Bio. Med. Chem. Let.* 2011, 21, 4141-4145.
58. Weinstein, D. S.; Liu, W.; Gu, Z.; Langevine, C.; Ngu, K.; Fadnis, L.; Combs, D. W.; Sitkoff, D.; Ahmad, S.; Zhuang, S.; Chen, X.; Wang, F. L.; Loughney, D. A.; Atwal, K. S.; Zahler, R.; Macor, J. E.; Madsen, C. S.; Murugesan, N. Tryptamine and Homotryptamine-Based Sulfonamides as Potent and Selective Inhibitors of 15-Lipoxygenase. *Bio. Med. Chem. Let.* 2005, 15, 1435-1440.
59. Weinstein, D. S.; Liu, W.; Ngu, K.; Langevine, C.; Combs, D. W.; Zhuang, S.; Chen, C.; Madsen, C. S.; Harper, T. W.; Robl, J. A. Discovery of Selective Imidazole-Based Inhibitors of Mammalian 15-Lipoxygenase: Highly Potent against Human Enzyme within a Cellular Environment. *Bio. Med. Chem. Let.* 2007, 17, 5115-5120.
60. Malterud, K. E.; Rydland, K. M. Inhibitors of 15-Lipoxygenase from Orange Peel. *J. Ag. Food Chem.* 2000, 48, 5576-5580.
61. Sailer, E. R.; Schweizer, S.; Boden, S. E.; Ammon, H. P. T.; Safayhi, H. Characterization of an Acetyl-11-Keto-B-Boswellic Acid and Arachidonate-Binding Regulatory Site of 5-Lipoxygenase Using Phoroaffinity Labeling. *Eur. J. Biochem.* 1998, 256, 364-368.
62. Sendobry, S. M.; Cornicelli, J. A.; Welch, K.; Bocan, T.; Tait, B.; Trivedi, B. K.; Colbry, N.; Dyer, R. D.; Feinmark, S. J.; Daugherty, A. Attenuation of Diet-Induced Atherosclerosis in Rabbits with a Highly Selective 15-Lipoxygenase Inhibitor Lacking Significant Antioxidant Properties. *British J. pharmacol.* 1997, 120, 1199-1206.
63. Diana, G. D.; Treasurywala, A. M.; Bailey, T. R.; Oglesby, R. C.; Pevear, D. C.; Dutko, F. J. A Model for Compounds Active against Human Rhinovirus-14 Based on X-Ray Crystallography Data. *J. Med. Chem.* 1990, 33, 1306-1311.

64. Xia, Q.; Ganem, B. Metal-Mediated Variants of the Passerini Reaction: A New Synthesis of 4-Cyanooxazoles. *Synthesis* 2002, 14, 1969-1972.

65. Dewar, M. J. S.; Turchi, I. J. Cornforth Rearrangement. *J. Am. Chem. Soc.* 1974, 96, 6148-6152.

66. Boros, E. E.; Johns, B. A.; Garvey, E. P.; Koble, C. S.; Miller, W. H. Synthesis and Hiv-Integrase Strand Transfer Inhibition Activity of 7-Hydroxy[1,3]Thiazolo[5,4-B] Pyridin-5(4h)-Ones. *Bio. Med. Chem. Let.* 2006, 16, 5668-5672.

67. Ratan, R. R.; Murphy, T. H.; Baraban, J. M. Oxidative Stress Induces Apoptosis in Embryonic Cortical Neurons. *J. Neurochem.* 1994, 62, 376-379.

68. Ratan, R. R.; Ryu, H.; Lee, J.; Mwidau, A.; Neve, R. L. In Vitro Model of Oxidative Stress in Cortical Neurons. *Methods Enzymol.* 2002, 352, 183-190.

69. Murphy, T. H.; Schnaar, R. L.; Coyle, J. T. Immature Cortical Neurons Are Uniquely Sensitive to Glutamate Toxicity by Inhibition of Cystine Uptake. *FASEB J.* 1990, 4, 1624-1633.

70. van Leyen, K.; Siddiq, A.; Ratan, R. R.; Lo, E. H. Proteasome Inhibition Protects Neuronal Cells from Oxidative Glutamate Toxicity. *J. Neurochem.* 2005, 92, 824-830.

71. Zhang, J. H.; Chung, T. D.; Oldenburg, K. R. A Simple Statistical Parameter for Use in Evaluation and Validation of High Throughput Screening Assays. *J. Biomol. Screen* 1999, 4, 67-73.

72. Mogul, R.; Johansen, E.; Holman, T. R. Oleyl Sulfate Reveals Allosteric Inhibition of Soybean Lipoxygenase-1 and Human 15-Lipoxygenase. *Biochemistry* 2000, 39, 4801-4807.

73. Wecksler, A. T.; Kenyon, V.; Deschamps, J. D.; Holman, T. R. Substrate Specificity Changes for Human Reticulocyte and Epithelial 15-Lipoxygenases Reveal Allosteric Product Regulation. *Biochemistry* 2008, 47, 7364-75.

74. Karatas, H.; Erdener, S. E.; Gursoy-Ozdemir, Y.; Gurer, G.; Soylemezoglu, F.; Dunn, A. K.; Dalkara, T. Thrombotic Distal Middle Cerebral Artery Occlusion Produced by Topical Fecl(3) Application: A Novel Model Suitable for Intravital Microscopy and Thrombolysis Studies. *J. Cereb. Blood Flow Metab.* 2011, 31, 1452-1460.

75. Ohri, R. V.; Radosevich, A. T.; Hrovat, K. J.; Musich, C.; Huang, D.; Holman, T. R.; Toste, F. D. A Re(V)-Catalyzed C—N Bond-Forming Route to Human Lipoxygenase Inhibitors. *Org. Let.* 2005, 7, 2501-2504.

76. Chen, X. S.; Brash, A. R.; Funk, C. D. Purification and Characterization of Recombinant Histidine-Tagged Human Platelet 12-Lipoxygenase Expressed in a Baculovirus/Insect Cell System. *Eur. J. Biochem.* 1993, 214, 845-852.

77. Robinson, S. J.; Hoobler, E. K.; Riener, M.; Loveridge, S. T.; Tenney, K.; Valeriote, F. A.; Holman, T. R.; Crews, P. Using Enzyme Assays to Evaluate the Structure and Bioactivity of Sponge-Derived Meroterpenes. *J. Nat. Prod.* 2009, 72, 1857-1863.

78. Hoobler, E. K.; Holz, C.; Holman, T. R. Pseudoperoxidase Investigations of Hydroperoxides and Inhibitors with Human Lipoxygenases. *Bioorg. Med. Chem.* 2013, 21, 3894-3899.

79. Kenyon, V.; Rai, G.; Jadhav, A.; Schultz, L.; Armstrong, M.; Jameson, J. B., 2nd; Perry, S.; Joshi, N.; Bougie, J. M.; Leister, W.; Taylor-Fishwick, D. A.; Nadler, J. L.; Holinstat, M.; Simeonov, A.; Maloney, D. J.; Holman, T. R. Discovery of Potent and Selective Inhibitors of Human Platelet-Type 12-Lipoxygenase. *J. Med. Chem.* 2011, 54, 5485-5497.

Example 2: Effect on Warfarin-Associated Hemorrhage Following Experimental Stroke in Mice The inventors have shown that ML351 can reduce infarct size in a mouse model of transient focal ischemia (see Example 1), indicating it is protective in cases of stroke. These studies are expanded on by investigating possible benefits of ML351 in cases of stroke with hemorrhagic transformation, reflecting the clinical situation of patients who are on oral anticoagulants, specifically warfarin. Warfarin is typically given as a blood thinner to patients with atrial fibrillation who are at a 5-fold increased risk of ischemic stroke. Around 20% of all stroke patients over 80 years old have atrial fibrillation (Heart Disease ad Stroke Statistics—2014 Update; Circulation (2014) 129(3):399-410. doi: 10.1161/01.cir.0000442015.53336.12).

Figure 9A:
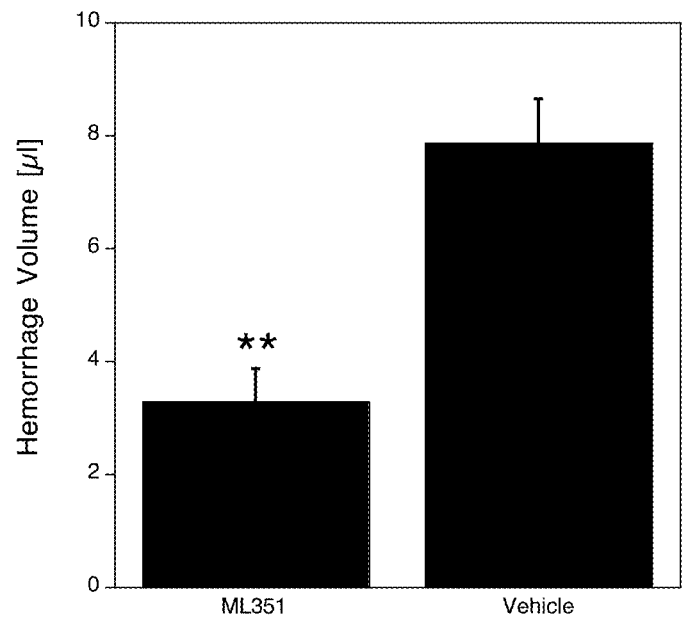
FIG. 9A is a plot showing that hemorrhage in the ischemic hemisphere of warfarin-treated mice is significantly reduced by ML351. **p<0.001

Because these anticoagulants are seen as increasing the risk of bleeding (known as hemorrhagic transformation), this makes patients ineligible for treatment with tPA in case of stroke, because tPA similarly has an increased risk of hemorrhage as side effect. Patients on warfarin who experience a stroke, thus do not receive any form of drug treatment. To test the hypothesis that inhibition of 12/15-LOX may reduce hemorrhagic transformation, ML351 are tested in two different scenarios:

A) In warfarin-pretreated mice subjected to transient focal ischemia with 3 h occlusion, 50 mg/kg ML351 was administered by i.p. injection 3 h after onset of ischemia (FIG. 9A). This mimics the situation of a patient on warfarin who experiences a severe stroke with hemorrhagic transformation.

Figure 9B:
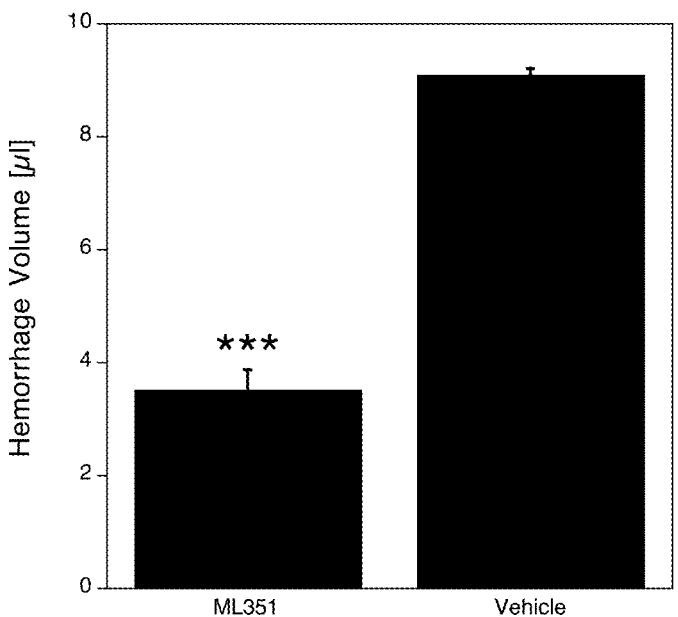
FIG. 9B is a plot showing that hemorrhage in the ischemic hemisphere of warfarin-treated mice subjected to experimental stroke and treated with tPA is also significantly reduced by ML351. ***p<0.0001
Figure 10:
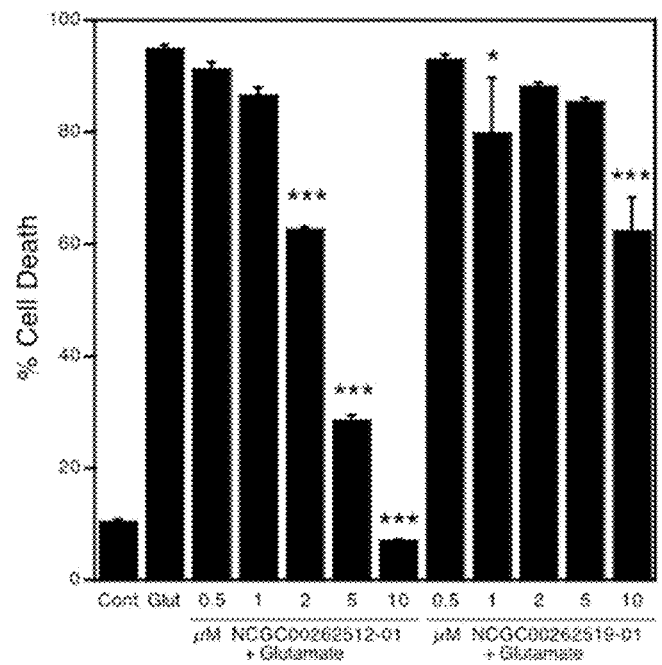
FIG. 10 shows that compounds 8 and 7, labeled as NCGC00262512-01 and NCGC00262519-01 respectively, provide protection against oxidative stress-induced cell death by glutamate treatment in the mouse hippocampal HT22 cell line. Compound 8 showed a dose-dependent cell protective effect, with efficacy increasing from concentrations of 2 to 10 against the mouse 12/15-LOX enzyme in HT22 cells, while compound 7 showed some protection at a concentration of 10 μM. *p<0.05 vs Glutamate alone; ***p<0.001 vs Glutamate alone, Dunnett's Multiple Comparison test
Figure 11:
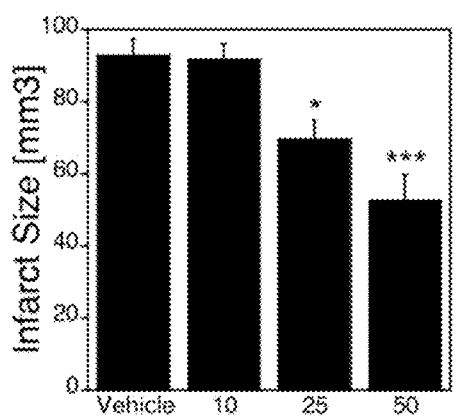
FIG. 11 shows that the classical filament model of transient focal ischemia (90 minutes ischemia, sacrifice at 24 hours) was used to determine dosage of ML351 needed to provide a significant benefit in terms of reducing infarct size. While a dose of 10 mg/kg did not change the infarct, both 25 mg/kg and 50 mg/kg were significantly protective, with 50 mg/kg providing a greater reduction. This shows ML351 has good efficacy in this established mouse model of stroke.
Figures 12A, 12B:
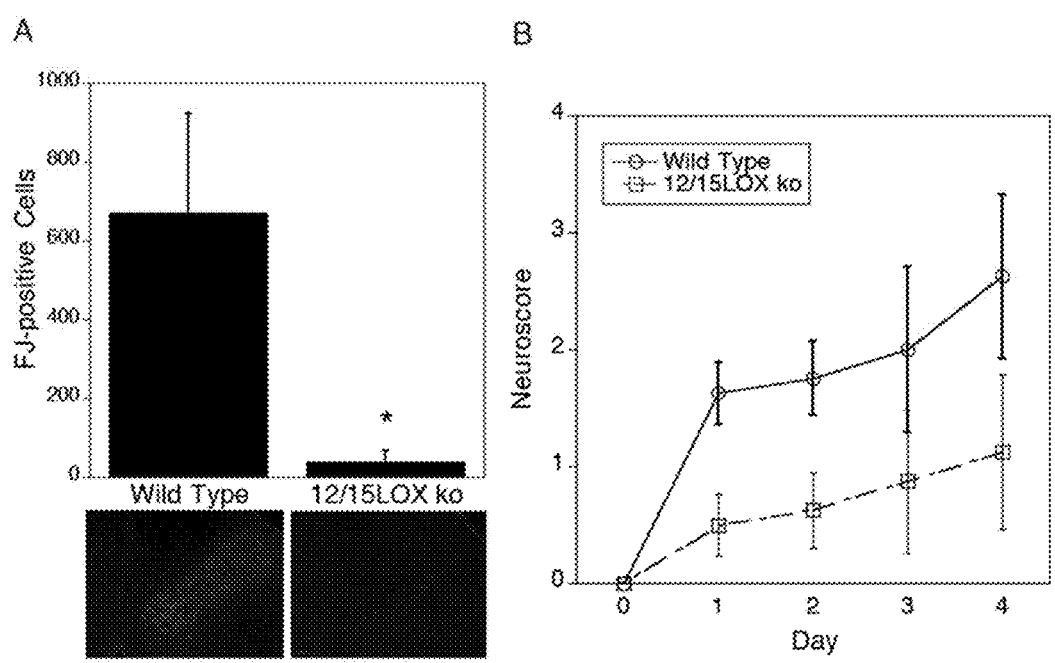
FIGS. 12A-12B are an injury assessment in 12/15-LOX knockout mice compared to wild-type mice, showing reduced brain injury following cardiac arrest in the 12/15-LOX knockout mice. (A) Neuronal damage, measured as number of FluoroJade-positive cells. Shown below the graph are representative images taken from the cortex. (B) A 10-point neuroscore was used to determine the degree of cognitive impairment. The difference in behavioral deficit between wild-type and 12/15-LOX knockout mice was significant by 2-way ANOVA (p=0.024).

B) To investigate if administering tPA to patients with an ischemic stroke who are on warfarin can be made safe, warfarin-pretreated mice were subjected to 2 h of transient focal ischemia, then treated with tPA 4 h after onset of ischemia, and administered 50 mg/kg ML351 by i.p. injection concurrently with tPA. Again, vehicle-treated mice experienced massive hemorrhage, and again this was significantly reduced by ML351 (FIG. 9B).

These experiments show that patients who are on oral anticoagulants such as warfarin and experience a stroke, could now be treated either with ML351 as stand-alone treatment, or with ML351 as adjuvant to tPA. This widens the patient pool eligible for treatment following a stroke.

What is claimed is:

1. A method of treating a condition involving 12/15-lipoxygenase in a subject, the method comprising administering to the subject an effective amount of a compound of Formula I:

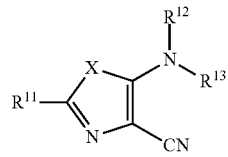

Formula I or a pharmaceutically acceptable salt thereof, wherein:
X is O or S;
R$^{11}$ is an aryl, heteroaryl, cyclyl, or heterocyclyl, each of which can be optionally substituted, provided that the heteroaryl excludes S from the heteroaryl ring and when aryl is phenyl, optional substituent on the phenyl is not alkyl or alkoxy; and
R$^{12}$ and R$^{13}$ are independently hydrogen, halogen, alkyl, alkenyl, alkynyl, aralkyl, acyl, aryl, heteroaryl, cyclyl or heterocyclyl, each of which can be optionally substituted.

2. The method of claim 1, wherein R$^{11}$ is an aryl or heteroaryl, each of which can be optionally substituted, provided that the heteroaryl excludes S from the heteroaryl ring and when aryl is phenyl, optional substituent on the phenyl is not alkyl or alkoxy.

3. The method of claim 2, wherein R$^{11}$ is 1-naphthyl, 2-naphthyl, 6-isoquinolinyl, 2,3-dichlorophenyl, or 3,4-dichlorophenyl.

4. The method of claim 1, wherein R$^{12}$ is hydrogen, alkyl, aralkyl, acyl, aryl, or heterocyclyl, each of which can be optionally substituted.

5. The method of claim 4, wherein R$^{12}$ is hydrogen, methyl, ethyl, propyl, butyl, pentyl, or phenyl.

6. The method of claim 1, wherein R$^{13}$ is hydrogen, alkyl, aralkyl, acyl, aryl, or heterocyclyl, each of which can be optionally substituted.

7. The method of claim 6, wherein R$^{13}$ is hydrogen, methyl, ethyl, propyl, butyl, pentyl, or phenyl.

8. The method of claim 1, wherein R$^{12}$ is hydrogen and R$^{13}$ is hydrogen, methyl, ethyl, propyl, butyl, pentyl, or phenyl.

9. The method of claim 1, wherein X is O.

10. The method of claim 1, wherein X is S.

11. The method of claim 1, wherein the compound of Formula I is of:
(i) Formula II:

Formula II

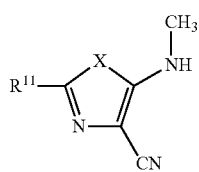

or a pharmaceutically acceptable salt thereof, wherein:
X is O or S; and
R$^{11}$ is an aryl, heteroaryl, cyclyl, or heterocyclyl, each of which can be optionally substituted; or
(ii) Formula III:

Formula III

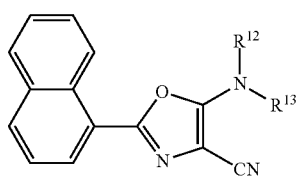

or a pharmaceutically acceptable salt thereof, wherein:
R$^{12}$ and R$^{13}$ are independently hydrogen, halogen, alkyl, alkenyl, alkynyl, aralkyl, acyl, aryl, heteroaryl, cyclyl or heterocyclyl, each of which can be optionally substituted.

12. The method of claim 1, wherein the compound is selected from the group consisting of 5-(methylamino)-2-naphthalen-1-yl-1,3-oxazole-4-carbonitrile (ML351), 2-(2,3-dichlorophenyl)-5-(methylamino)-1,3-oxazole-4-carbonitrile, 2-(3,4-dichlorophenyl)-5-(methylamino)-1,3-oxazole-4-carbonitrile and 5-(methylamino)-2-naphthalen-1-yl-1,3-thiazole-4-carbonitrile.

13. The method of claim 12, wherein the compound is 5-(methylamino)-2-naphthalen-1-yl-1,3-oxazole-4-carbonitrile (ML351).

14. The method of claim 1, wherein the compound inhibits 12/15-lipoxygenase.

15. The method of claim 1, wherein the condition is stroke, periventricular leukomalacia, cardiac arrest with resuscitation, atherosclerosis, Parkinson's disease, Alzheimer's disease, or breast cancer.

16. The method of claim 1, wherein the subject is a mammal.

17. The method of claim 1, wherein the subject is a human.

18. A compound selected from the group consisting of

Compound 7

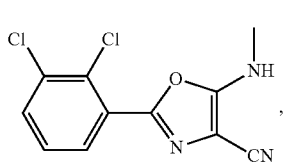

Compound 8

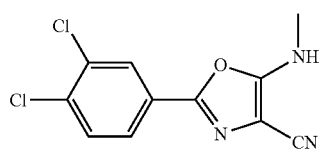

Compound 21

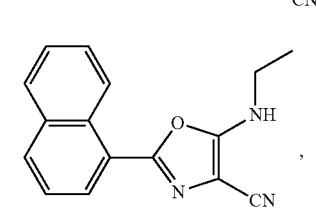

Compound 22

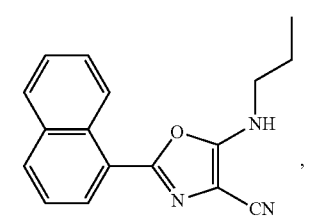

Compound 23

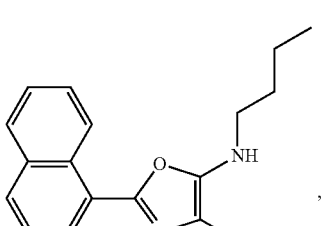

Compound 24
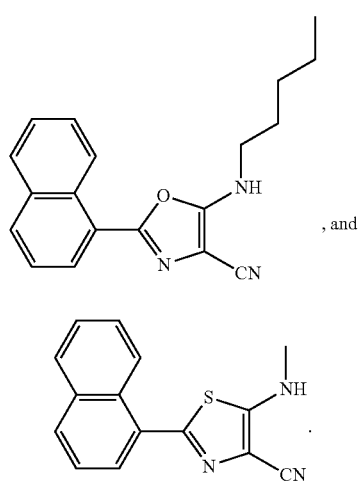
, and
Compound 32
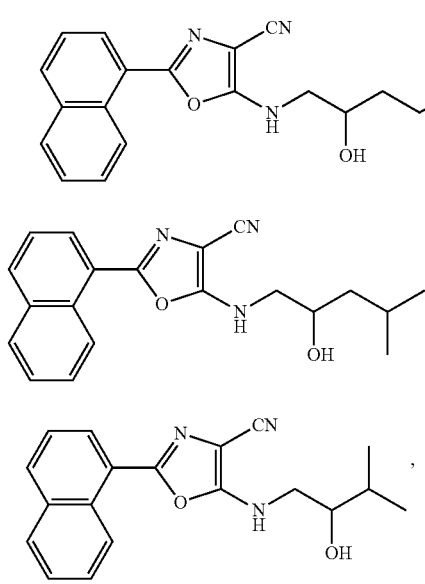
.
19. A compound selected from the group consisting of
Compound 41
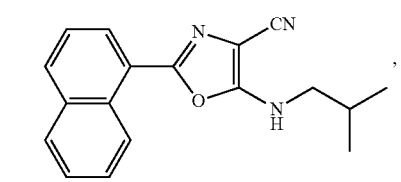
,
Compound 42
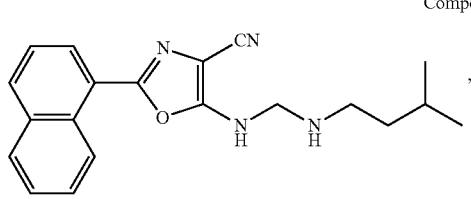
,
Compound 43
,
Compound 44
,
Compound 45
,
Compound 46
,
Compound 47
,
Compound 48
,
Compound 49
,
Compound 50
,
Compound 51
,
Compound 52
,
Compound 53
, -continued
Compound 54
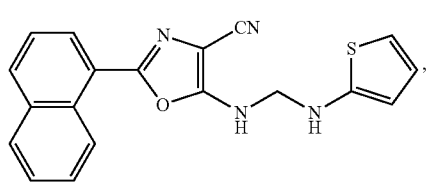
Compound 55
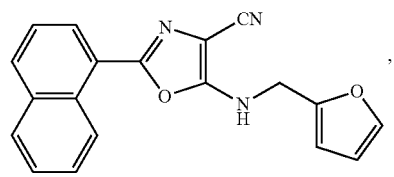
Compound 56
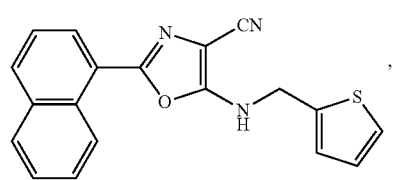
Compound 57
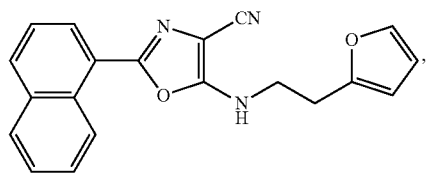
Compound 58
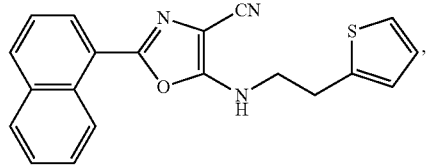
Compound 59
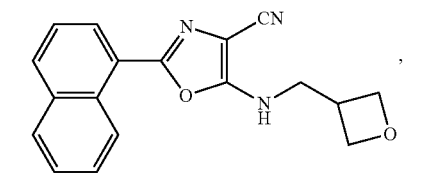
-continued
Compound 60
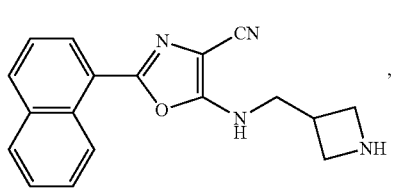
Compound 61
Compound 62
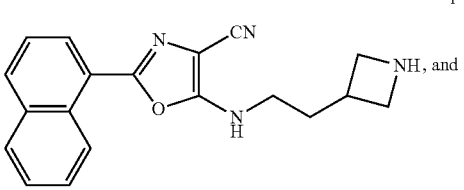
Compound 63
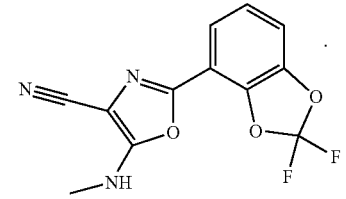
* * * * *

UNITED STATES PATENT AND TRADEMARK OFFICE
CERTIFICATE OF CORRECTION

PATENT NO. : 10,287,279 B2
APPLICATION NO. : 15/048330
DATED : May 14, 2019
INVENTOR(S) : Klaus Joachin Van Leyen et al.

Page 1 of 1

It is certified that error appears in the above-identified patent and that said Letters Patent is hereby corrected as shown below:

On the Title Page

Item (75), for Inventor Klaus Joachin Van Leyen, please replace "Joachin Van" with --Joachim van--.

Signed and Sealed this
Third Day of September, 2019

Andrei Iancu
*Director of the United States Patent and Trademark Office*

UNITED STATES PATENT AND TRADEMARK OFFICE
CERTIFICATE OF CORRECTION

PATENT NO. : 10,287,279 B2
APPLICATION NO. : 15/048330
DATED : May 14, 2019
INVENTOR(S) : Van Leyen et al.

Page 1 of 1

It is certified that error appears in the above-identified patent and that said Letters Patent is hereby corrected as shown below:

On the Title Page

Item (73), for Assignees:
"THE CHILDREN'S HOSPITAL CORPORATION, Boston, MA (US);"
Should be replaced with:
-- THE GENERAL HOSPITAL CORPORATION, Boston, MA (US); --

Signed and Sealed this
Twenty-first Day of July, 2020

Andrei Iancu
*Director of the United States Patent and Trademark Office*